US007026339B2

(12) United States Patent
Yang et al.

(10) Patent No.: US 7,026,339 B2
(45) Date of Patent: Apr. 11, 2006

(54) INHIBITORS OF HCV NS5B POLYMERASE

(76) Inventors: Fan Yang, 70 Peach Orchard Rd., Burlington, MA (US) 01803; Bo Zhang, 10720 Alyssa Way, Fishers, IN (US) 46038; Nancy Anne Wicnienski, 1101 Par 4 Rd., Kalamazoo, MI (US) 49008; Jeffrey Allen Pfefferkorn, 8376 Parkridge Dr., Dexter, MI (US) 48130; Meredith L. Greene, 200 Riverfront Dr., #25F, Detroit, MI (US) 48226; Ke Chen, 300 Durant St., Chapel Hill, NC (US) 27517; Richard A. Nugent, 28 Rockwood Dr., Ashland, MA (US) 01721; Matthew Todd Reding, 7226 Princeton Ave., University City, MO (US) 63130; Robert Charles Kelly, 836 East Gull Lake Dr., Augusta, MI (US) 49012; Mark A. Mitchell, 1628 Dover Rd., Kalamazoo, MI (US) 49008-2242; Lee A. Funk, 5153 Mendip St., Oceanside, CA (US) 92057; Richard Frederick Heier, III, 1227 Blue Spruce La., Columbia, IL (US) 62236-4171; Rebecca Merry Anderson, 7291 Riesling St., Mattawan, MI (US) 49071

( * ) Notice: Subject to any disclaimer, the term of this patent is extended or adjusted under 35 U.S.C. 154(b) by 73 days.

(21) Appl. No.: 10/981,128

(22) Filed: Nov. 3, 2004

(65) Prior Publication Data
US 2005/0154056 A1   Jul. 14, 2005

Related U.S. Application Data

(60) Provisional application No. 60/518,542, filed on Nov. 7, 2003.

(51) Int. Cl.
*A61K 31/255* (2006.01)
*A61K 31/44* (2006.01)
*C07C 309/73* (2006.01)
*C07C 309/75* (2006.01)
*C07D 213/44* (2006.01)

(52) U.S. Cl. ............... 514/346; 514/355; 514/438; 514/466; 514/518; 514/604; 544/131; 544/405; 546/291; 546/316; 546/332; 548/336.1; 548/495; 548/537; 548/561; 548/566; 549/65; 549/78; 549/441; 549/493; 558/58; 564/92

(58) Field of Classification Search ............... 558/58; 544/405; 546/291, 316, 332; 548/336.1, 548/495, 537, 561, 566; 549/65, 78, 441, 549/493; 564/92; 514/346, 355, 438, 466, 514/518, 604
See application file for complete search history.

(56) References Cited

U.S. PATENT DOCUMENTS 6,930,106 B1 * 8/2005 Finzel et al. ............. 514/237.5

FOREIGN PATENT DOCUMENTS

| WO | WO 98/33501 | 8/1998 |
| WO | WO 00/06529 | 2/2000 |
| WO | WO 00/10573 | 3/2000 |
| WO | WO 01/77091 | 10/2001 |
| WO | WO 02/04425 | 1/2002 |

OTHER PUBLICATIONS

De Francesco et al., Antiviral Research, 58(10, Mar. 1-16, 2003.*
Bilfin, Chemical Abstracts, 72:111251, 1970.*
Burlov et al., Chemical Abstracts, 117:203959, 1992.*
Aldred, R., et al., "Magnesium-Mediated Ortho-Specific Formylation And Formaldoximation Of Phenols," *J. Chem. Soc. Perkin Trans 1*, 1994, 1823-1832, vol. 13.
Behrens, S., et al., "Identification And Properties Of The RNA-Dependent RNA Polymerase Of Hepatitis C Virus," *The EMBO Journal*, 1996, 12-22, vol. 15, No. 1.
Berge, S., et al., "Pharmaceutical Salts," *Journal of Pharmaceutical Sciences*, 1977, 1-19, vol. 66, No. 1.
Casiraghi, G., et al., "Selective Reactions Between Phenols And Formaldehyde. A Novel Route To Salicylaldehydes," *J. Chem. Soc. Perkins Trans. 1.*, 1980, 1862-1865.
Ferrari, E., et al., "Characterization Of Soluble Hepatitis C Virus RNA-Dependent RN Polymerase Expressed In *Escherichia Coli*," *Journal of Virology*, 1999, 1649-1654, vol. 73n No. 2.
Guilbert, C. et al., "Isolation And Characterization Of The Fluorescent Alkali Product From Diphosphopyridine Nucleotide*," *Biochemistry*, 1971, 2313, vol. 10, No. 12.
Hepworth, J., et al., "Synthesis And Reactions Of Some Chloro-2,2-Dimethylchromens," *Tetrahedron*, 1981, 2613-2616, vol. 37, No. 15.
Houghton, M., et al., *Hepatitis C Viruses Fields Virology*, Third Edition, 1996, 1035-1058, Edited By B. N. Fields, D. M. Knipe, P. M. Howley, et al., Lippincott-Raven Publishers, Philadelphia.

(Continued)

Primary Examiner—Fiona T. Powers
(74) Attorney, Agent, or Firm—Jeffrey H. Tidwell; Bryan C. Zielinski

(57) ABSTRACT

The present invention relates to compounds, process for their synthesis, compositions and methods for the treatment and prevention of hepatitis C virus (HCV) infection. In particular, the present invention provides novel compounds, pharmaceutical compositions containing such compounds and methods for using these compounds in the treatment or prevention of HCV infection. The present invention also provides processes and intermediates for the synthesis of these compounds.

8 Claims, No Drawings

OTHER PUBLICATIONS

Ishido, S., et al., "Complex Formation Of NS5B With NS3 And NS4A Proteins Of Hepatitis C Virus," *Biochamical. And Biophysical Researc Communications*, 1998, 35-40, vol. 244.

Kato, N., et al., "Molecular Cloning Of The Human Hepatitis C Virus Genome From Japanese Patients With Non-A, Non-B Hepatitis," *Proc. Natl. Acad. Sci.*, USA, 1990, 9524-9528, vol. 87.

Komiyama, M., et al., "Selective Syntheses Using Cyclodextrin As Catalyst. 1. Control Of Orientation In The Attack Of Dichlorocarene At Phenolates," *J. Amer. Chem. Soc.*, 1983, 2018-2021, vol. 105.

Lau, J., et al., "Application Of Six Hepatitis C Virus Genotyping Systems To Sera From Chronic Hepatitis C Patients In The United States," *The Journal of Infectious Diseases*, 1995, 281-289, vol. 171, No. 2.

Lohmann, V., et al., "Biochemical Properties Of Hepatitis C Virus NS5B RNA-Dependent RNA Polymerase And Identification Of amino Acid Sequence Motifs Essential For Enzymatic Activity," *Journal of Virology*, 1997, 8416-8428, vol. 71, No. 11.

Van Dorn, L., et al., "Review: Molecular Biology Of The Hepatitis C Virus," *Journal of Medical Virology*, 1994, 345-356, vol. 43.

Wang, P., et al., "Design, Synthesis, Testing, And Quantitative Structure-Activity Relationship Analysis Of Substituted Salicylaldehyda Schiff Bases Of 1-Amino-3-Hydroxyguanidine Tosylate As new Antiviral Agents Coronavirus," *J. Med. Chem.*, 1990, 608-614, vol. 33, No. 2.

Webster, G., et al., "HCV Genotypes-Role In Pathogenesis Of Diseases And Response To Therapy," *Balliere's Clinical Gastroenterology*, 2000, 229-240, vol 14, No. 2.

* cited by examiner

INHIBITORS OF HCV NS5B POLYMERASE

This application claims priority under 35 U.S.C. § 119(e) to U.S. Provisional Application No. 60/518,542, filed Nov. 7, 2003, and which is hereby incorporated by reference.

FIELD OF THE INVENTION

The present invention relates to compounds, process for their synthesis, compositions and methods for the treatment and prevention of hepatitis C virus (HCV) infection. In particular, the present invention provides novel compounds, pharmaceutical compositions containing such compounds and methods for using these compounds in the treatment or prevention of HCV infection. The present invention also provides processes and intermediates for the synthesis of these compounds.

BACKGROUND

Hepatitis C virus (HCV) is the major etiological agent of post-transfusion and community-acquired non-A non-B hepatitis worldwide. It is estimated that over 150 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy.

Therefore, a need exists for the development of effective antiviral agents for treatment of HCV infection that overcomes the limitations of existing pharmaceutical therapies.

General Viral polymerases are attractive targets for antiviral drug development. For example, inhibitors of Viral RNA polymerase activity have been described; see, for example, JAEN, Juan, et. al., WO 0177091, Altamura et. al., WO 00/06529 and Bailey et. al., WO 00/10573, which references are incorporated by reference herein.

The HCV protein NS5B is an RNA dependent RNA polymerase, see, e.g., Lohmann et al. (1997) J. Virol. 71:8416–8428, Behrens et al. (1996) EMBO J. 15:12–22 and Ishido et al. (1998) Biochem. Biophys. Res. Comm. 244:35–40, which references are incorporated by reference herein. The sequence of various genotypes of HCV NS5B are known (Kato et al. (1990) Proc. Natl. Acad. Sci. USA. 87:9524–9528; Webster, G., et al. (2000) Balliere's Clinical Gastroenterology 14, 229–240; van Doom, L. J. (1994) J. of Medical Virology 43, 345–356; Houghton, M. (1996) Hepatitis C viruses Fields Virology: Third Edition, edited by B. N. Fields, D. M. Knipe, P. M. Howley, et al. Lippincott-Raven Publishers, Philadelphia, pp. 1035–1058; Lau, J. Y. et. al., J Infect Dis. 1995, 171(2), 281–9). However, NS5B contains sequence motifs that are highly conserved among all the RNA-dependent RNA polymerases characterized to date.

SUMMARY

The present invention provides compounds, compositions and methods that are useful for treating viral infections and associated diseases, particularly HCV infections and associated diseases. The compounds of the invention inhibit viral replication, preferably HCV replication. The methods of the invention comprise administering to an infected or susceptible host a therapeutically or prophylactically effective amount of a compound as represented by Formula I,

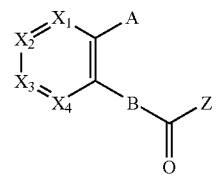

Formula I wherein:

$X_1$, $X_2$, $X_3$ and $X_4$ are independently N or C—$R_1$ provided that only one of $X_1$, $X_2$, $X_3$ and $X_4$ is N;

$R_1$ is selected from the group consisting of H, $C_{1-6}$ alkyl, halogen, —CN, $C_{1-6}$-alkoxy, $C_{1-6}$-fluoroalkyl, $C_{1-6}$-fluroalkoxy and $C_{1-6}$-alkylthio;

any two adjacent —$CR_1$ may be taken together to form a fused aromatic or heteroaromatic substituent of two to three rings;

A is selected from the group consisting of —$OSO_2$-M, —$NR_2SO_2$-M, —$OCR_2$, $R'_2$-M and —$CR_2$, $R'_2$ $SO_n$-M;

B is selected from the group —$CR_2$=N—NH—CO-Z, —$CR_2$=$CR'_2$NHCO-Z, —NH$CR_2$=$CR'_2$CO-Z and -1,2-cyclopropyl-NHCO-Z;

Z is selected from the group -M', —$(CR_2R'_2)_m$-M', —O-M', —$NR_2$-M', and —$(CR_2R'_2)_m$—O-M';

$R_2$ and $R_{12}$ are independently selected from the group consiting of H and $C_{1-6}$ alkyl;

M and M' are independently selected from aryl optionally substituted with 1 to 3 $R_1$, heteroaryl optionally substituted with 1 to 3 $R_1$ and cycloalkyl of 3 to 8 carbons;

n=0, 1, or 2;

m=1, 2, 3 or 4;

or a pharmaceutically acceptable salt or prodrug thereof.

DETAILED DESCRIPTION OF THE INVENTION

Abbreviations and Definitions

The abbreviations used herein are conventional, unless otherwise defined.

The terms "treat", "treating" and "treatment" refer to a method of alleviating or abrogating a disease and/or its attendant symptoms.

The terms "prevent", "preventing" and "prevention" refer to a method of 'barring a subject from acquiring a disease. As used herein, "prevent", "preventing" and "prevention" also include reducing a subject's risk of acquiring a disease.

The term "therapeutically effective amount" refers to that amount of the compound being administered sufficient to prevent development of or alleviate to some extent one or more of the symptoms of the disease being treated.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

"Flaviviridae virus", as used herein, refers to a virus of the family Flaviviridae, which family includes the *Flavivirus, Pestivirus* and *Hepacivirus* or hepatitis C-like virus genera. Representative species of the genus *Flavivirus* include yellow fever virus, tick-borne encephalitis virus, Rio Bravo virus, Japanese encephalitis virus, Tyuleniy virus, Ntaya virus, Uganda S virus, Dengue virus and Modoc virus. Representative species of the genus *Pestivirus* include bovine diarrhea virus, border disease virus and hog cholera virus. A representative species of the genus of hepatitis C-like viruses is hepatitis C virus. Unassigned viruses in the family Flaviviridae are included in the meaning of Flaviviridae virus.

The term "modulate" refers to the ability of a compound to increase or decrease the catalytic activity of a viral polymerase, e.g. a viral RNA polymerase. A modulator preferably activates the catalytic activity of a viral polymerase or more preferably activates or inhibits the catalytic activity of a viral polymerase depending on the concentration of the compound exposed to the viral polymerase or most preferably inhibits the catalytic activity of a viral polymerase.

The term "modify" refers to the act of altering, in whole or in part, the structure of a molecule, e.g., a protein. Modification may be covalent or noncovalent, and includes, but is not limited to, aggregation, association, substitution, conjugation and/or elimination of a chemical group. Modification may alter the function or other properties (e.g., chemical, physical) of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_8$ means 1–8 eight carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, I- and 3-propynyl, 3-butynyl, and the higher homologs and isomers. A "lower alkyl" is a shorter chain alkyl having eight or fewer carbon atoms.

The terms "alkoxy . . . alkylcylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NRR' wherein the R groups can be the same or different alkyl groups.

The term "heteroalkyl," by itself or in combination with another term, means, unless otherwise stated, a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$. Also included in the term "heteroalkyl" are those radicals described in more detail below as "heterocycloalkyl".

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopropyl, cyclobutyl, cyclopentyl, cyclohexyl, 1-cyclohexenyl, 3-cyclohexenyl, cycloheptyl, and the like. Examples of heterocycloalkyl include 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "Fluoroalkyl," are meant to include monofluoroalkyl and polyfluoroalkyl.

The term "aryl," employed alone or in combination with other terms (e.g., aryloxy, arylthioxy, aralkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 1-indolyl, 5-indolyl, 1-isoquinolyl, 5-isoquinolyl, 2-quinoxalinyl, 5-quinoxalinyl, 3-quinolyl, and 6-quinolyl.

Substituents for each of the above noted aryl ring systems are selected from the group of acceptable substituents described below. The term "aralkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl . . . heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R"—SR', -halogen, —SiR'R"R, —OC(O)R', —C(O)R', —CO$_2$R', CONR'R", —OC(O)NR'R"—NR'C(O)R', —NR'—C(O)NR"R'", —NR'COOR", —NH—C(NH$_2$)=NH, —NR'C(NH$_2$)=N—H, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and X" each independently refer to hydrogen, unsubstituted C1—C6alkyl and heteroalkyl, unsubstituted aryl, aryl substituted with 1–3 halogens, unsubstituted alkyl, alkoxy or thioalkoxy groups, or aryl-(C1–C4)alkyl groups. When R' and R" are attached to the same nitrogen atom, they can be combined with the nitrogen atom to form a 3–7 membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: halogen, —OR, —OC(O)R, —NR'R", —SR, —R', —CN, —NO$_2$, —CO$_2$R', —CONR'R:', —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(CI–C4)alkoxy, and perfluoro(CI–C4)alkyl, in a number ranging from zero to the total number of open valences on the aromatic ring system; and where R', R" and R'" are independently selected from hydrogen, (C1–C8)alkyl and heteroalkyl, unsubstituted aryl, (unsubstituted aryl)-(C1–C4)alkyl, and (unsubstituted aryloxy-(C$_1$–C$_4$)alkyl.

Two of the substituents on adjacent atoms of the aryl ring may optionally be replaced with a substituent of the formula —S—C(O)—(CH$_2$)$_q$—R—, wherein S and R are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)$_w$-B-, wherein A and B are independently —CH$_2$—, —O—, —NH—, —S—, —S(O)—, —S(O)$_2$—, —S(O)$_2$NR'— or a single bond, and w is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_w$-G-(CH$_2$)$_{w'}$, where w and w' are independently integers of from 0 to 3, and G is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (CI–C6)alkyl.

As used herein, the term "heteroatom" is meant to include oxygen (O), nitrogen (N), and sulfur (S).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactouronic acids and the like (see, for example, Berge, S. M., et. al. (1977) J. Pharm. Sci., 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner.

The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention unless otherwise stated.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Description of the Embodiments

General Viral polymerases are attractive targets for antiviral drug development. For example, inhibitors of Viral RNA polymerase activity have been described; see, for example, JAEN, Juan, et. al., WO 0177091, Altamura et. al., WO 00/06529 and Bailey et. al., WO 00/10573, which references are incorporated by reference herein.

The HCV protein NS5B is an RNA dependent RNA polymerase, see, e.g., Lohmann et al. (1997) *J. Virol.* 71:8416–8428, Behrens et al. (1996) *EMBO J.* 15:12–22 and Ishido et al. (1998) *Biochem. Biophys. Res. Comm.* 244:35–40, which references are incorporated by reference herein. The sequence of various genotypes of HCV NS5B are known (Kato et al. (1990) *Proc. Natl. Acad. Sci. USA.* 87:9524–9528; Webster, G., et al. (2000) *Balliere's Clinical Gastroenterology* 14, 229–240; van Doom, L. J. (1994) *J. of Medical Virology* 43, 345–356; Houghton, M. (1996) *Hepatitis C viruses Fields Virology*: Third Edition, edited by B. N. Fields, D. M. Knipe, P. M. Howley, et al. Lippincoft-Raven Publishers, Philadelphia, pp. 1035–1058; Lau, J. Y. et. al., *J Infect Dis.* 1995, 171(2), 281–9). However, NS5B contains sequence motifs that are highly conserved among all the RNA-dependent RNA polymerases characterized to date.

The present invention provides compounds having antiviral activity. It is believed that the compounds of the invention will block viral replication by specifically inhibiting the activity of a viral polymerase. Viral RNA polymerase is required for the transcription of genomic RNA, which process is required for replication of the genome of an RNA virus. Therefore, inhibition of viral RNA polymerase will inhibit viral replication.

In a first group of preferred embodiments, the compounds useful for modification of a viral RNA-dependent RNA polymerase protein are of Formula I

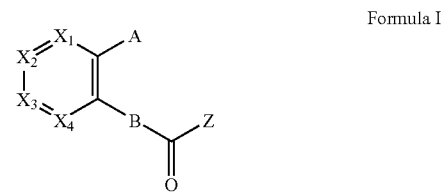

Formula I wherein:
$X_1$, $X_2$, $X_3$ and $X_4$ are independently N or C—$R_1$ provided that only one of $X_1$, $X_2$, $X_3$ and $X_4$ is N;

$R_1$ is selected from the group consisting of H, $C_{1-6}$ alkyl, halogen, —CN, $C_{1-6}$-alkoxy, $C_{1-6}$-fluoroalkyl, $C_{1-6}$-fluroalkoxy and $C_{1-6}$-alkylthio;

any two adjacent —$CR_1$ may be taken together to form a fused aromatic or heteroaromatic substituent of two to three rings;

A is selected from the group consisting of —$OSO_2$-M, —$NR_2SO_2$-M, —$OCR_2R'_2$-M and —$CR_2R'_2SO_n$-M;

B is selected from the group —$CR_2$=N—NH—CO-Z, —$CR_2$=$CR_2$NHCO-Z, —NHCR$_2$=$CR'_2$CO-Z and -1,2-cyclopropyl-NHCO-Z;

Z is selected from the group -M', —$(CR_2R'_2)_m$-M', —O-M', —$NR_2$M', and —$(CR_2R'_2)_m$—O-M';

$R_2$ and $R_{12}$ are independently selected from the group consisting of H and $C_{1-6}$ alkyl;

M and M' are independently selected from aryl optionally substituted with 1 to 3 $R_1$, heteroaryl optionally substituted with 1 to 3 $R_1$ and cycloalkyl of 3 to 8 carbons;

n=0, 1, or 2; and m=1, 2, 3 or 4;

or a pharmaceutically acceptable salt or prodrug thereof.

Further provided herein are compounds of formula (Ia),

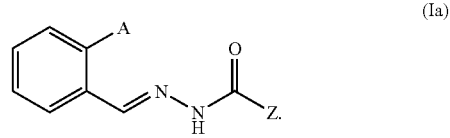

(Ia)

wherein:
A is selected from the group consisting of —$OSO_2$-M, —$NR_2SO2$-M, —$OCR_2R'_2$-M and —$CR_2R'_2SO_n$-M;

Z is selected from the group -M', —$(CR_2R'_2)_m$-M', —O-M', —$NR_2$-M', and —$(CR_2R'_2)_m$—O-M';

$R_1$ is selected from the group consisting of $C_{1-6}$ alkyl, halogen, —CN, $C_{1-6}$-alkoxy, $C_{1-6}$-fluoroalkyl, $C_{1-6}$-fluroalkoxy and $C_{1-6}$-alkylthio;

$R_2$ and $R'_2$ are independently selected from the group consisting of H and $C_{1-6}$ alkyl;

M and M' are independently selected from aryl optionally substituted with 1 to 3 $R_1$, heteroaryl optionally substituted with 1 to 3 $R_1$ and cycloalkyl of 3 to 8 carbons;

n=0, 1, or 2; and m=1, 2, 3 or 4;

or a pharmaceutically acceptable salt or prodrug thereof.

Also provided herein are compounds of formula (Ib),

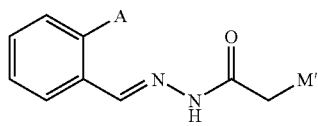

(Ib)

wherein:

A is selected from the group consisting of —OSO$_2$-M, —NR$_2$SO2-M, —OCR$_2$R'$_2$-M and —CR$_2$R'$_2$ SO$_n$-M;

$R_1$ is selected from the group consisting of $C_{1-6}$ alkyl, halogen, —CN, $C_{1-6}$-alkoxy, $C_{1-6}$-fluoroalkyl, $C_{1-6}$-fluroalkoxy and $C_{1-6}$-alkylthio;

$R_2$ and $R'_2$ are independently selected from the group consisting of H and $C_{1-6}$ alkyl;

M and M' are independently selected from aryl optionally substituted with 1 to 3 $R_1$, heteroaryl optionally substituted with 1 to 3 $R_1$ and cycloalkyl of 3 to 8 carbons; and n=0, 1, or 2; or a pharmaceutically acceptable salt or prodrug thereof.

In yet another embodiment are provided compounds of formula (Ic),

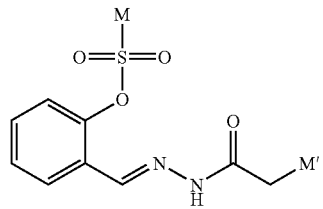

(Ic)

wherein:

$R_1$ is selected from the group consisting of $C_{1-6}$ alkyl, halogen, —CN, $C_{1-6}$-alkoxy, $C_{1-6}$-fluoroalkyl, $C_{1-6}$-fluroalkoxy and $C_{1-6}$-alkylthio; and M and M' are independently selected from aryl optionally substituted with 1 to 3 $R_1$, heteroaryl optionally substituted with 1 to 3 $R_1$ and cycloalkyl of 3 to 8 carbons;

or a pharmaceutically acceptable salt or prodrug thereof.

In still a further embodiment are compounds of formula (Ic), wherein:

$R_1$ is selected from the group consisting of $C_{1-6}$ alkyl, halogen, —CN, $C_{1-6}$-alkoxy, $C_{1-6}$-fluoroalkyl, $C_{1-6}$-fluroalkoxy and $C_{1-6}$-alkylthio; and M and M' are aryl optionally substituted with 1 to 3 $R_1$;

or a pharmaceutically acceptable salt or prodrug thereof.

In still a further embodiment are compounds of formula (Ic), wherein:

$R_1$ is selected from the group consisting of $C_{1-6}$ alkyl, halogen, —CN, $C_{1-6}$-alkoxy, $C_{1-6}$-fluoroalkyl, $C_{1-6}$-fluroalkoxy and $C_{1-6}$-alkylthio; and M and M' are heteroaryl optionally substituted with 1 to 3 $R_1$;

or a pharmaceutically acceptable salt or prodrug thereof.

Non-limiting examples of the group of preferred compounds are given in Table I.

TABLE I

| | | |
|---|---|---|
| 1. | 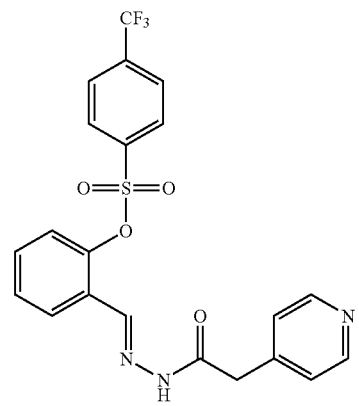 | 2-{(E)-[2-(2-pyridin-4-ylacetyl)-hydrazono]methyl}phenyl 4-(trifluoromethyl)benzenesulfonate; |

TABLE I-continued
| | | |
|---|---|---|
| 2. | 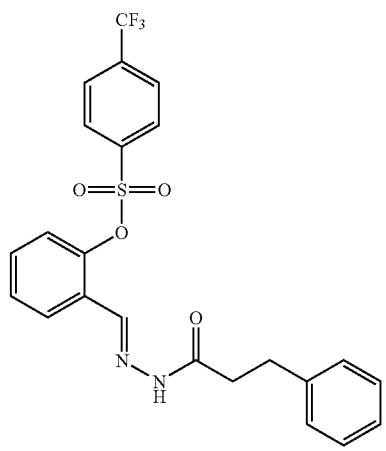 | 2-{(E)-[2-(3-phenylpropanoyl)-hydrazono]methyl}phenyl 4-(trifluoromethyl)benzenesulfonate; |
| 3. | 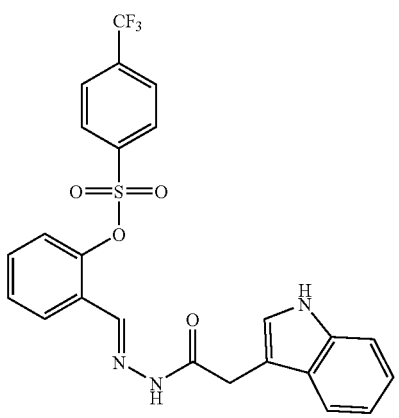 | 2-((E)-{2-[2-(1H-indol-3-yl)-acetyl]hydrazono}methyl)phenyl 4-(trifluoromethyl)benzene-sulfonate; |
| 4. | 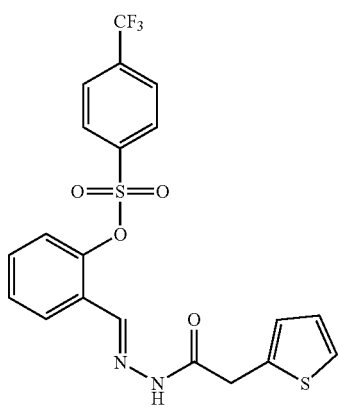 | 2-{(E)-[2-(2-thien-2-ylacetyl)-hydrazono]methyl}phenyl 4-(trifluoromethyl)benzenesulfonate; |

TABLE I-continued
| 5. | 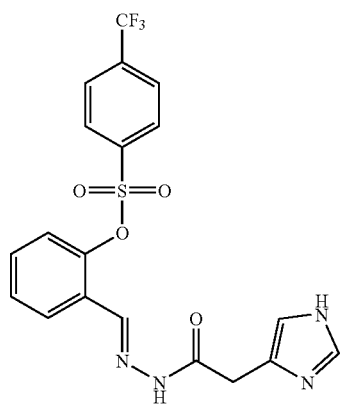 | 2-((E)-{2-[2-(1H-imidazol-4-yl)acetyl]hydrazono}methyl)phenyl 4-(trifluoromethyl)benzenesulfonate; |
| --- | --- | --- |
| 6. | 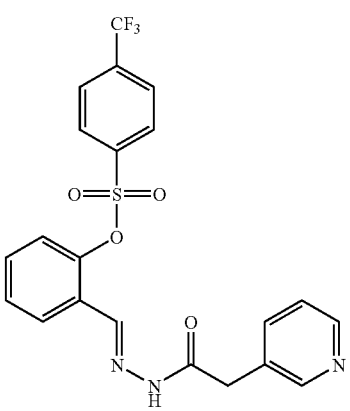 | 2-{(E)-[2-(2-pyridin-3-ylacetyl)hydrazono]methyl}phenyl 4-(trifluoromethyl)benzenesulfonate; |
| 7. | 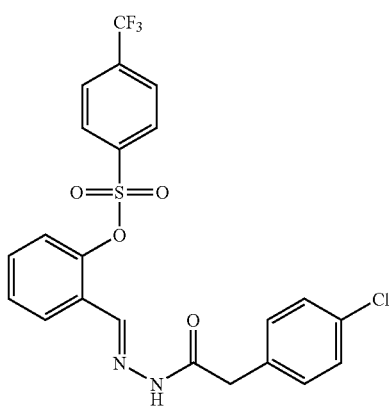 | 2-((E)-{2-[2-(4-chlorophenyl)acetyl]hydrazono}methyl)-phenyl 4-(trifluoromethyl)benzenesulfonate; |
| 8. | 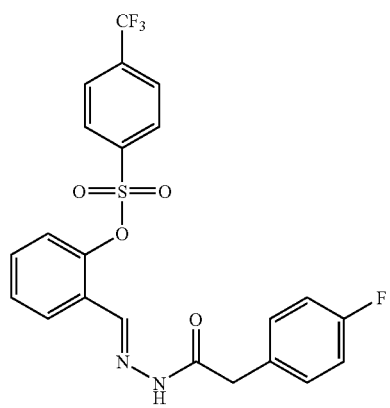 | 2-((E)-{2-[2-(4-fluorophenyl)acetyl]hydrazono}methyl)-phenyl 4-(trifluoromethyl)benzenesulfonate; |

TABLE I-continued
9. 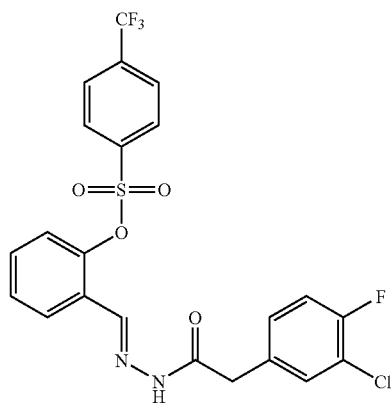 2-((E)-{2-[2-(3-chloro-4-fluorophenyl)acetyl]hydrazono}methyl)-phenyl 4-(trifluoromethyl)benzenesulfonate;
10. 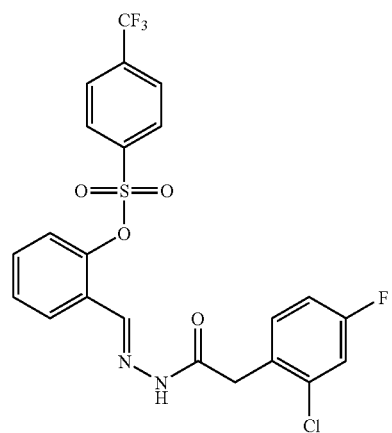 2-((E)-{2-[2-(2-chloro-4-fluorophenyl)acetyl]hydrazono}methyl)-phenyl 4-(trifluoromethyl)benzenesulfonate;
11. 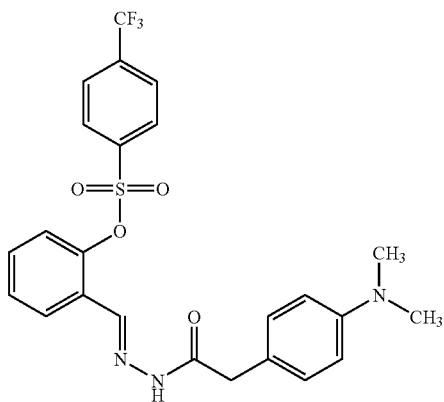 2-[(E)-(2-{2-[4-(dimethylamino)phenyl]acetyl}hydrazono)-methyl]phenyl 4-(trifluoromethyl)benzenesulfonate;

TABLE I-continued
| | | |
|---|---|---|
| 12. | 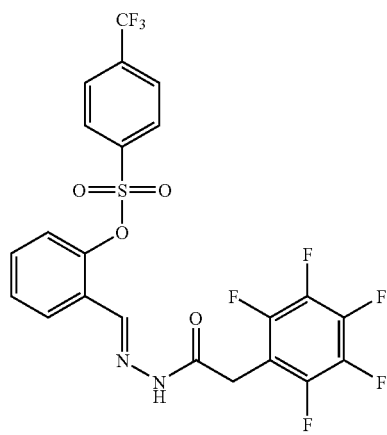 | 2-((E)-{2-[2-(pentafluorophenyl)acetyl]hydrazono}-methyl)phenyl 4-(trifluoromethyl)benzenesulfonate; |
| 13. | 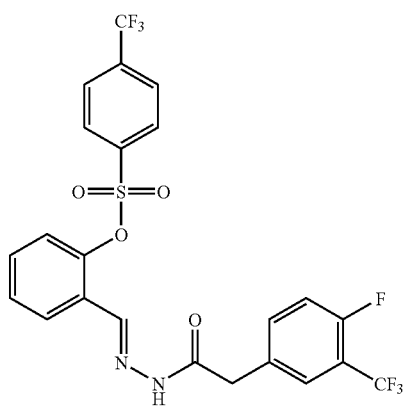 | 2-[(E)-(2-{2-[4-fluoro-3-(trifluoromethyl)phenyl]acetyl}hydrazono)-methyl]phenyl 4-(trifluoromethyl)benzenesulfonate; |
| 14. | 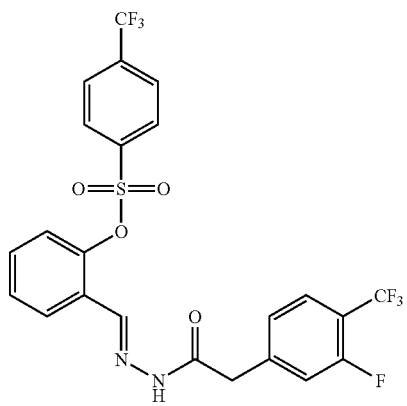 | 2-[(E)-(2-{2-[3-fluoro-4-(trifluoromethyl)phenyl]acetyl}hydrazono)-methyl]phenyl 4-(trifluoromethyl)benzenesulfonate; |

TABLE I-continued
| 15. | 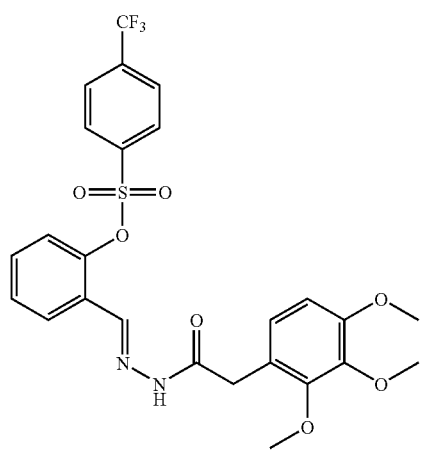 | 2-((E)-{2-[2-(2,3,4-trimethoxyphenyl)acetyl]hydrazono}-methyl)phenyl 4-(trifluoromethyl)-benzenesulfonate |
| 16. | 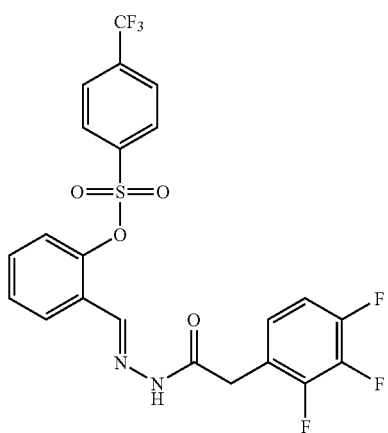 | 2-((E)-{2-[2-(2,3,4-trifluorophenyl)acetyl]hydrazono}methyl)-phenyl 4-(trifluoromethyl)benzenesulfonate; |
| 17. | 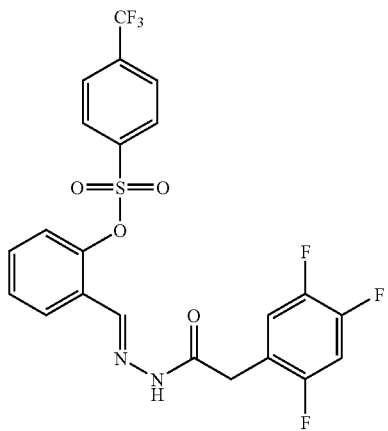 | 2-((E)-{2-[2-(2,4,5-trifluorophenyl)acetyl]hydrazono}methyl)-phenyl 4-(trifluoromethyl)benzenesulfonate; |

TABLE I-continued
| 18. | 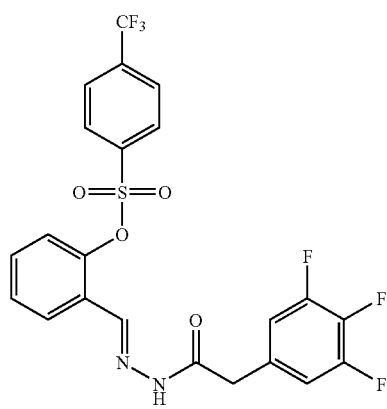 | 2-((E)-{2-[2-(3,4,5-trifluorophenyl)acetyl]hydrazono}methyl)-phenyl 4-(trifluoromethyl)benzenesulfonate; |
| --- | --- | --- |
| 19. | 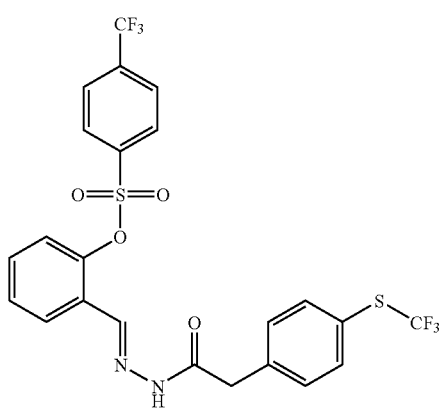 | 2-{(E)-[2-(2-{4-[(trifluoromethyl)thio]phenyl}acetyl)hydrazono]methyl}phenyl 4-(trifluoromethyl)benzenesulfonate; |
| 20. | 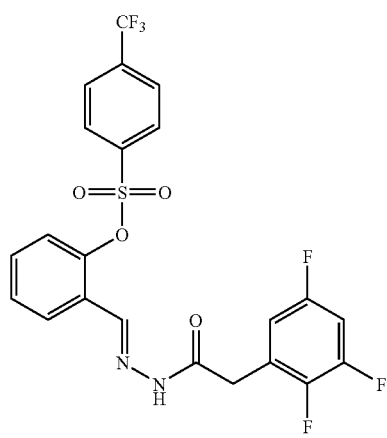 | 2-((E)-{2-[2-(2,3,5-trifluorophenyl)acetyl]hydrazono}methyl)-phenyl 4-(trifluoromethyl)benzenesulfonate; |

TABLE I-continued
| | | |
|---|---|---|
| 21. | 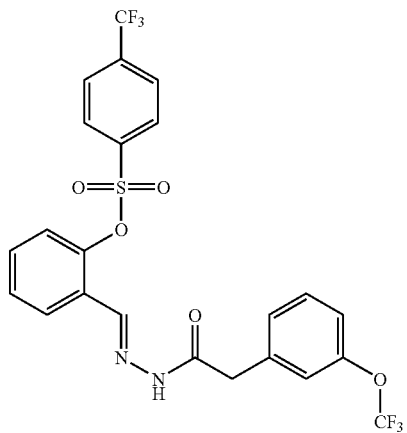 | 2-[(E)-(2-{2-[3-(trifluoromethoxy)phenyl]acetyl}hydrazono)-methyl]phenyl 4-(trifluoromethyl)benzenesulfonate; |
| 22. | 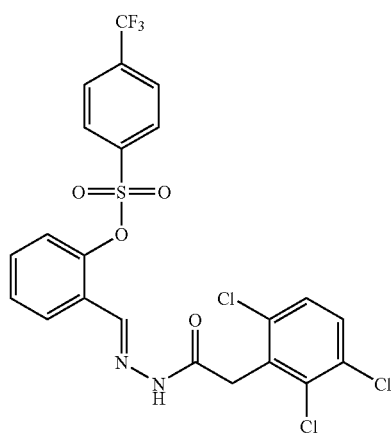 | 2-((E)-{2-[2-(2,3,6-trichlorophenyl)acetyl]hydrazono}methyl)-phenyl 4-(trifluoromethyl)benzenesulfonate; |
| 23. | 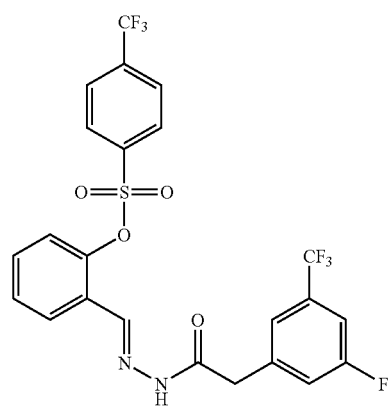 | 2-[(E)-(2-{2-[3-fluoro-5-(trifluoromethyl)phenyl]acetyl}hydrazono)-methyl]phenyl 4-(trifluoromethyl)benzenesulfonate; |

TABLE I-continued
| | | |
|---|---|---|
| 24. | 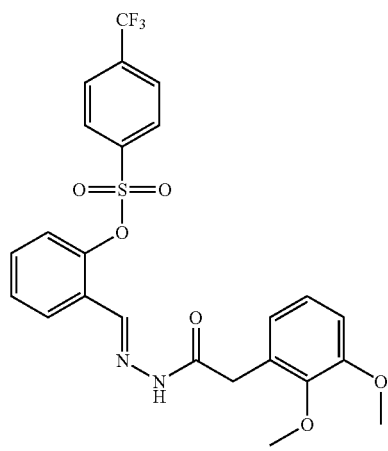 | 2-((E)-{2-[2-(2,3-dimethoxyphenyl)acetyl]hydrazono}methyl)-phenyl 4-(trifluoromethyl)benzenesulfonate; |
| 25. | 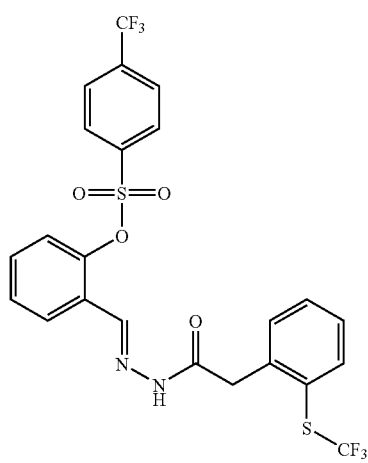 | 2-{(E)-[2-(2-{2-[(trifluoromethyl)thio]-phenyl}acetyl)hydrazono]methyl}phenyl 4-(trifluoromethyl)benzenesulfonate; |
| 26. | 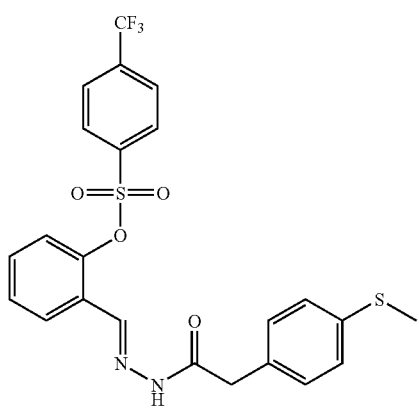 | 2-[(E)-(2-{2-[4-(methylthio)phenyl]acetyl}hydrazono)methyl]-phenyl 4-(trifluoromethyl)benzenesulfonate; |

TABLE I-continued
| | | |
|---|---|---|
| 27. | 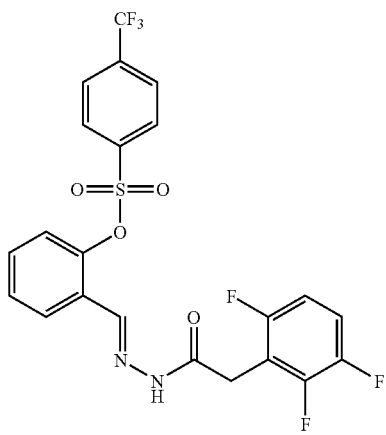 | 2-((E)-{2-[2-(2,3,6-trifluorophenyl)acetyl]hydrazono}methyl)-phenyl 4-(trifluoromethyl)benzenesulfonate; |
| 28. | 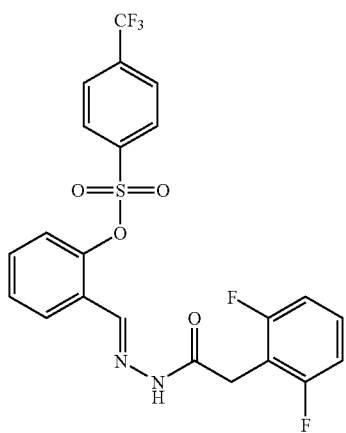 | 2-((E)-{2-[2-(2,6-difluorophenyl)acetyl]hydrazono}methyl)-phenyl 4-(trifluoromethyl)benzenesulfonate; |
| 29. | 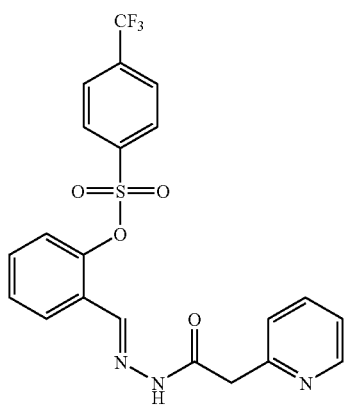 | 2-{(E)-[2-(2-pyridin-2-ylacetyl)hydrazono]methyl}phenyl 4-(trifluoromethyl)benzenesulfonate; |

TABLE I-continued
| 30. | 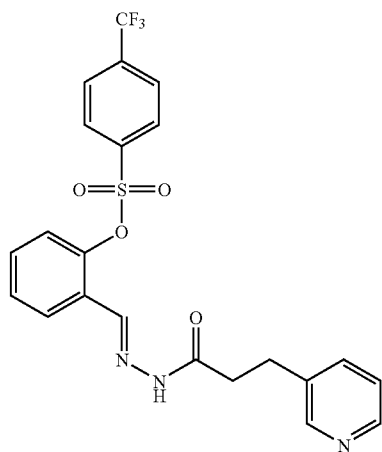 | 2-{(E)-[2-(3-pyridin-3-ylpropanoyl)hydrazono]methyl}phenyl 4-(trifluoromethyl)benzenesulfonate; |
| 31. | 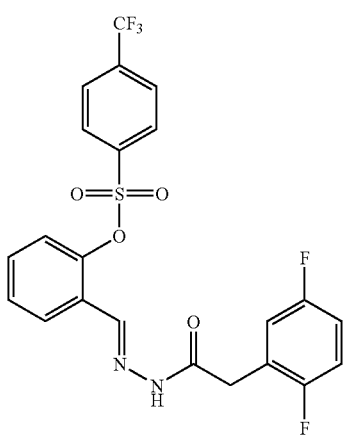 | 2-((E)-{2-[2-(2,5-difluorophenyl)acetyl]hydrazono}methyl)-phenyl 4-(trifluoromethyl)benzenesulfonate; |
| 32. | 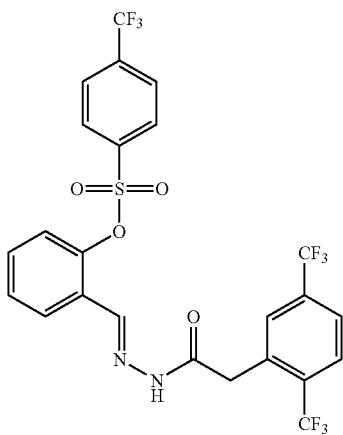 | 2-[(E)-(2-{2-[2,5-bis(trifluoromethyl)phenyl]acetyl}hydrazono)-methyl]phenyl 4-(trifluoromethyl)benzenesulfonate; |

TABLE I-continued
| | | |
|---|---|---|
| 33. | 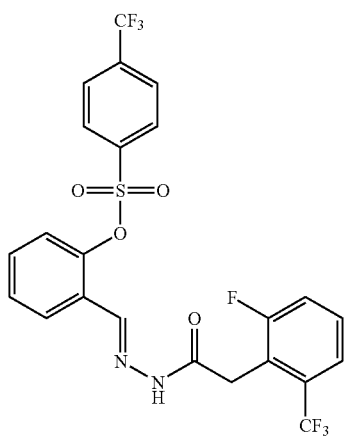 | 2-[(E)-(2-{2-[2-fluoro-6-(trifluoromethyl)phenyl]acetyl}hydrazono)-methyl]phenyl 4-(trifluoromethyl)benzenesulfonate; |
| 34. | 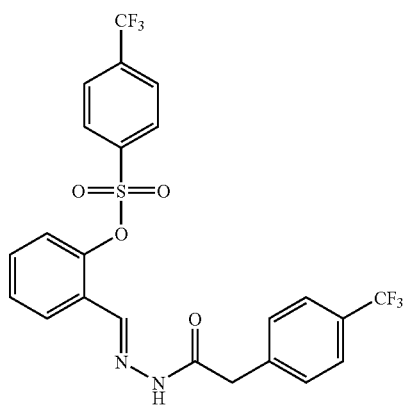 | 2-[(E)-(2-{2-[4-(trifluoromethyl)phenyl]acetyl}hydrazono)-methyl]phenyl 4-(trifluoromethyl)benzenesulfonate; |
| 35. | 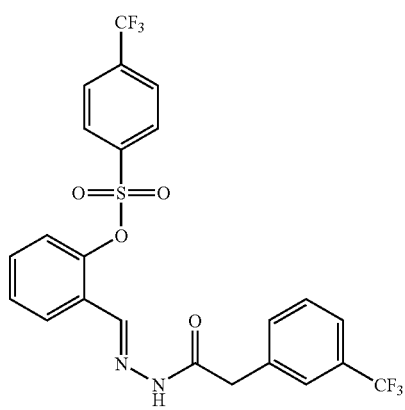 | 2-[(E)-(2-{2-[3-(trifluoromethyl)phenyl]acetyl}hydrazono)-methyl]phenyl 4-(trifluoromethyl)benzenesulfonate; |

TABLE I-continued
| | | |
|---|---|---|
| 36. | 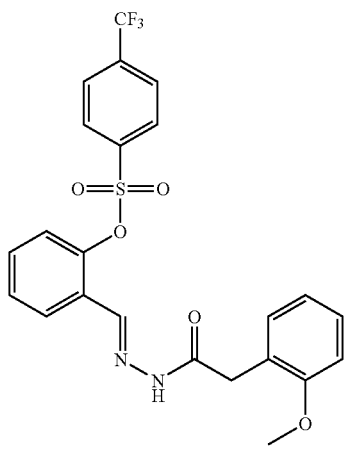 | 2-((E)-{2-[2-(2-methoxyphenyl)acetyl]hydrazono}methyl)-phenyl 4-(trifluoromethyl)benzenesulfonate; |
| 37. | 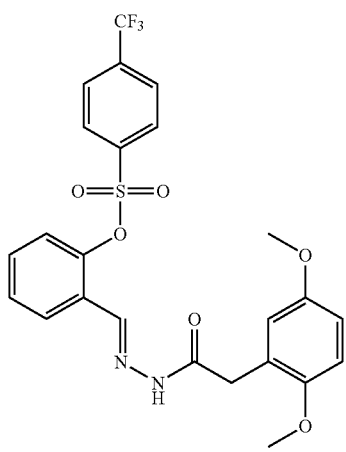 | 2-((E)-{2-[2-(2,5-dimethoxyphenyl)acetyl]hydrazono}methyl)-phenyl 4-(trifluoromethyl)benzenesulfonate; |
| 38. | 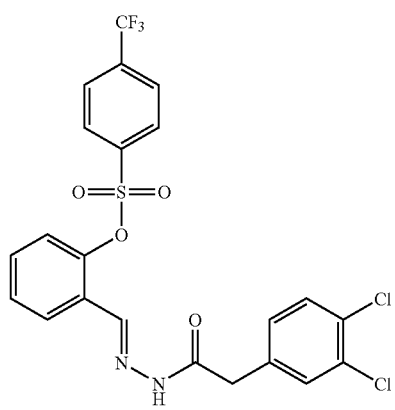 | 2-((E)-{2-[2-(3,4-dichlorophenyl)acetyl]hydrazono}methyl)-phenyl 4-(trifluoromethyl)benzenesulfonate; |

TABLE I-continued
| | | |
|---|---|---|
| 39. | 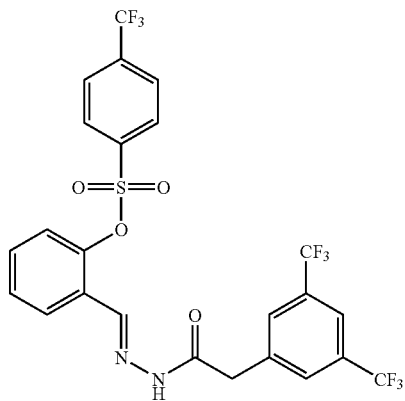 | 2-[(E)-(2-{2-[3,5-bis(trifluoromethyl)phenyl]acetyl}hydrazono)-methyl]phenyl 4-(trifluoromethyl)benzenesulfonate; |
| 40. | 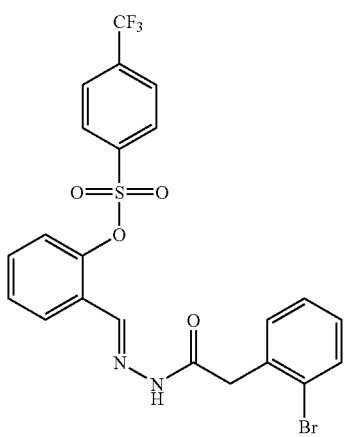 | 2-((E)-{2-[2-(2-bromophenyl)acetyl]hydrazono}methyl)-phenyl 4-(trifluoromethyl)benzenesulfonate; |
| 41. | 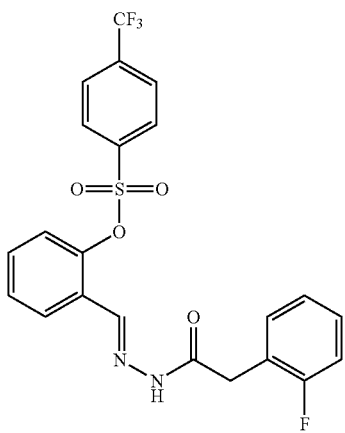 | 2-((E)-{2-[2-(2-fluorophenyl)acetyl]hydrazono}methyl)-phenyl 4-(trifluoromethyl)benzenesulfonate; |

TABLE I-continued
| | | |
|---|---|---|
| 42. | 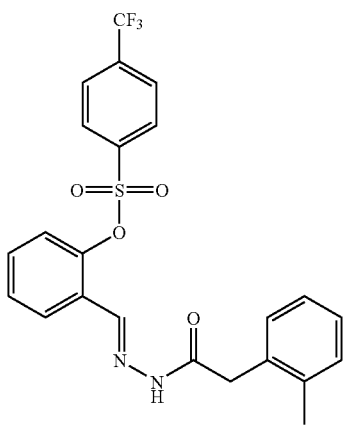 | 2-((E)-{-[2-(2-methylphenyl)acetyl]hydrazono}methyl)-phenyl 4-(trifluoromethyl)benzenesulfonate; |
| 43. | 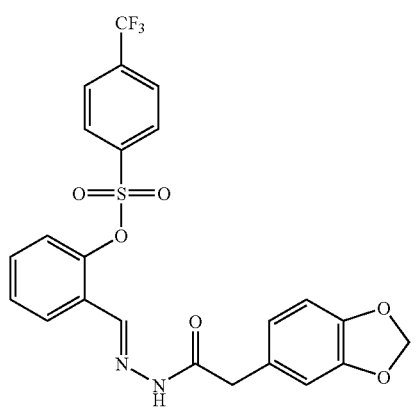 | 2-((E)-{2-[2-(1,3-benzodioxol-5-yl)acetyl]hydrazono}methyl)phenyl 4-(trifluoromethyl)benzenesulfonate; |
| 44. | 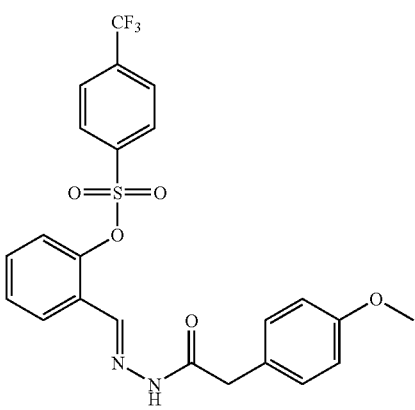 | 2-((E)-{2-[2-(4-methoxyphenyl)acetyl]hydrazono}methyl)-phenyl 4-(trifluoromethyl)benzenesulfonate; |
| 45. | 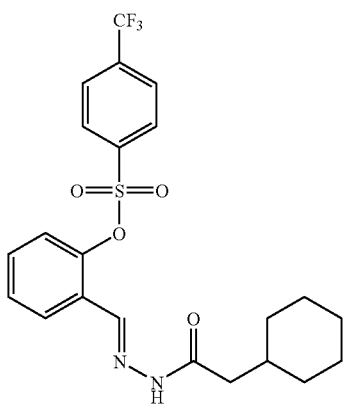 | 2-{(E)-[2-(2-cyclohexylacetyl)hydrazono]methyl}phenyl 4-(trifluoromethyl)benzenesulfonate; |

TABLE I-continued
46. 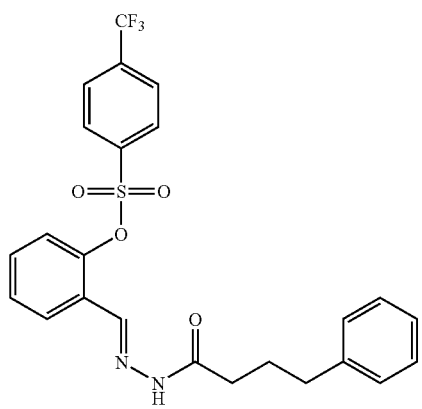 2-{(E)-[2-(4-phenylbutanoyl)hydrazono]methyl}phenyl 4-(trifluoromethyl)benzenesulfonate;
47. 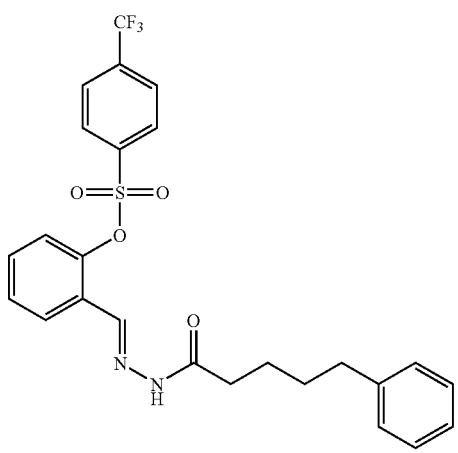 2-{(E)-[2-(5-phenylpentanoyl)hydrazono]methyl}phenyl 4-(trifluoromethyl)benzenesulfonate;
48. 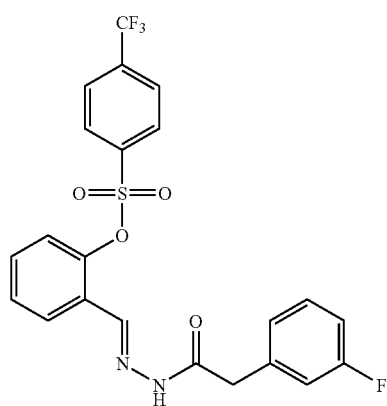 2-((E)-{2-[2-(3-fluorophenyl)acetyl]hydrazono}methyl)-phenyl 4-(trifluoromethyl)benzenesulfonate;

TABLE I-continued
| 49. | 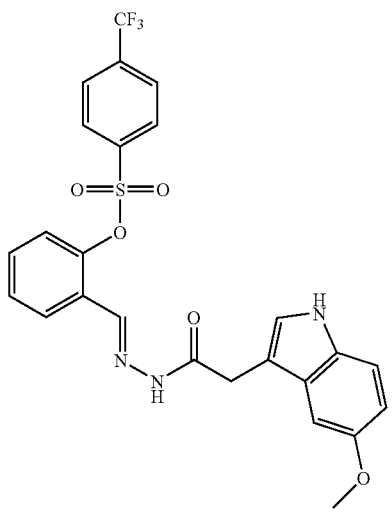 | 2-((E)-{2-[2-(5-methoxy-1H-indol-3-yl)acetyl]hydrazono}methyl)phenyl 4-(trifluoromethyl)benzenesulfonate; |
| --- | --- | --- |
| 50. | 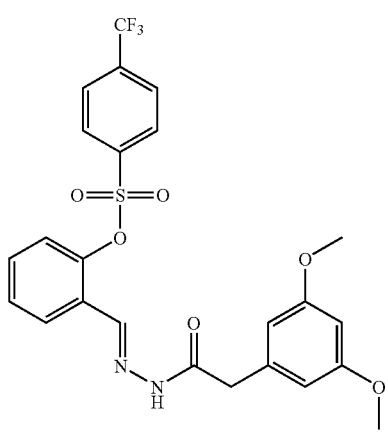 | 2-((E)-{2-[2-(3,5-dimethoxyphenyl)acetyl]hydrazono}methyl)-phenyl 4-(trifluoromethyl)benzenesulfonate; |
| 51. | 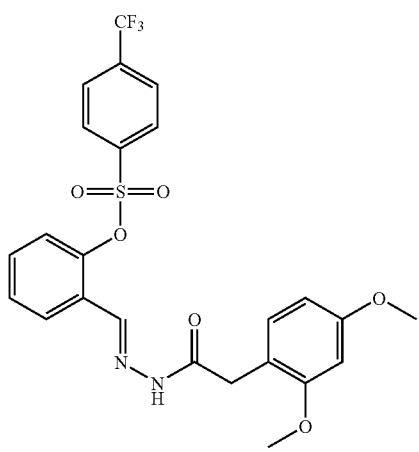 | 2-((E)-{2-[2-(2,4-dimethoxyphenyl)acetyl]hydrazono}methyl)-phenyl 4-(trifluoromethyl)benzenesulfonate; |

TABLE I-continued
| | | |
|---|---|---|
| 52. | 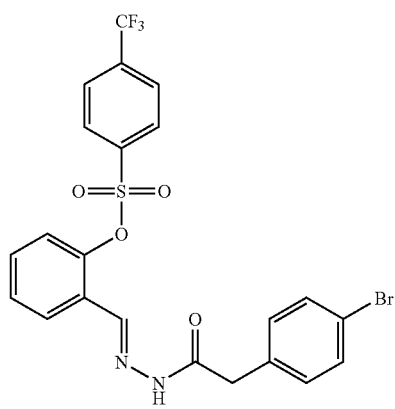 | 2-((E)-{2-[2-(4-bromophenyl)acetyl]hydrazono}methyl)-phenyl 4-(trifluoromethyl)benzenesulfonate; |
| 53. | 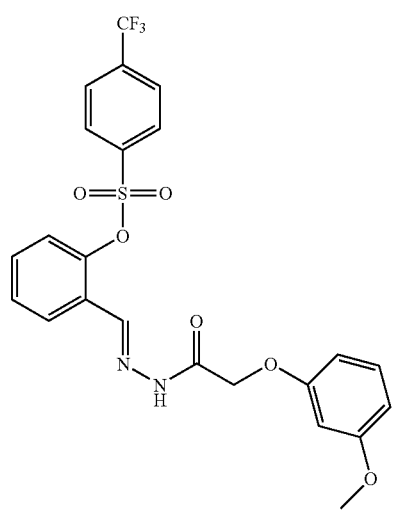 | 2-((E)-{2-[2-(3-methoxyphenoxy)acetyl]hydrazono}methyl)-phenyl 4-(trifluoromethyl)benzenesulfonate; |
| 54. | 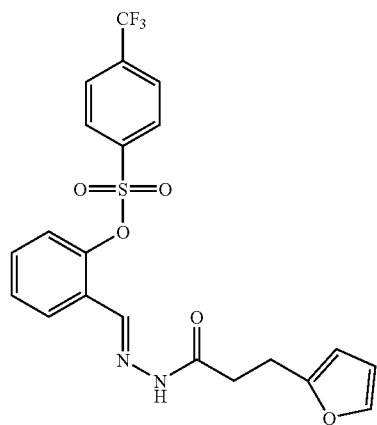 | 2-((E)-{2-[3-(2-furyl)propanoyl]hydrazono}methyl)phenyl 4-(trifluoromethyl)benzenesulfonate; |

TABLE I-continued
| | | |
|---|---|---|
| 55. | 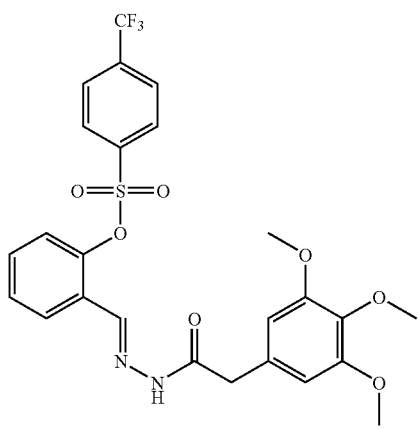 | 2-((E)-{2-[2-(3,4,5-trimethoxyphenyl)acetyl]hydrazono}methyl)-phenyl 4-(trifluoromethyl)benzenesulfonate; |
| 56. | 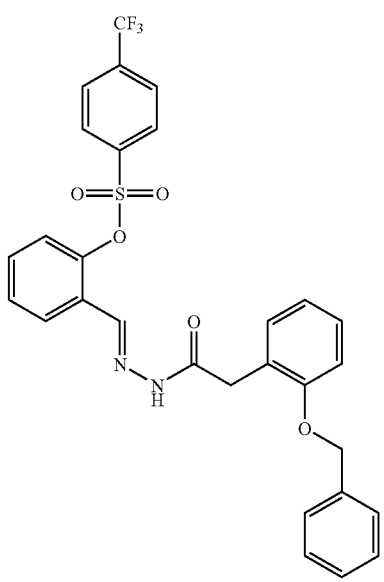 | 2-[(E)-(2-{2-[2-(benzyloxy)phenyl]acetyl}hydrazono)methyl]-phenyl 4-(trifluoromethyl)benzenesulfonate; |
| 57. | 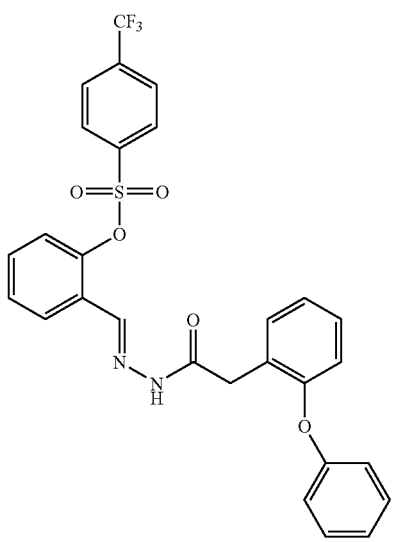 | 2-((E)-{2-[2-(2-phenoxyphenyl)acetyl]hydrazono}methyl)-phenyl 4-(trifluoromethyl)benzenesulfonate; |

TABLE I-continued
| | | |
|---|---|---|
| 58. | 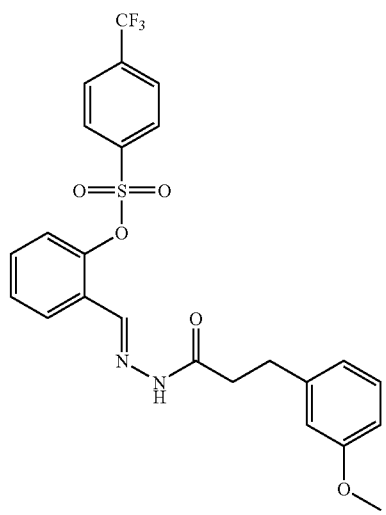 | 2-((E)-{2-[3-(3-methoxyphenyl)propanoyl]hydrazono}-methyl)phenyl 4-(trifluoromethyl)benzenesulfonate; |
| 59. | 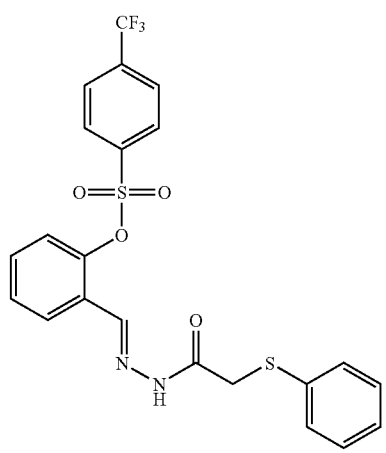 | 2-((E)-{2-[2-(phenylthio)acetyl]hydrazono}methyl)-phenyl 4-(trifluoromethyl)benzenesulfonate; |
| 60. | 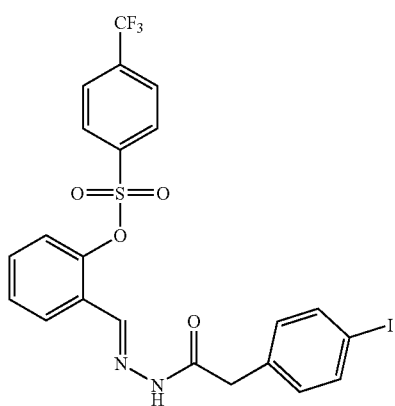 | 2-((E)-{2-[2-(4-iodophenyl)acetyl]hydrazono}methyl)-phenyl 4-(trifluoromethyl)benzenesulfonate; |

TABLE I-continued
| | | |
|---|---|---|
| 61. | 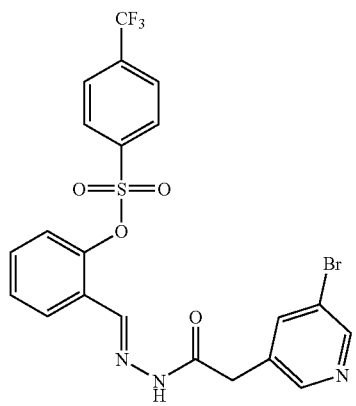 | 2-((E)-{2-[2-(5-bromopyridin-3-yl)acetyl]hydrazono}methyl)phenyl 4-(trifluoromethyl)benzenesulfonate; |
| 62. | 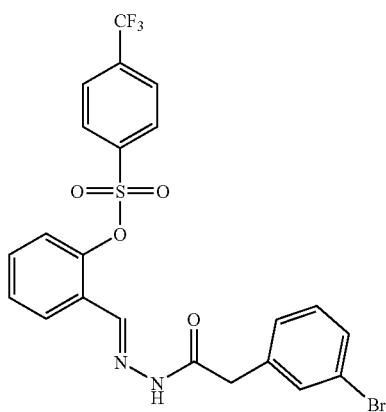 | 2-((E)-{2-[2-(3-bromophenyl)acetyl]hydrazono}methyl)-phenyl 4-(trifluoromethyl)benzenesulfonate; |
| 63. | 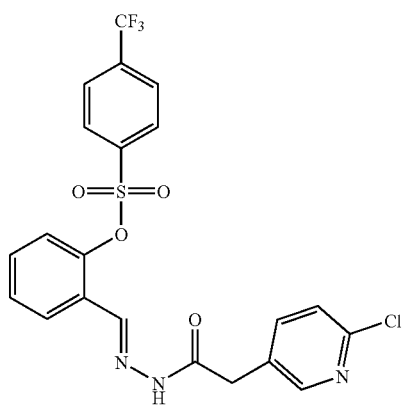 | 2-((E)-{2-[2-(6-chloropyridin-3-yl)acetyl]hydrazono}methyl)phenyl 4-(trifluoromethyl)benzenesulfonate; |

TABLE I-continued
| | | |
|---|---|---|
| 64. | 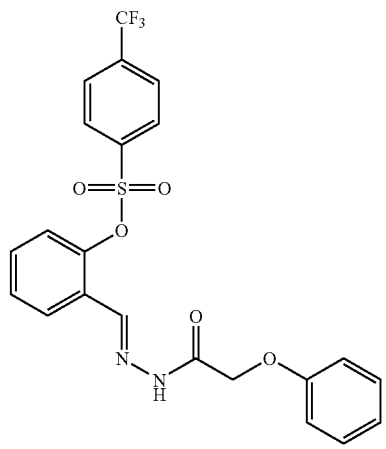 | 2-{(E)-[2-(2-phenoxyacetyl)hydrazono]methyl}phenyl 4-(trifluoromethyl)benzenesulfonate; |
| 65. | 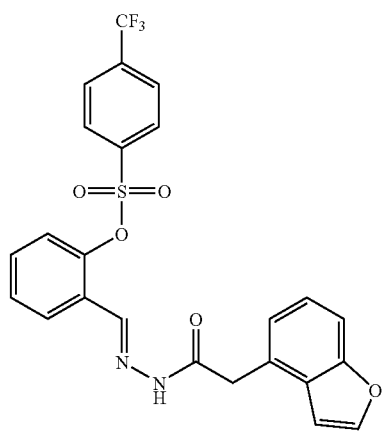 | 2-((E)-{2-[2-(1-benzofuran-4-yl)acetyl]hydrazono}methyl)phenyl 4-(trifluoromethyl)benzenesulfonate; |
| 66. | 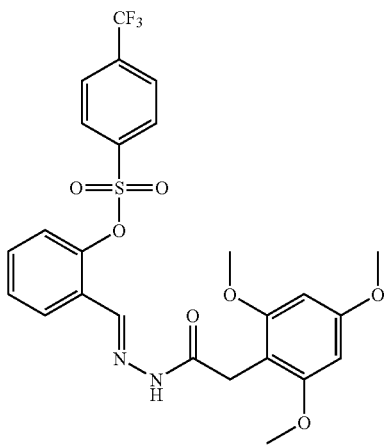 | 2-((E)-{2-[2-(2,4,6-trimethoxyphenyl)acetyl]hydrazono}methyl)-phenyl 4-(trifluoromethyl)benzenesulfonate; |

TABLE I-continued

| | | |
|---|---|---|
| 67. | [structure] | 2-((E)-{2-[2-(4-ethoxyphenyl)acetyl]hydrazono}methyl)-phenyl 4-(trifluoromethyl)benzenesulfonate; |
| 68. | [structure] | 2-((E)-{2-[2-(2-naphthyl)acetyl]hydrazono}methyl)phenyl 4-(trifluoromethyl)benzenesulfonate; |
| 69. | [structure] | 2-[(E)-(2-{2-[4-(methylsulfonyl)phenyl]acetyl}hydrazono)-methyl]phenyl 4-(trifluoromethyl)benzenesulfonate; |
| 70 | [structure] | 2-((E)-{2-[2-(3-bromo-4-methoxyphenyl)acetyl]hydrazono}methyl)-phenyl 4-(trifluoromethyl)benzenesulfonate; |

TABLE I-continued
| | | |
|---|---|---|
| 71. | 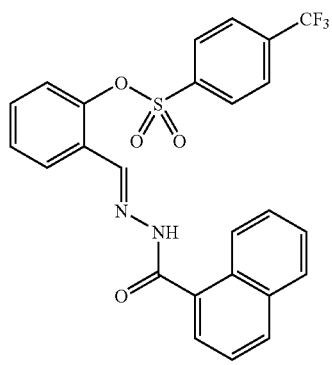 | 2-{(E)-[2-(1-naphthoyl)hydrazono]methyl}phenyl 4-(trifluoromethyl)benzenesulfonate; |
| 72. | 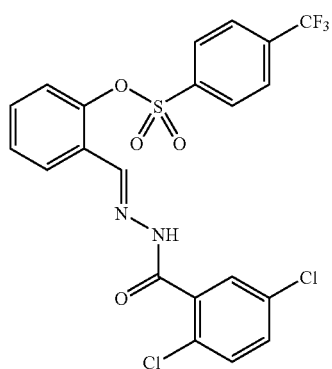 | 2-{(E)-[2-(2,5-dichlorobenzoyl)hydrazono]methyl}phenyl 4-(trifluoromethyl)benzenesulfonate; |
| 73. | 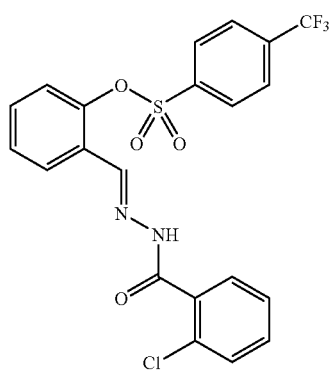 | 2-{(E)-[2-(2-chlorobenzoyl)hydrazono]methyl}phenyl 4-(trifluoromethyl)benzenesulfonate; |
| 74. | 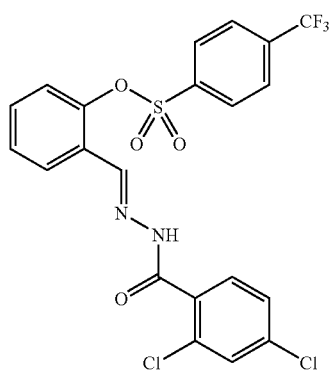 | 2-{(E)-[2-(2,4-dichlorobenzoyl)hydrazono]methyl}phenyl 4-(trifluoromethyl)benzenesulfonate; |

TABLE I-continued
| | | |
|---|---|---|
| 75. | 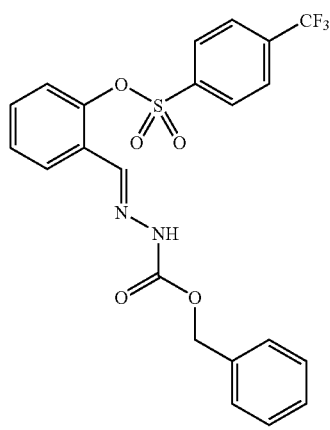 | benzyl (2E)-2-[2-({[4-(trifluoromethyl)phenyl]sulfonyl}oxy)-benzylidene]hydrazinecarboxylate; |
| 76. | 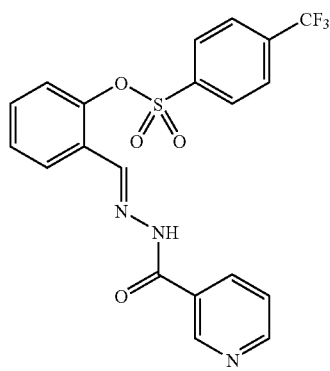 | 2-{(E)-[2-(pyridin-3-ylcarbonyl)hydrazono]methyl}phenyl 4-(trifluoromethyl)benzenesulfonate; |
| 77. | 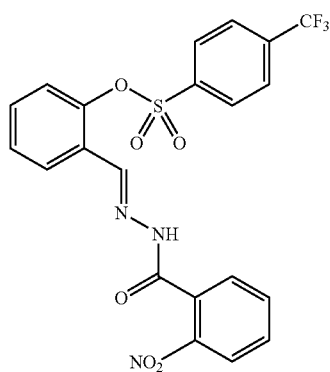 | 2-{(E)-[2-(2-nitrobenzoyl)hydrazono]methyl}phenyl 4-(trifluoromethyl)benzenesulfonate; |
| 78. | 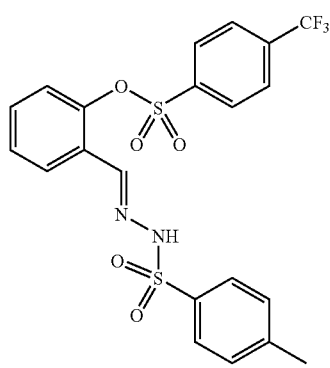 | 2-((E)-{2-[(4-methylphenyl)sulfonyl]hydrazono}methyl)-phenyl 4-(trifluoromethyl)benzenesulfonate; |

TABLE I-continued

| | | |
|---|---|---|
| 79. | 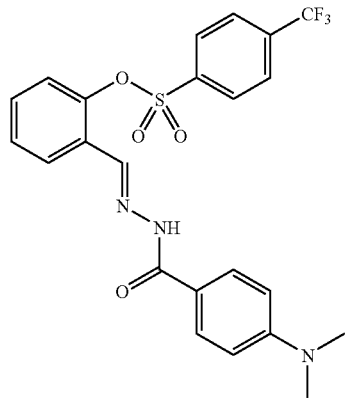 | 2-((E)-{2-[4-(dimethylamino)benzoyl]hydrazono}methyl)-phenyl 4-(trifluoromethyl)benzenesulfonate; |
| 80. | 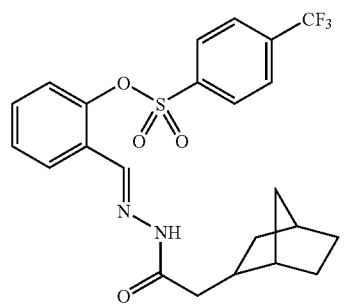 | 2-{(E)-[2-(2-bicyclo[2.2.1]hept-2-ylacetyl)hydrazono]methyl}phenyl 4-(trifluoromethyl)benzenesulfonate; |
| 81. | 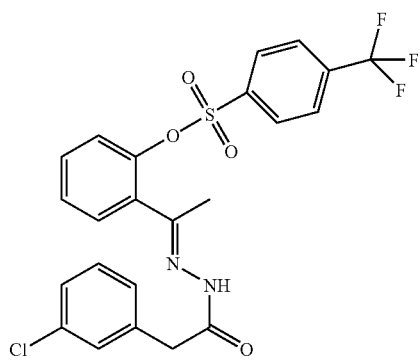 | 2-{(1E)-N-[(3-chlorophenyl)acetyl]ethanehydrazonoyl}-phenyl 4-(trifluoromethyl)benzenesulfonate; |
| 82. | 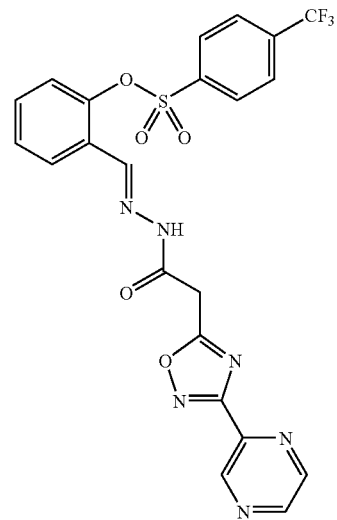 | 2-((E)-{2-[2-(3-pyrazin-2-yl-1,2,4-oxadiazol-5-yl)acetyl]hydrazono}methyl)phenyl 4-(trifluoromethyl)benzenesulfonate; |

TABLE I-continued

| | | |
|---|---|---|
| 83. | 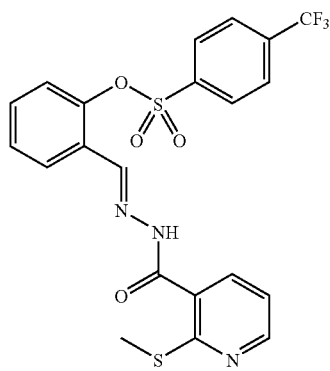 | 2-[(E)-(2-{[2-(methylthio)pyridin-3-yl]carbonyl}hydrazono)methyl]phenyl 4-(trifluoromethyl)benzenesulfonate; |
| 84. | 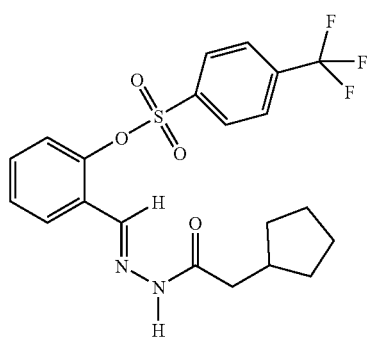 | 2-{(E)-[2-(2-cyclopentylacetyl)hydrazono]methyl}phenyl 4-(trifluoromethyl)benzenesulfonate; |
| 85. | 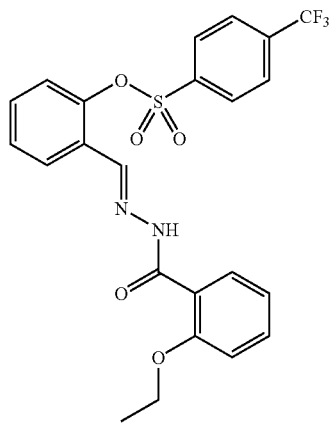 | 2-{(E)-[2-(2-ethoxybenzoyl)hydrazono]methyl}phenyl 4-(trifluoromethyl)benzenesulfonate; |
| 86. | 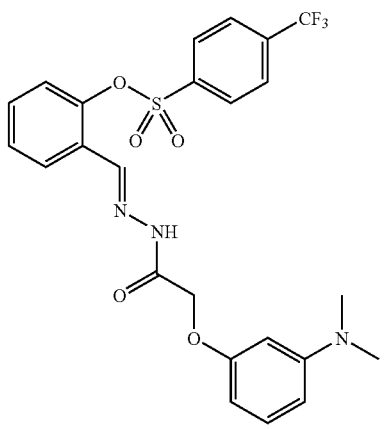<br>Molecular Weight = 521.523O5S | 2-[(E)-(2-{2-[3-(dimethylamino)phenoxy]acetyl}hydrazono)-methyl]phenyl 4-(trifluoromethyl)benzenesulfonate; |

TABLE I-continued
| 87. | 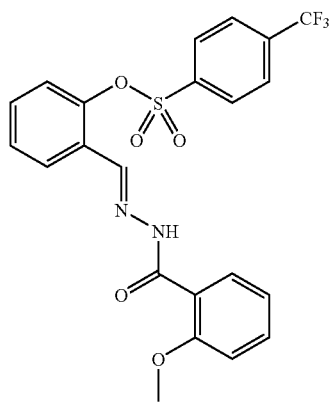 | 2-{(E)-[2-(2-methoxybenzoyl)hydrazono]methyl}phenyl 4-(trifluoromethyl)benzenesulfonate; |
| 88. | 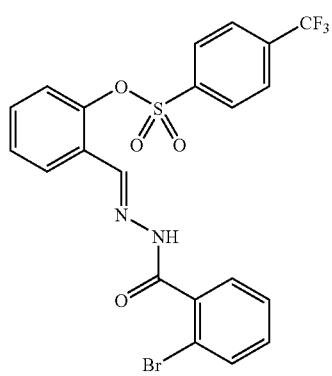 | 2-{(E)-[2-(2-bromobenzoyl)hydrazono]methyl}phenyl 4-(trifluoromethyl)benzenesulfonate; |
| 89. | 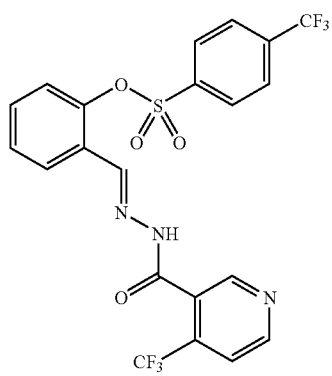 | 2-[(E)-(2-{[4-(trifluoromethyl)pyridin-3-yl]carbonyl}hydrazono)methyl]phenyl 4-(trifluoromethyl)benzenesulfonate; |
| 90. | 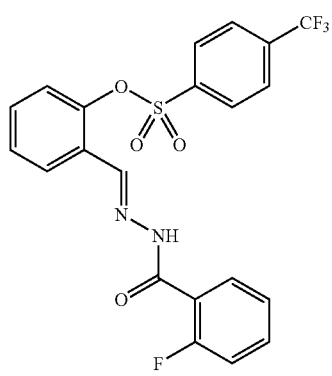 | 2-{(E)-[2-(2-fluorobenzoyl)hydrazono]methyl}phenyl 4-(trifluoromethyl)benzenesulfonate; |

TABLE I-continued

| 91. | 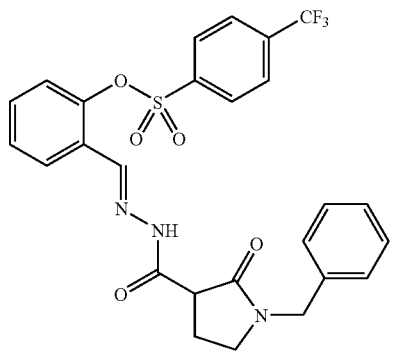 | 2-((E)-{2-[(1-benzyl-2-oxopyrrolidin-3-yl)carbonyl]hydrazono}methyl)phenyl 4-(trifluoromethyl)benzenesulfonate; |
| 92. | 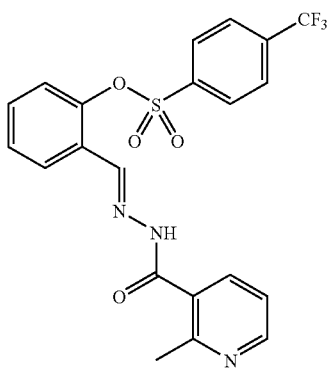 | 2-((E)-{2-[(2-methylpyridin-3-yl)carbonyl]hydrazono}methyl)phenyl 4-(trifluoromethyl)benzenesulfonate; |
| 93. | 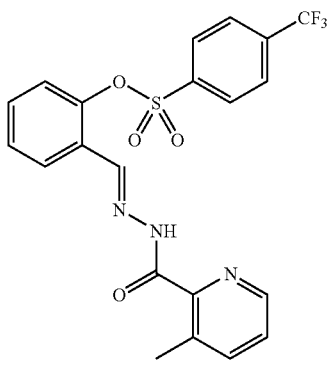 | 2-((E)-{2-[(3-methylpyridin-2-yl)carbonyl]hydrazono}methyl)phenyl 4-(trifluoromethyl)benzenesulfonate; |
| 94. | 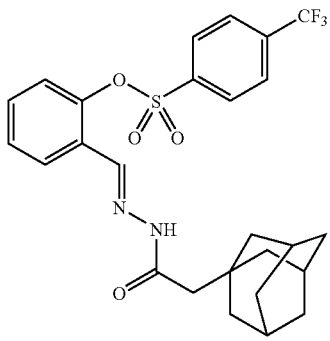 | 2-((E)-{2-[2-(1-adamantyl)acetyl]hydrazono}methyl)phenyl 4-(trifluoromethyl)benzenesulfonate; |

TABLE I-continued
| 95 | 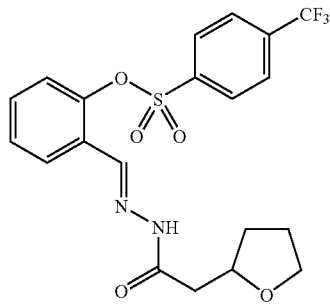 | 2-{(E)-[2-(2-tetrahydrofuran-2-ylacetyl)hydrazono]methyl}phenyl 4-(trifluoromethyl)benzenesulfonate; |
| --- | --- | --- |
| 96. | 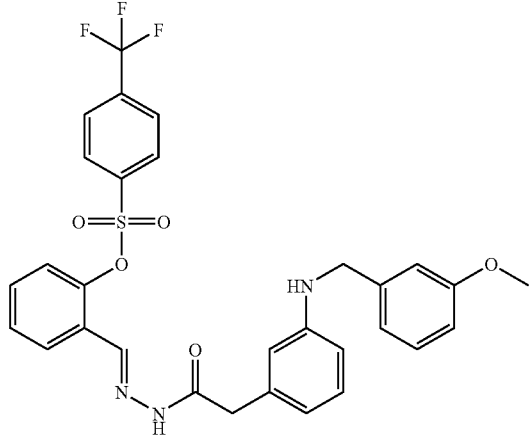 | 2-{(E)-[2-(2-{3-[(3-methoxybenzyl)amino]phenyl}acetyl)hydrazono]methyl}phenyl 4-(trifluoromethyl)benzenesulfonate; |
| 97. | 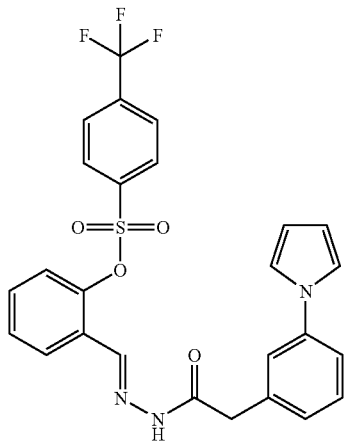 | 2-[(E)-(2-{2-[3-(1H-pyrrol-1-yl)phenyl]acetyl}hydrazono)methyl]phenyl 4-(trifluoromethyl)benzenesulfonate |

TABLE I-continued

| | | |
|---|---|---|
| 98. | 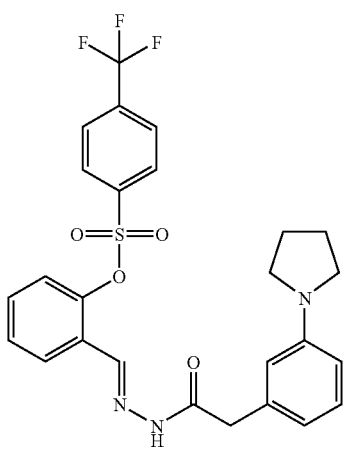 | 2-((E)-{2-[2-(3-pyrrolidin-1-ylphenyl)acetyl]hydrazono}methyl)phenyl 4-(trifluoromethyl)benzenesulfonate |
| 99. | 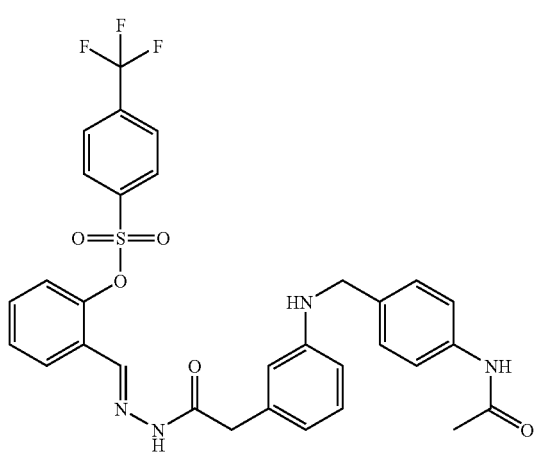 | 2-((E)-{2-[2-(3-{[4-(acetylamino)benzyl]amino}phenyl)acetyl]-hydrazono}methyl)phenyl 4-(trifluoromethyl)benzenesulfonate |
| 100. | 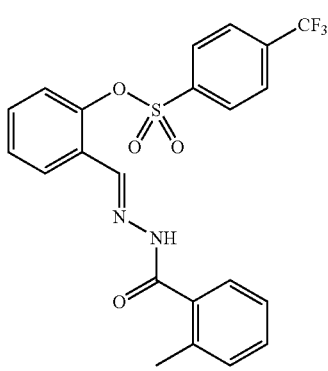 | 2-{(E)-[2-(2-methylbenzoyl)hydrazono]methyl}phenyl 4-(trifluoromethyl)benzenesulfonate; |
| 101. | 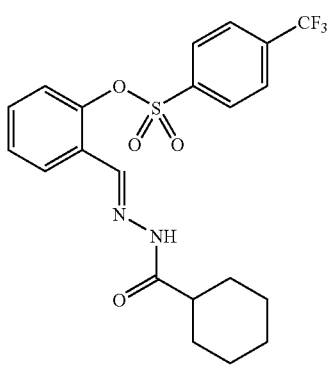 | 2-{(E)-[2-(cyclohexylcarbonyl)hydrazono]methyl}phenyl 4-(trifluoromethyl)benzenesulfonate; |

TABLE I-continued

102. 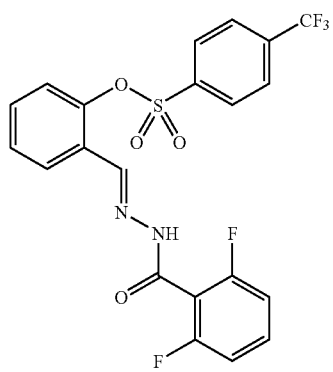
2-{(E)-[2-(2,6-difluorobenzoyl)hydrazono]methyl}phenyl 4-(trifluoromethyl)benzenesulfonate;

103. 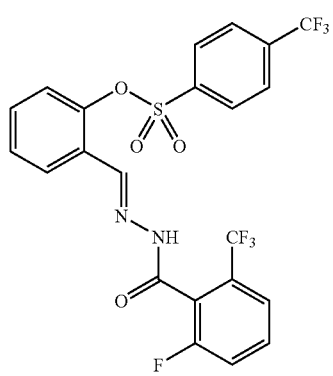
2-((E)-{2-[2-fluoro-6-(trifluoromethyl)benzoyl]hydrazono}methyl)-phenyl 4-(trifluoromethyl)benzenesulfonate;

104. 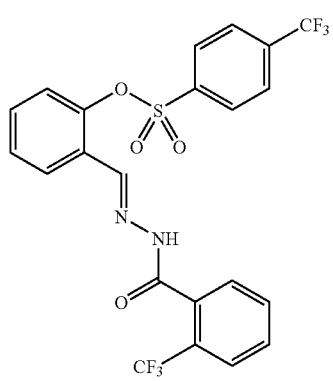
2-((E)-{2-[2-(trifluoromethyl)benzoyl]hydrazono}methyl)-phenyl 4-(trifluoromethyl)benzenesulfonate;

105. 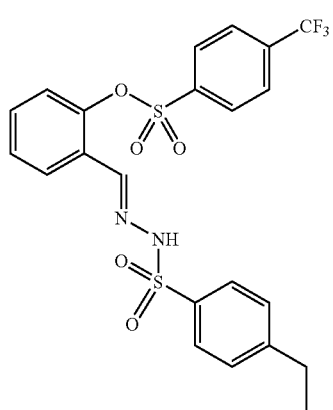
2-((E)-{2-[(4-ethylphenyl)sulfonyl]hydrazono}methyl)-phenyl 4-(trifluoromethyl)benzenesulfonate;

TABLE I-continued
| | | |
|---|---|---|
| 106. | 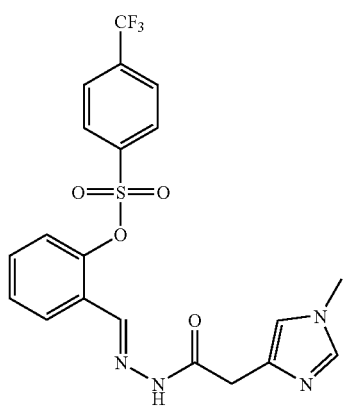 | 2-((E)-{2-[2-(1-methyl-1H-imidazol-4-yl)acetyl]hydrazono}methyl)phenyl 4-(trifluoromethyl)benzenesulfonate; |
| 107. | 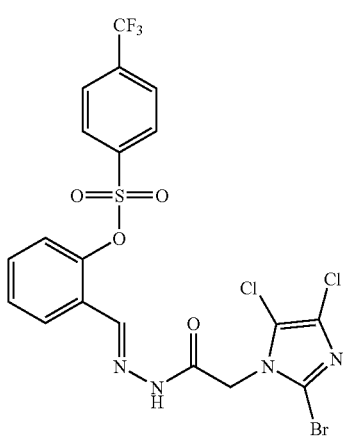 | 2-((E)-{2-[2-(2-bromo-4,5-dichloro-1H-imidazol-1-yl)acetyl]hydrazono}methyl)phenyl 4-(trifluoromethyl)benzenesulfonate; |
| 108. | 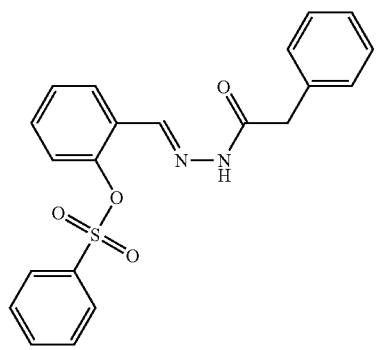 | 2-{(E)-[2-(2-phenylacetyl)hydrazono]methyl}phenyl benzenesulfonate; |
| 109. | 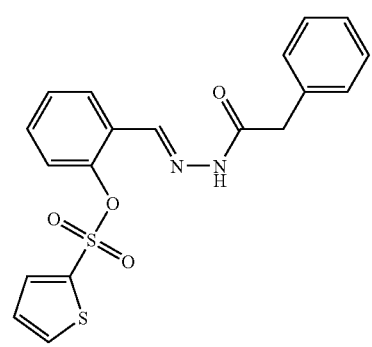 | 2-{(E)-[2-(2-phenylacetyl)hydrazono]methyl}phenyl thiophene-2-sulfonate; |

TABLE I-continued
| | | |
|---|---|---|
| 110. | 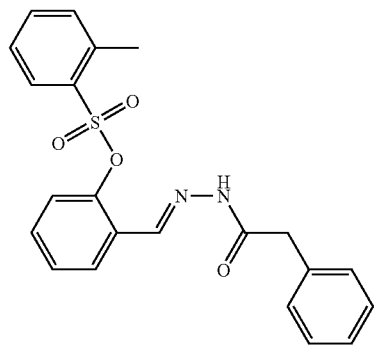 | 2-{(E)-[2-(2-phenylacetyl)hydrazono]methyl}phenyl 2-methylbenzenesulfonate; |
| 111. | 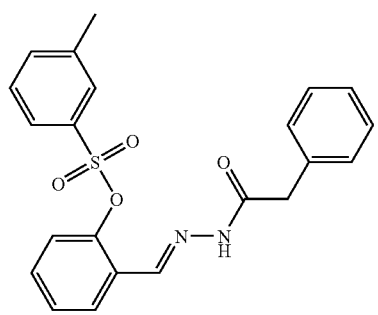 | 2-{(E)-[2-(2-phenylacetyl)hydrazono]methyl}phenyl 3-methylbenzenesulfonate; |
| 112. | 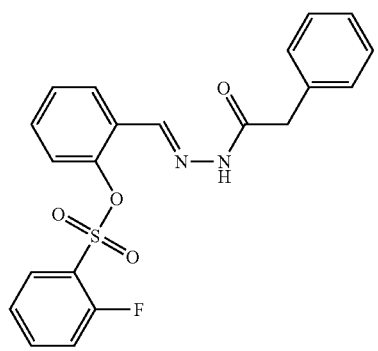 | 2-{(E)-[2-(2-phenylacetyl)hydrazono]methyl}phenyl 2-fluorobenzenesulfonate; |
| 113. | 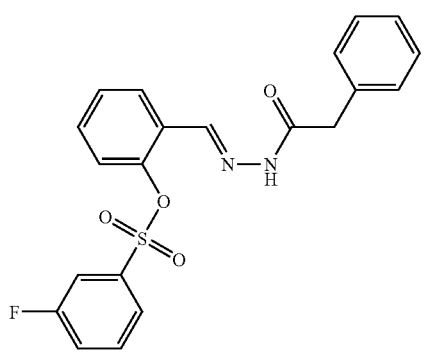 | 2-{(E)-[2-(2-phenylacetyl)hydrazono]methyl}phenyl 3-fluorobenzenesulfonate; |

TABLE I-continued
| | | |
|---|---|---|
| 114. | 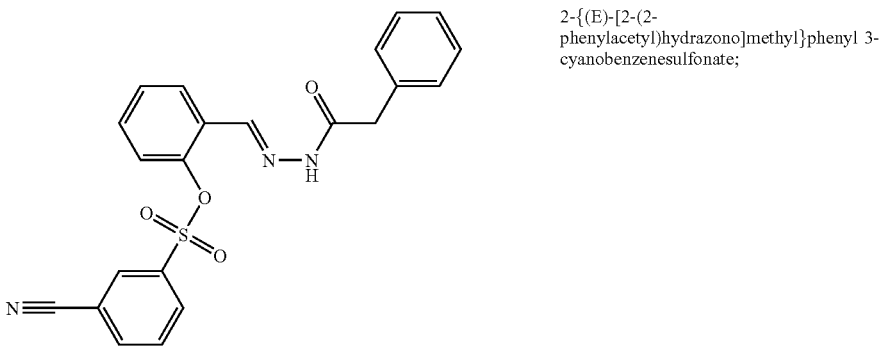 | 2-{(E)-[2-(2-phenylacetyl)hydrazono]methyl}phenyl 3-cyanobenzenesulfonate; |
| 115. | 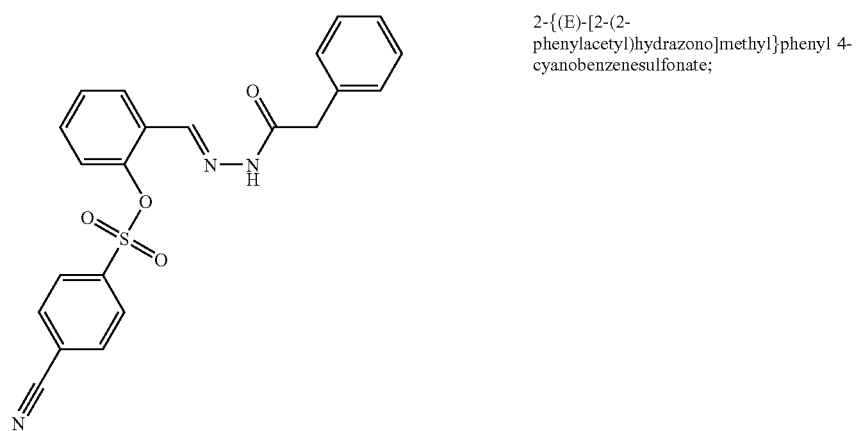 | 2-{(E)-[2-(2-phenylacetyl)hydrazono]methyl}phenyl 4-cyanobenzenesulfonate; |
| 116. | 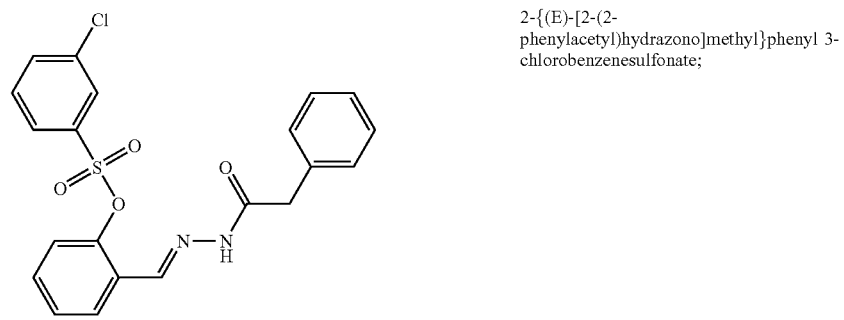 | 2-{(E)-[2-(2-phenylacetyl)hydrazono]methyl}phenyl 3-chlorobenzenesulfonate; |
| 117. | 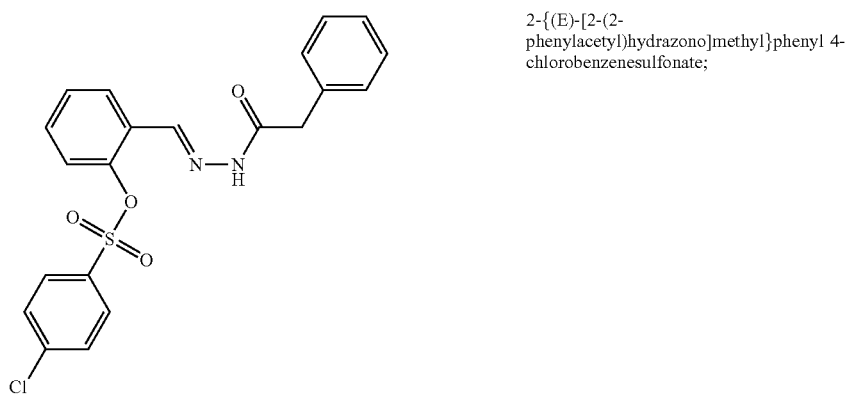 | 2-{(E)-[2-(2-phenylacetyl)hydrazono]methyl}phenyl 4-chlorobenzenesulfonate; |

TABLE I-continued
| | | |
|---|---|---|
| 118. | 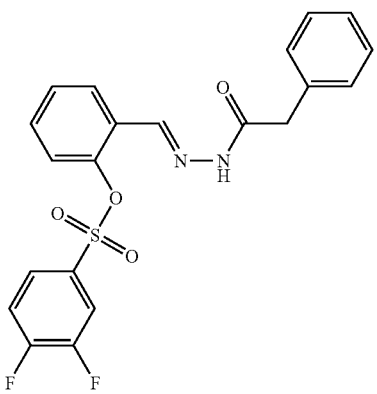 | 2-{(E)-[2-(2-phenylacetyl)hydrazono]methyl}phenyl 3,4-difluorobenzenesulfonate; |
| 119. | 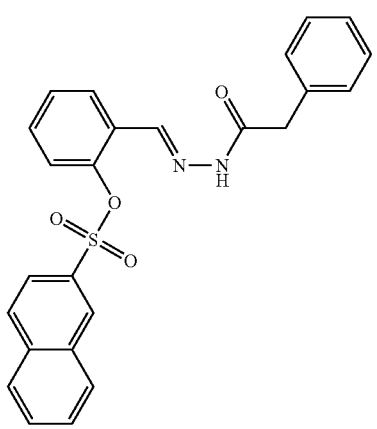 | 2-{(E)-[2-(2-phenylacetyl)hydrazono]methyl}phenyl naphthalene-2-sulfonate; |
| 120. | 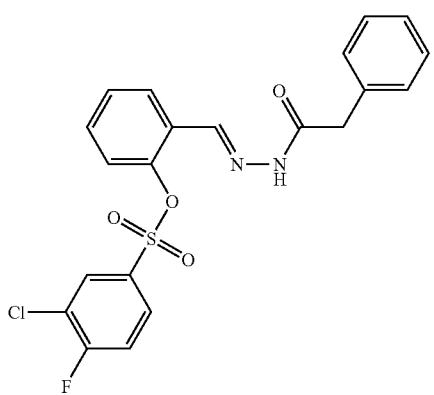 | 2-{(E)-[2-(2-phenylacetyl)hydrazono]methyl}phenyl 3-chloro-4-fluorobenzenesulfonate; |
| 121. | 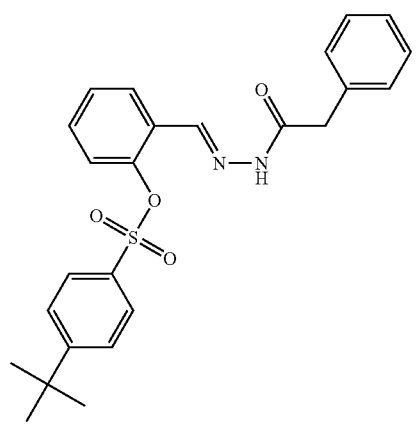 | 2-{(E)-[2-(2-phenylacetyl)hydrazono]methyl}phenyl 4-tert-butylbenzenesulfonate; |

TABLE I-continued
| 122. | 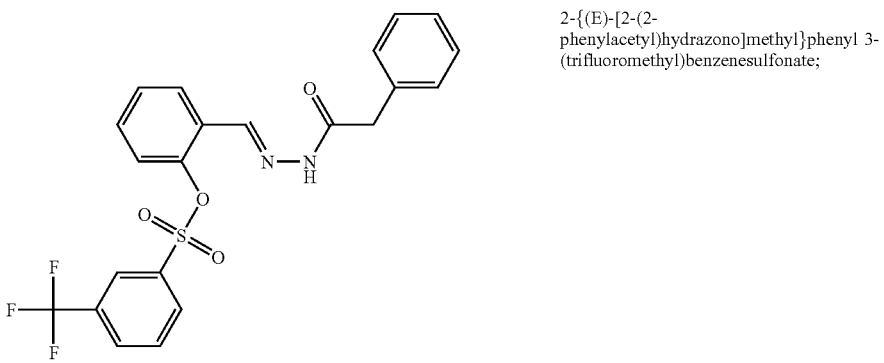 | 2-{(E)-[2-(2-phenylacetyl)hydrazono]methyl}phenyl 3-(trifluoromethyl)benzenesulfonate; |
| 123. | 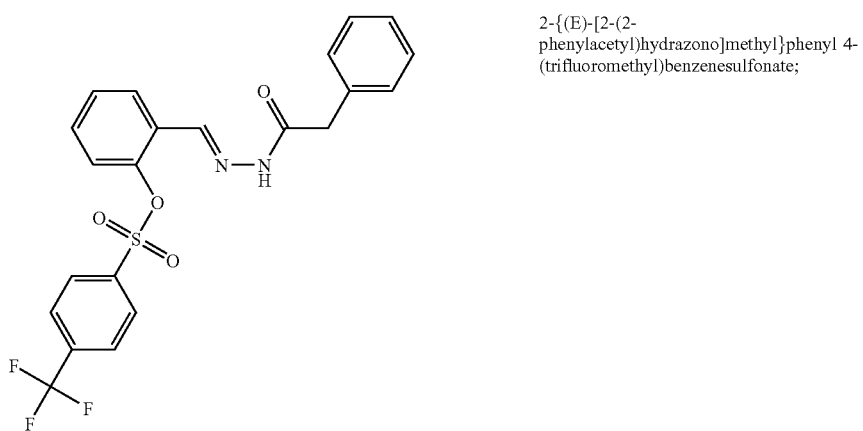 | 2-{(E)-[2-(2-phenylacetyl)hydrazono]methyl}phenyl 4-(trifluoromethyl)benzenesulfonate; |
| 124. | 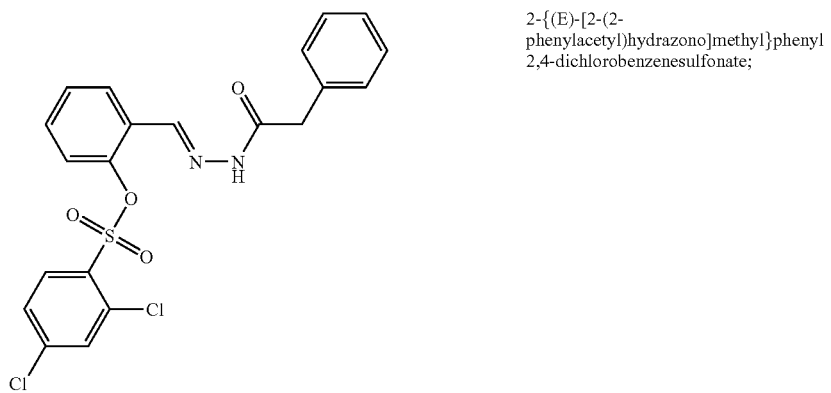 | 2-{(E)-[2-(2-phenylacetyl)hydrazono]methyl}phenyl 2,4-dichlorobenzenesulfonate; |
| 125. | 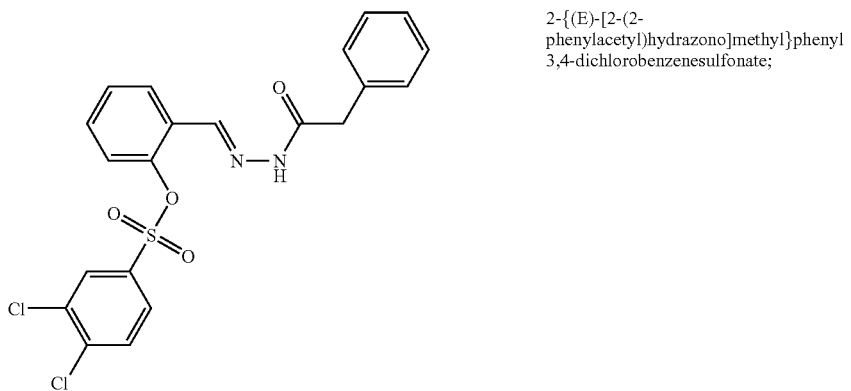 | 2-{(E)-[2-(2-phenylacetyl)hydrazono]methyl}phenyl 3,4-dichlorobenzenesulfonate; |

TABLE I-continued
| 126. | 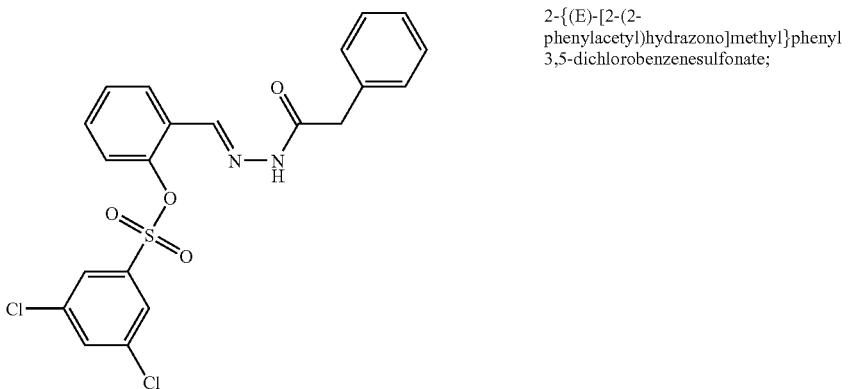 | 2-{(E)-[2-(2-phenylacetyl)hydrazono]methyl}phenyl 3,5-dichlorobenzenesulfonate; |
| --- | --- | --- |
| 127. | 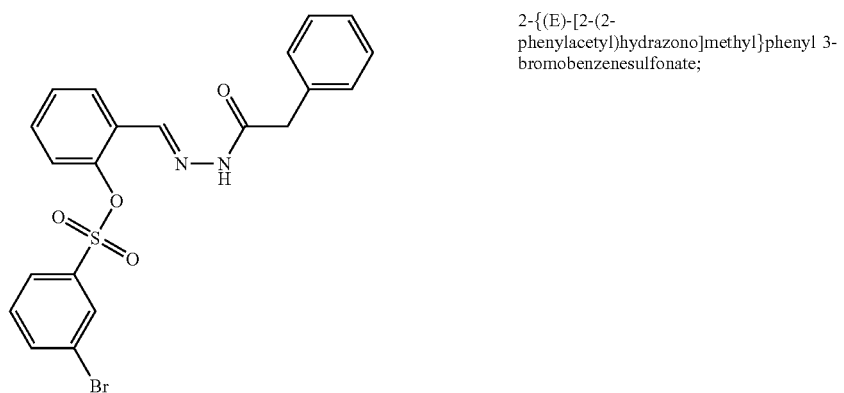 | 2-{(E)-[2-(2-phenylacetyl)hydrazono]methyl}phenyl 3-bromobenzenesulfonate; |
| 128. | 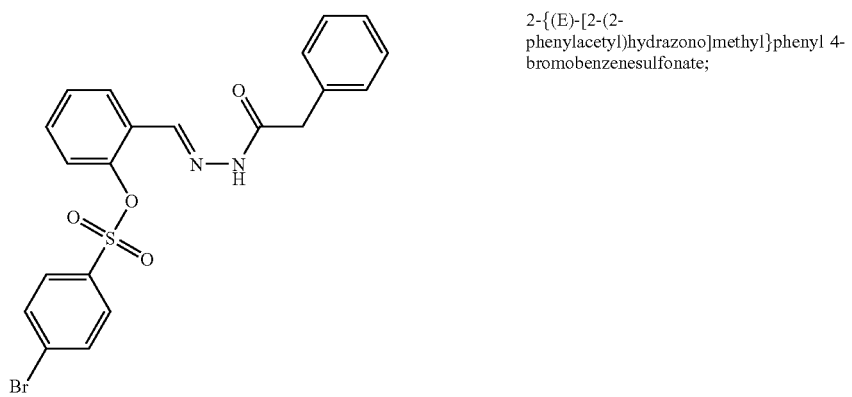 | 2-{(E)-[2-(2-phenylacetyl)hydrazono]methyl}phenyl 4-bromobenzenesulfonate; |
| 129. | 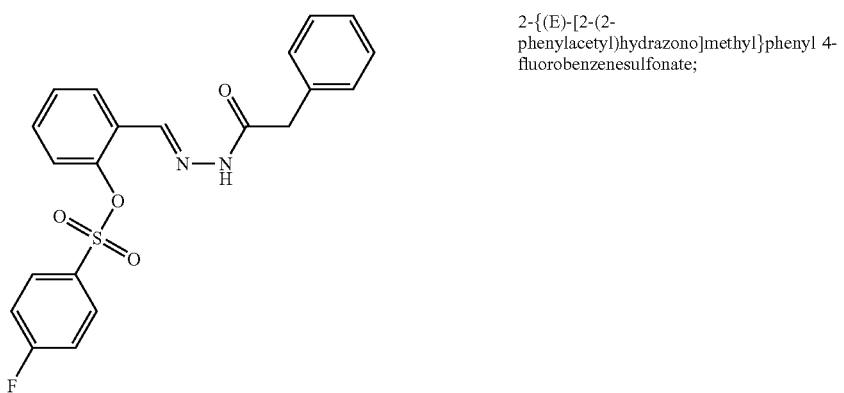 | 2-{(E)-[2-(2-phenylacetyl)hydrazono]methyl}phenyl 4-fluorobenzenesulfonate; |

TABLE I-continued
| 130. | 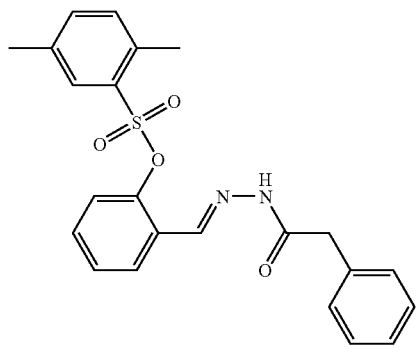 | 2-{(E)-[2-(2-phenylacetyl)hydrazono]methyl}phenyl 2,5-dimethylbenzenesulfonate; |
| --- | --- | --- |
| 131. | 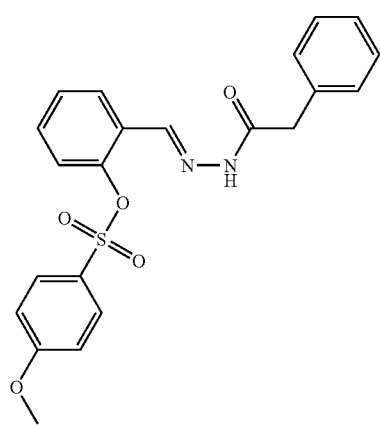 | 2-{(E)-[2-(2-phenylacetyl)hydrazono]methyl}phenyl 4-methoxybenzenesulfonate; |
| 132. | 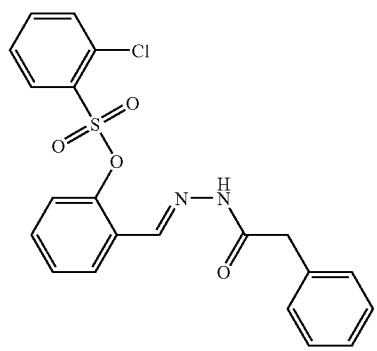 | 2-{(E)-[2-(2-phenylacetyl)hydrazono]methyl}phenyl 2-chlorobenzenesulfonate; |
| 133. | 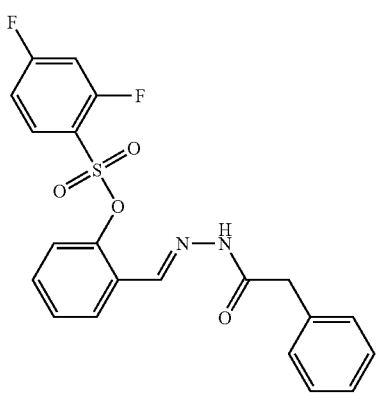 | 2-{(E)-[2-(2-phenylacetyl)hydrazono]methyl}phenyl 2,4-difluorobenzenesulfonate; |

TABLE I-continued
| | | |
|---|---|---|
| 134. | 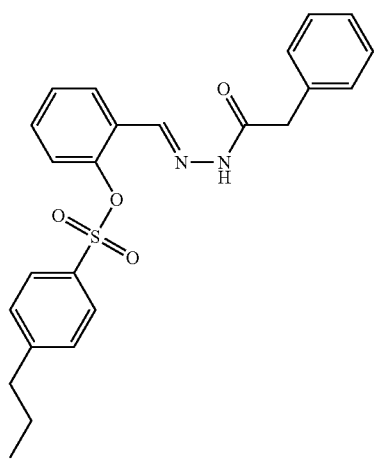 | 2-{(E)-[2-(2-phenylacetyl)hydrazono]methyl}phenyl 4-propylbenzenesulfonate; |
| 135. | 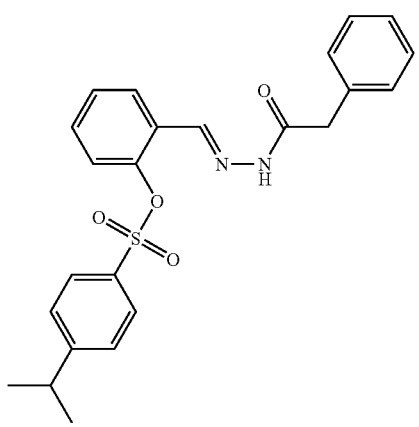 | 2-{(E)-[2-(2-phenylacetyl)hydrazono]methyl}phenyl 4-isopropylbenzenesulfonate; |
| 136. | 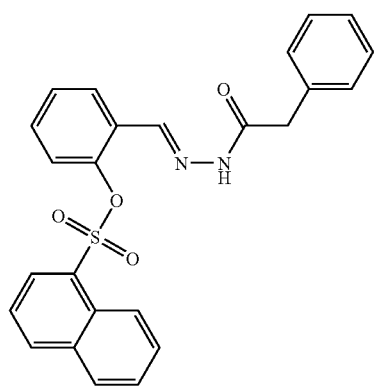 | 2-{(E)-[2-(2-phenylacetyl)hydrazono]methyl}phenyl naphthalene-1-sulfonate; |

TABLE I-continued
| 137. | 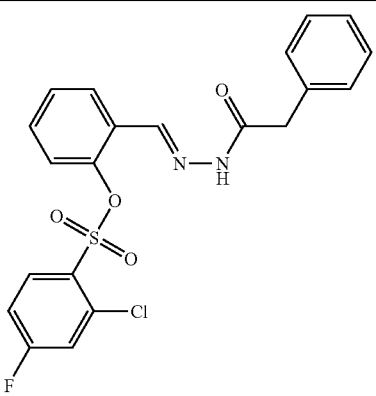 | 2-{(E)-[2-(2-phenylacetyl)hydrazono]methyl}phenyl 2-chloro-4-fluorobenzenesulfonate; |
| 138. | 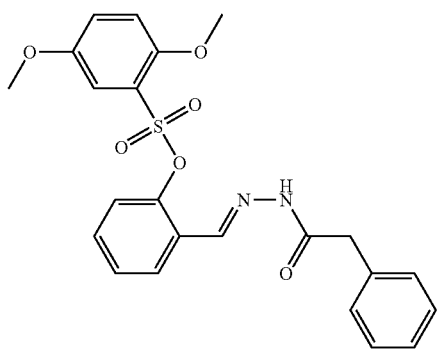 | 2-{(E)-[2-(2-phenylacetyl)hydrazono]methyl}phenyl 2,5-dimethoxybenzenesulfonate; |
| 139. | 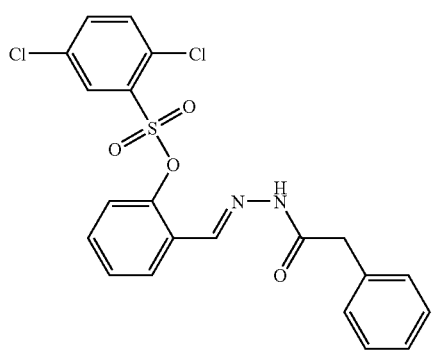 | 2-{(E)-[2-(2-phenylacetyl)hydrazono]methyl}phenyl 2,5-dichlorobenzenesulfonate; |
| 140. | 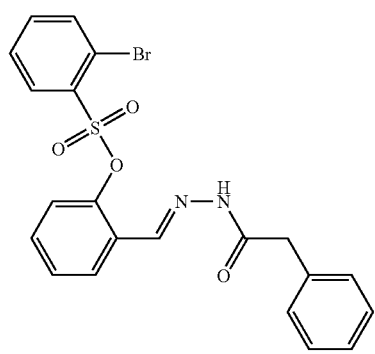 | 2-{(E)-[2-(2-phenylacetyl)hydrazono]methyl}phenyl 2-bromobenzenesulfonate; |

TABLE I-continued
141. 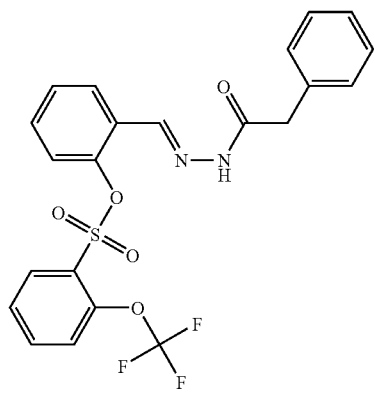 2-{(E)-[2-(2-phenylacetyl)hydrazono]methyl}phenyl 2-(trifluoromethoxy)benzenesulfonate;
142. 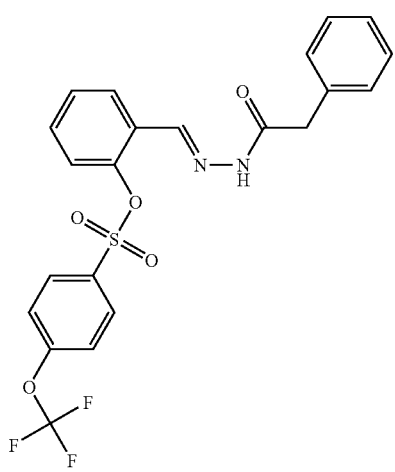 2-{(E)-[2-(2-phenylacetyl)hydrazono]methyl}phenyl 4-(trifluoromethoxy)benzenesulfonate;
143. 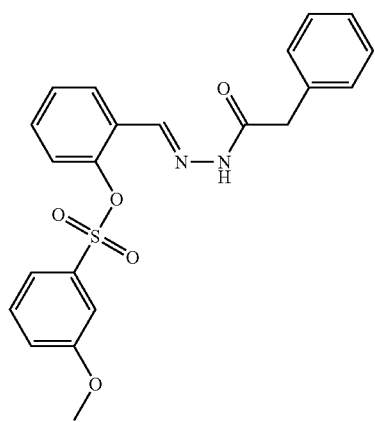 2-{(E)-[2-(2-phenylacetyl)hydrazono]methyl}phenyl 3-methoxybenzenesulfonate;

TABLE I-continued

| | | |
|---|---|---|
| 144. | 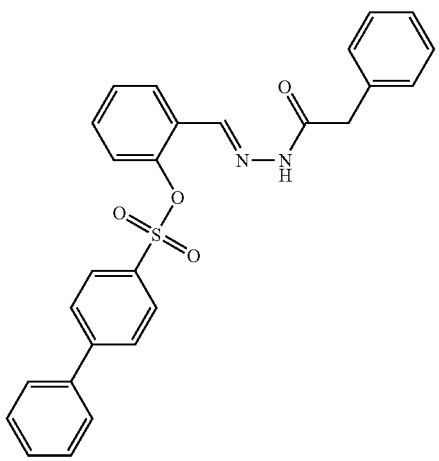 | 2-{(E)-[2-(2-phenylacetyl)hydrazono]methyl}phenyl 1,1'-biphenyl-4-sulfonate; |
| 145. | 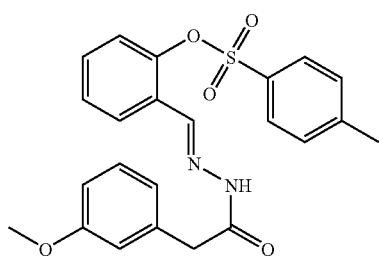 | 2-((E)-{2-[2-(3-methoxyphenyl)acetyl]hydrazono}methyl)-phenyl 4-methylbenzenesulfonate; |
| 146. | 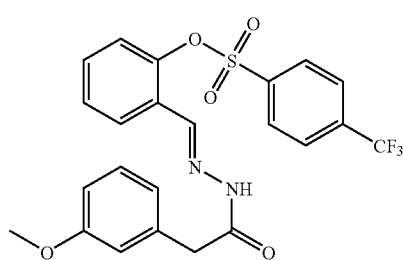 | 2-((E)-{2-[2-(3-methoxyphenyl)acetyl]hydrazono}methyl)-phenyl 4-(trifluoromethyl)benzenesulfonate; |
| 147. | 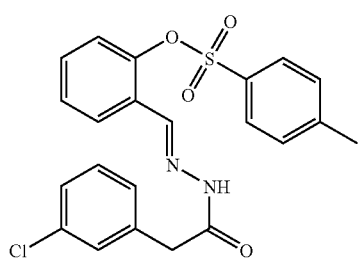 | 2-((E)-{2-[2-(3-chlorophenyl)acetyl]hydrazono}methyl)-phenyl 4-methylbenzenesulfonate; |
| 148. | 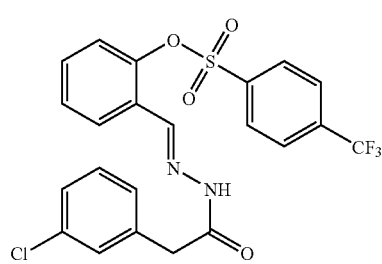 | 2-((E)-{2-[2-(3-chlorophenyl)acetyl]hydrazono}methyl)-phenyl 4-(trifluoromethyl)benzenesulfonate; |

TABLE I-continued

| | | |
|---|---|---|
| 149. | 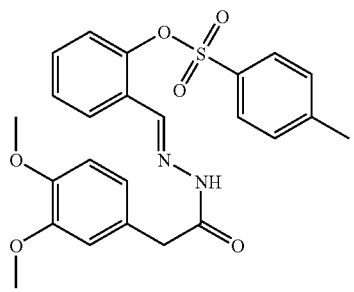 | 2-((E)-{2-[2-(3,4-dimethoxyphenyl)acetyl]hydrazono}methyl)-phenyl 4-methylbenzenesulfonate; |
| 150. | 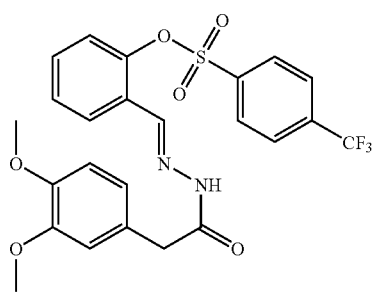 | 2-((E)-{2-[2-(3,4-dimethoxyphenyl)acetyl]hydrazono}methyl)-phenyl 4-(trifluoromethyl)benzenesulfonate; |
| 151. | 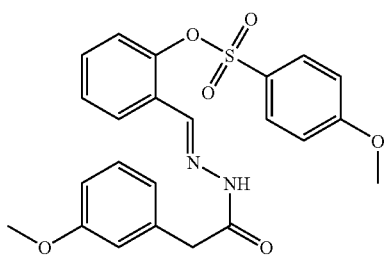 | 2-((E)-{2-[2-(3-methoxyphenyl)acetyl]hydrazono}methyl)-phenyl 4-methoxybenzenesulfonate; |
| 152. | 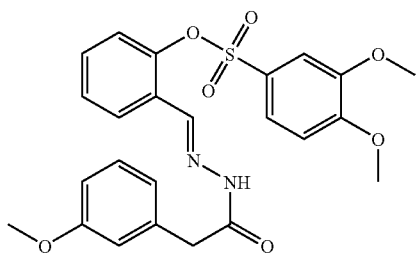 | 2-((E)-{2-[2-(3-methoxyphenyl)acetyl]hydrazono}methyl)-phenyl 3,4-dimethoxybenzenesulfonate; |
| 153. | 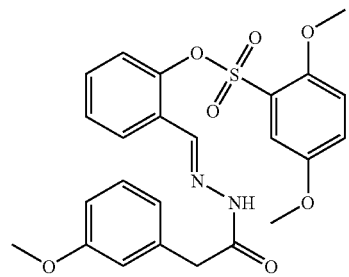 | 2-((E)-{2-[2-(3-methoxyphenyl)acetyl]hydrazono}methyl)-phenyl 2,5-dimethoxybenzenesulfonate; |

TABLE I-continued
154. 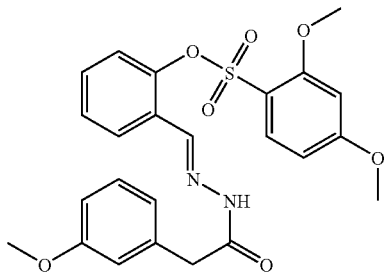
2-((E)-{2-[2-(3-methoxyphenyl)acetyl]hydrazono}methyl)-phenyl 2,4-dimethoxybenzenesulfonate;
155. 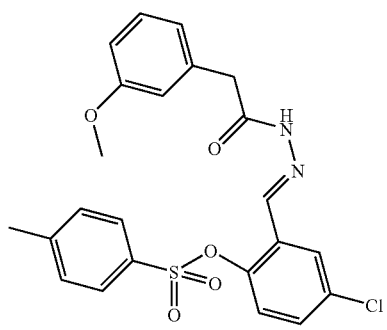
4-chloro-2-((E)-{[(3-methoxyphenyl)acetyl]hydrazono}methyl)-phenyl 4-methylbenzenesulfonate;
156. 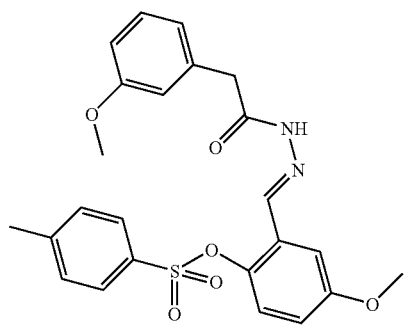
4-methoxy-2-((E)-{[(3-methoxyphenyl)acetyl]hydrazono}methyl)-phenyl 4-methylbenzenesulfonate;
157. 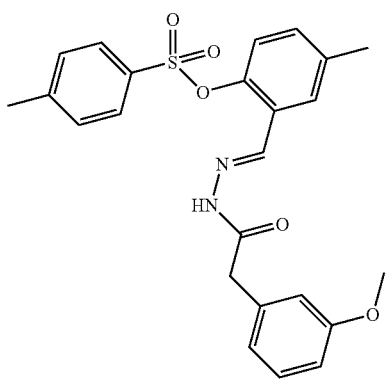
2-((E)-{[(3-methoxyphenyl)acetyl]hydrazono}methyl)-4-methylphenyl 4-methylbenzenesulfonate;

TABLE I-continued
| 158. | 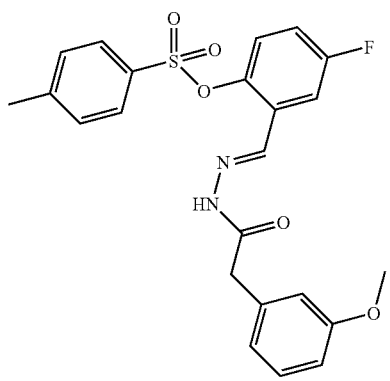 | 4-fluoro-2-((E)-{[(3-methoxyphenyl)acetyl]hydrazono}methyl)-phenyl 4-methylbenzenesulfonate; |
| 159. | 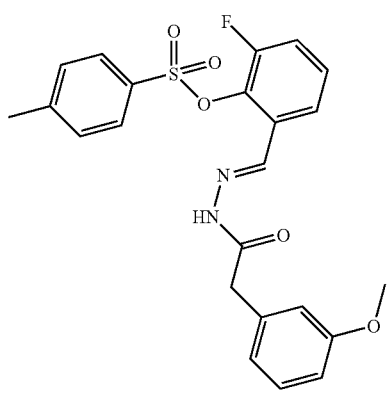 | 3; |
| 160. | 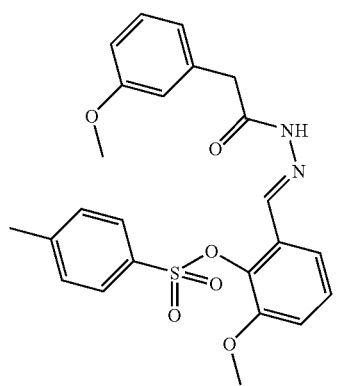 | 2-methoxy-6-((E)-{[(3-methoxyphenyl)acetyl]hydrazono}methyl)-phenyl 4-methylbenzenesulfonate; |
| 161. | 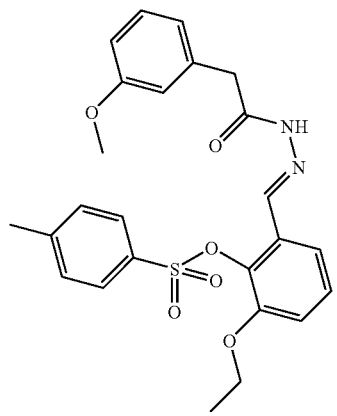 | 2-ethoxy-6-((E)-{[(3-methoxyphenyl)acetyl]hydrazono}methyl)-phenyl 4-methylbenzenesulfonate; |

TABLE I-continued
162. 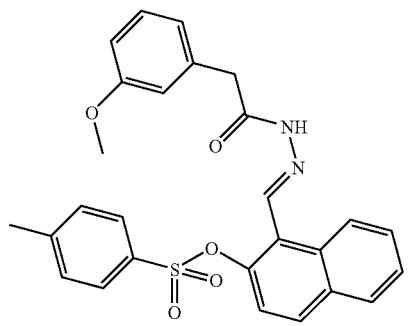 1-((E)-{2-[2-(3-methoxyphenyl)acetyl]hydrazono}methyl)-2-naphthyl 4-methylbenzenesulfonate;
163. 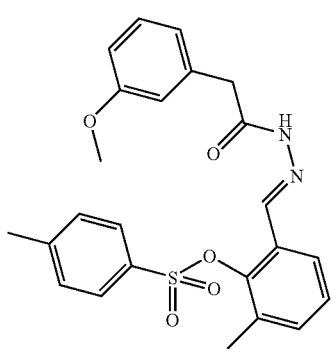 2-((E)-{[(3-methoxyphenyl)acetyl]hydrazono}methyl)-6-methylphenyl 4-methylbenzenesulfonate;
164. 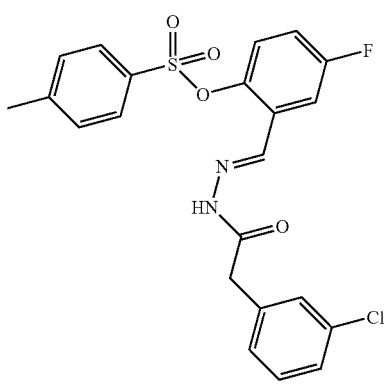 2-((E)-{[(3-chlorophenyl)acetyl]-hydrazono}methyl)-4-fluorophenyl 4-methylbenzenesulfonate;
165. 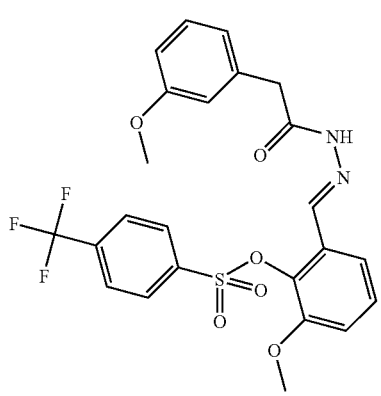 2-methoxy-6-((E)-{[(3-methoxyphenyl)acetyl]hydrazono}methyl)-phenyl 4-(trifluoromethyl)-benzenesulfonate;

TABLE I-continued

| | | |
|---|---|---|
| 166. | 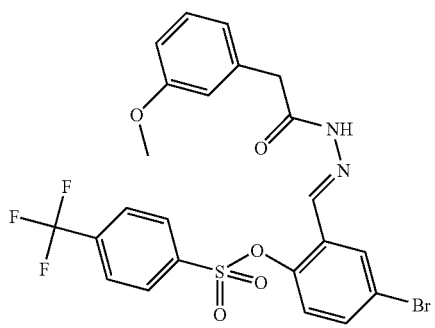 | 4-bromo-2-((E)-{[(3-methoxyphenyl)acetyl]hydrazono}ethyl)-phenyl 4-(trifluoromethyl)benzenesulfonate; |
| 167. | 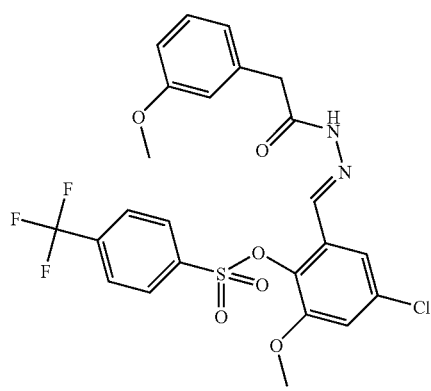 | 4-chloro-2-((E)-{[(3-methoxyphenyl)acetyl]hydrazono}methyl)-phenyl 4-(trifluoromethyl)benzenesulfonate; |
| 168. | 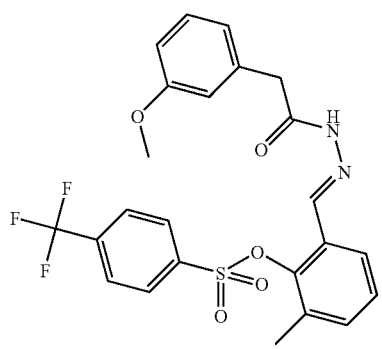 | 2-((E)-{[(3-methoxyphenyl)acetyl]hydrazono}methyl)-6-methylphenyl 4-(trifluoromethyl)benzenesulfonate; |
| 169. | 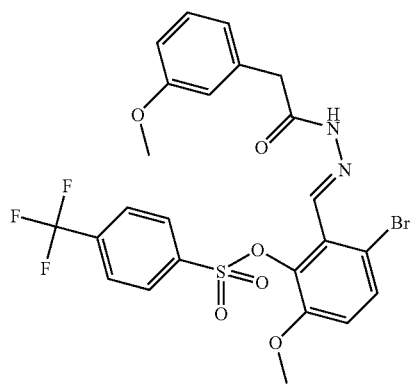 | 3-bromo-6-methoxy-2-((E)-{[(3-methoxyphenyl)acetyl]hydrazono}methyl)-phenyl 4-(trifluoromethyl)benzenesulfonate; |

TABLE I-continued

| 170. | 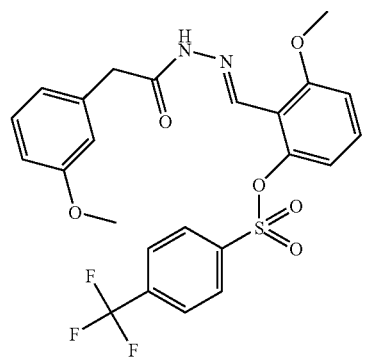 | 3-methoxy-2-((E)-{[(3-methoxyphenyl)acetyl]hydrazono}methyl)-phenyl 4-(trifluoromethyl)benzenesulfonate; |
| --- | --- | --- |
| 171. | 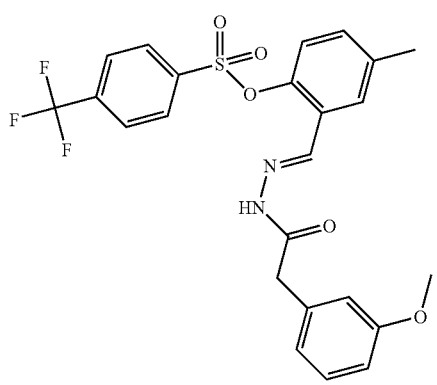 | 2-((E)-{[(3-methoxyphenyl)acetyl]hydrazono}methyl)-4-methylphenyl 4-(trifluoromethyl)benzenesulfonate; |
| 172. | 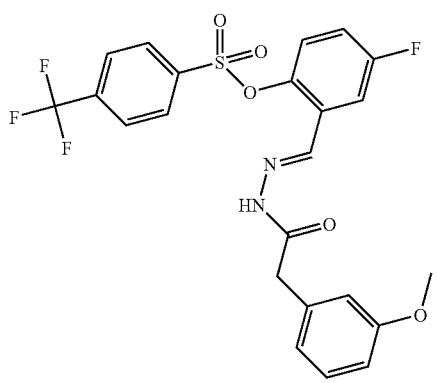 | 4-fluoro-2-((E)-{[(3-methoxyphenyl)acetyl]hydrazono}methyl)-phenyl 4-(trifluoromethyl)benzenesulfonate; |
| 173. | 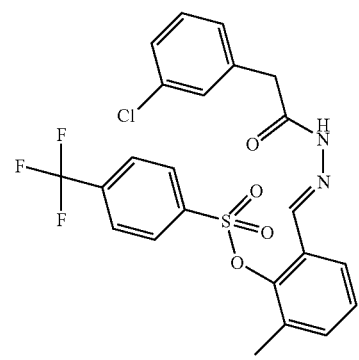 | 2-((E)-{[(3-chlorophenyl)acetyl]hydrazono}methyl)-6-methylphenyl 4-(trifluoromethyl)benzenesulfonate; |

TABLE I-continued

| | | |
|---|---|---|
| 174. | 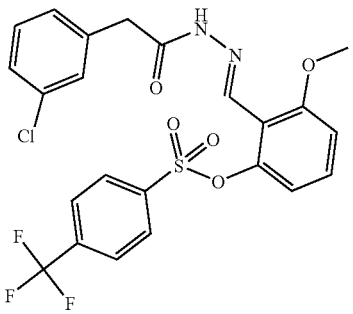 | 2-((E)-{[(3-chlorophenyl)acetyl]hydrazono}methyl)-3-methoxyphenyl 4-(trifluoromethyl)benzenesulfonate; |
| 175. | 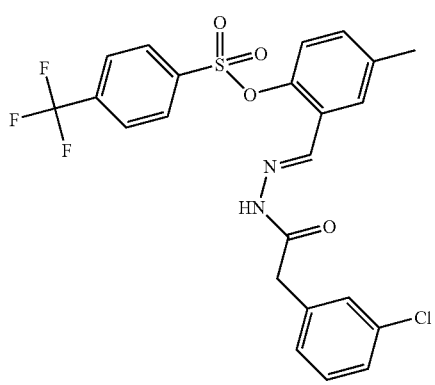 | 2-((E)-{[(3-chlorophenyl)acetyl]hydrazono}methyl)-4-methylphenyl 4-(trifluoromethyl)benzenesulfonate; |
| 176. | 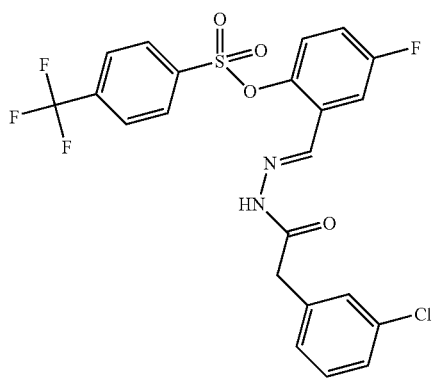 | 2-((E)-{[(3-chlorophenyl)acetyl]hydrazono}methyl)-4-fluorophenyl 4-(trifluoromethyl)benzenesulfonate; |
| 177. | 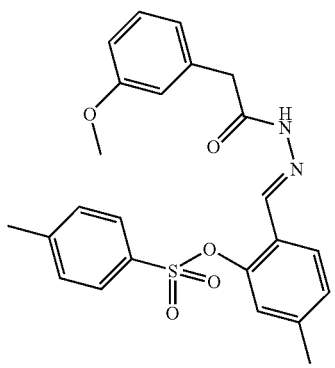 | 2-((E)-{[(3-methoxyphenyl)acetyl]hydrazono}methyl)-5-methylphenyl 4-methylbenzenesulfonate; |

TABLE I-continued

| | | |
|---|---|---|
| 178. | 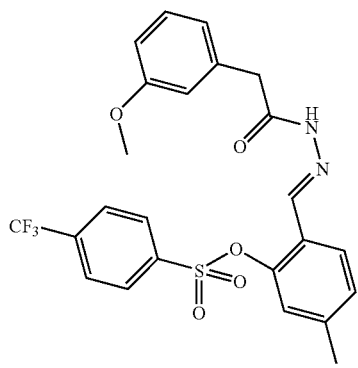 | 2-((E)-{[(3-methoxyphenyl)acetyl]hydrazono}methyl)-5-methylphenyl 4-(trifluoromethyl)benzenesulfonate; |
| 179. | 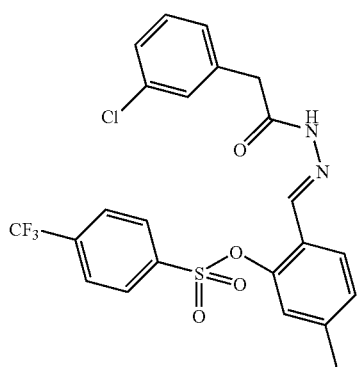 | 2-((E)-{[(3-chlorophenyl)acetyl]hydrazono}methyl)-5-methylphenyl 4-(trifluoromethyl)benzenesulfonate; |
| 180. | 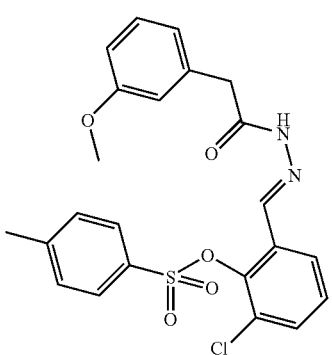 | 2-chloro-6-((E)-{[(3-methoxyphenyl)acetyl]hydrazono}methyl)-phenyl 4-methylbenzenesulfonate; |
| 181. | 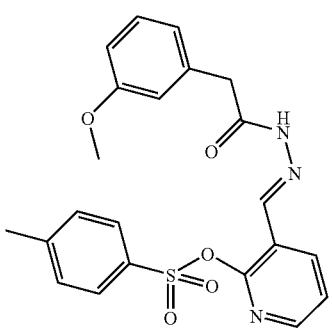 | 3-((E)-{2-[2-(3-methoxyphenyl)acetyl]hydrazono}methyl)-pyridin-2-yl 4-methylbenzenesulfonate; |

TABLE I-continued
182. 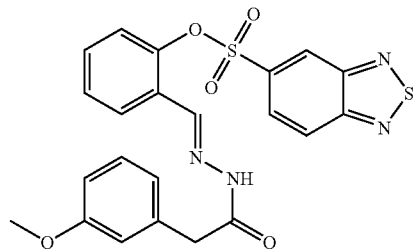 2-((E)-{2-[2-(3-methoxyphenyl)acetyl]hydrazono}methyl)-phenyl 2,1,3-benzothiadiazole-5-sulfonate;
183. 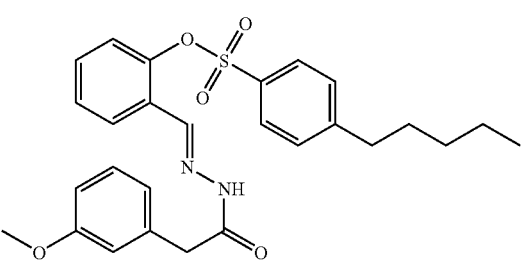 2-((E)-{2-[2-(3-methoxyphenyl)acetyl]hydrazono}methyl)-phenyl 4-pentylbenzenesulfonate;
184. 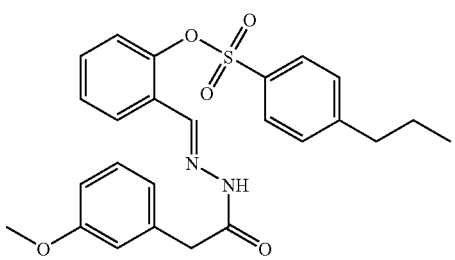 2-((E)-{2-[2-(3-methoxyphenyl)acetyl]hydrazono}methyl)-phenyl 4-propylbenzenesulfonate;
185. 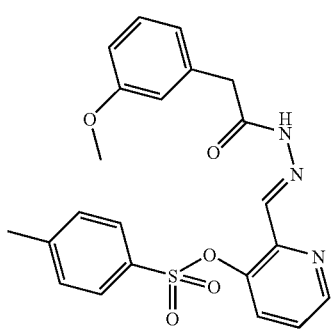 2-((E)-{2-[2-(3-methoxyphenyl)acetyl]hydrazono}methyl)-pyridin-3-yl 4-methylbenzenesulfonate;

TABLE I-continued
| | | |
|---|---|---|
| 186. | 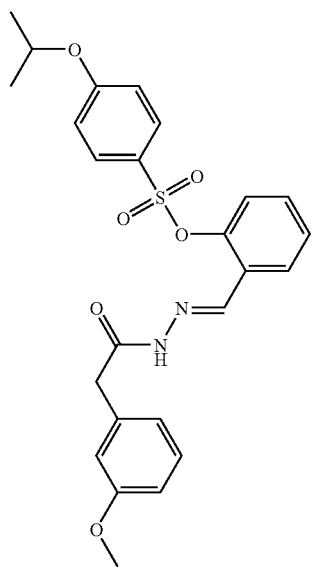 | 2-((E)-{2-[2-(3-methoxyphenyl)acetyl]hydrazono}methyl)-phenyl 4-isopropoxybenzenesulfonate; |
| 187. | 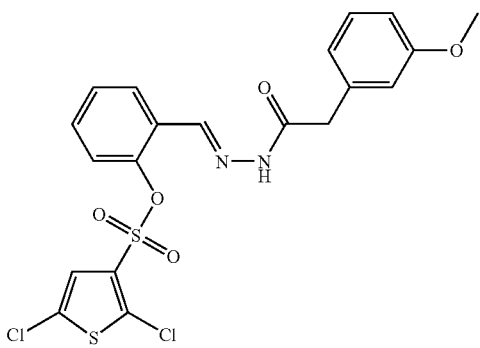 | 2-((E)-{2-[2-(3-methoxyphenyl)acetyl]hydrazono}methyl)-phenyl 2,5-dichlorothiophene-3-sulfonate; |
| 188. | 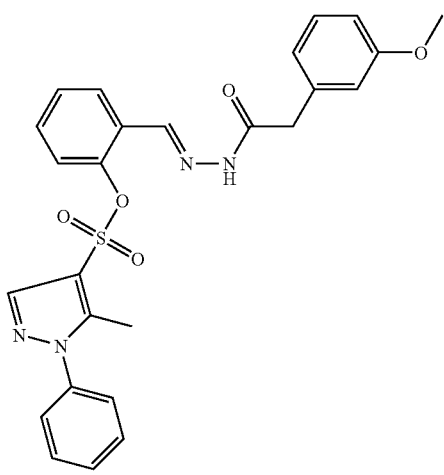 | 2-((E)-{2-[2-(3-methoxyphenyl)acetyl]hydrazono}methyl)-phenyl 5-methyl-1-phenyl-1H-pyrazole-4-sulfonate; |

TABLE I-continued
189. 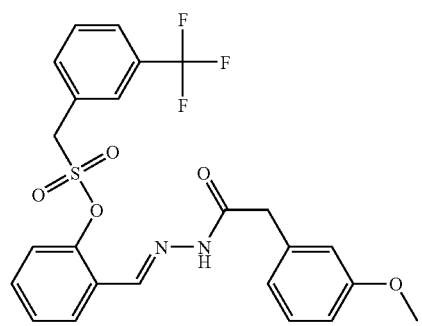 2-((E)-{2-[2-(3-methoxyphenyl)acetyl]hydrazono}methyl)-phenyl [3-(trifluoromethyl)phenyl]methanesulfonate;
190. 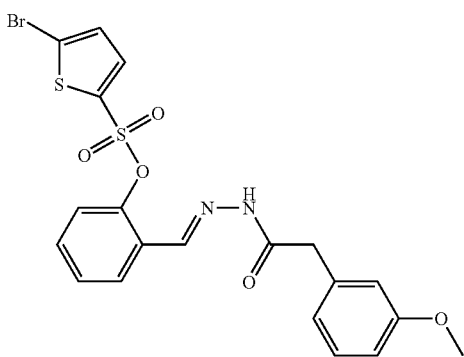 2-((E)-{2-[2-(3-methoxyphenyl)acetyl]hydrazono}methyl)-phenyl 5-bromothiophene-2-sulfonate;
191. 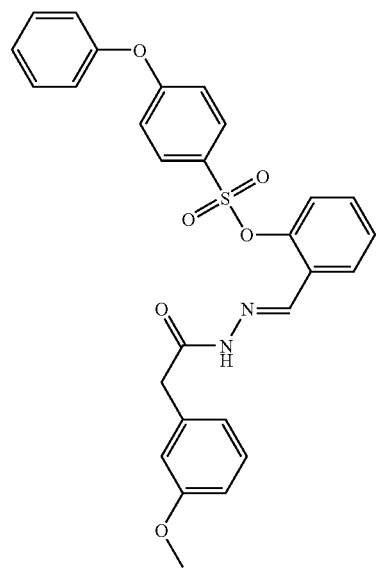 2-((E)-{2-[2-(3-methoxyphenyl)acetyl]hydrazono}methyl)-phenyl 4-phenoxybenzenesulfonate;

TABLE I-continued
192. 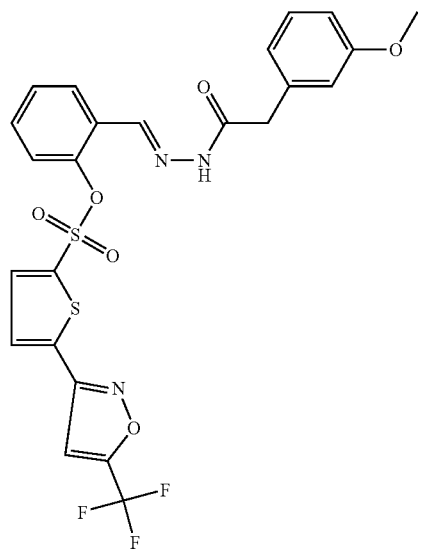 2-((E)-{2-[2-(3-methoxyphenyl)acetyl]hydrazono}methyl)-phenyl 5-[5-(trifluoromethyl)isoxazol-3-yl]thiophene-2-sulfonate;
193. 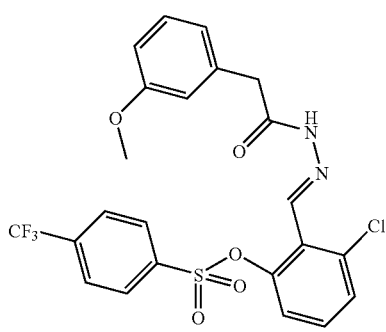 3-chloro-2-((E)-{[(3-methoxyphenyl)acetyl]hydrazono}methyl)-phenyl 4-(trifluoromethyl)benzenesulfonate;
194. 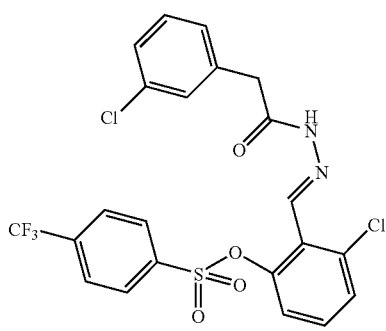 3-chloro-2-((E)-{[(3-chlorophenyl)acetyl]hydrazono}methyl)-phenyl 4-(trifluoromethyl)benzenesulfonate;

TABLE I-continued
195. 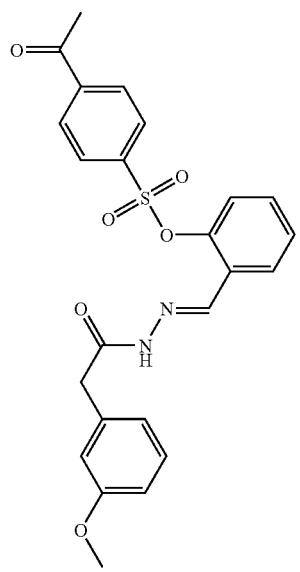 2-((E)-{2-[2-(3-methoxyphenyl)acetyl]hydrazono}methyl)-phenyl 4-acetylbenzenesulfonate;
196. 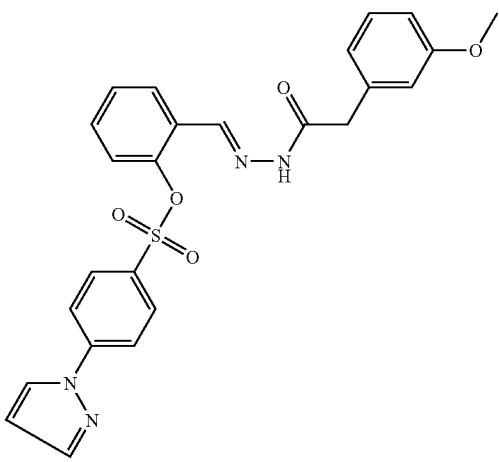 2-((E)-{2-[2-(3-methoxyphenyl)acetyl]hydrazono}methyl)-phenyl 4-(1H-pyrazol-1-yl)benzenesulfonate;
197. 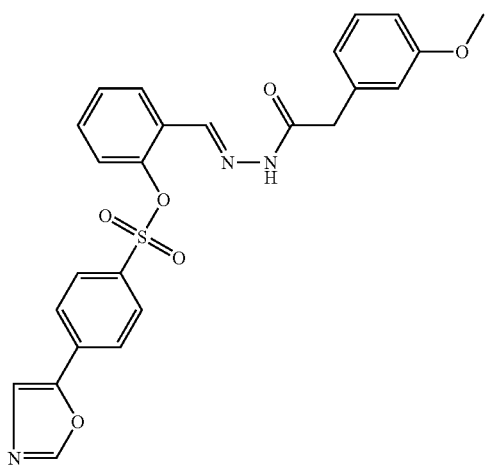 2-((E)-{2-[2-(3-methoxyphenyl)acetyl]hydrazono}methyl)-phenyl 4-(1,3-oxazol-5-yl)benzenesulfonate;

TABLE I-continued
| 198. | 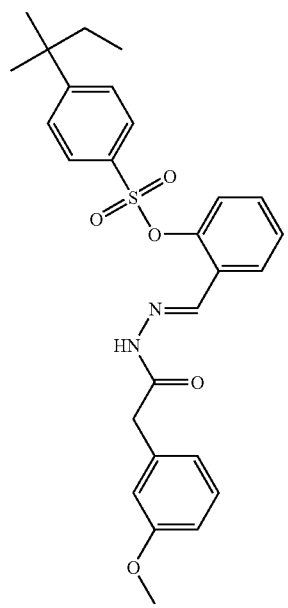 | 2-((E)-{2-[2-(3-methoxyphenyl)acetyl]hydrazono}methyl)-phenyl 4-(1,1-dimethylpropyl)benzenesulfonate; |
| 199. | 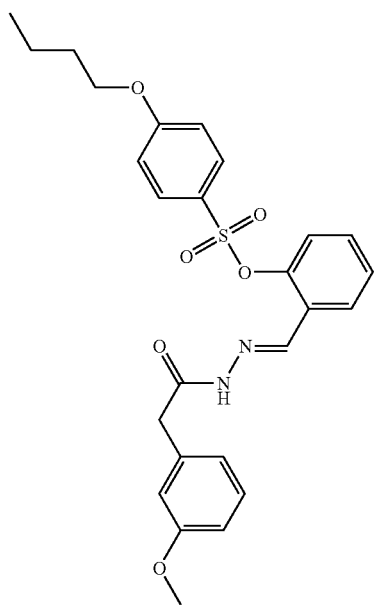 | 2-((E)-{2-[2-(3-methoxyphenyl)acetyl]hydrazono}methyl)-phenyl 4-butoxybenzenesulfonate; |
| 200. | 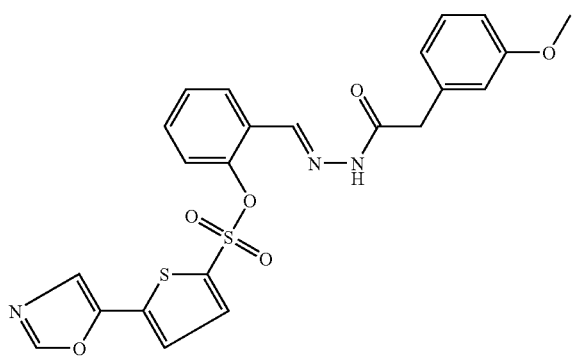 | 2-((E)-{2-[2-(3-methoxyphenyl)acetyl]hydrazono}methyl)-phenyl 5-(1,3-oxazol-5-yl)thiophene-2-sulfonate; |

TABLE I-continued
| 201. | 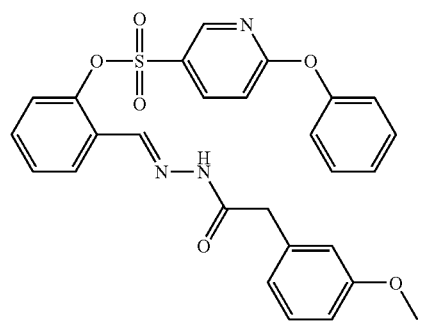 | 2-((E)-{2-[2-(3-methoxyphenyl)acetyl]hydrazono}methyl)-phenyl 6-phenoxypyridine-3-sulfonate; |
| 202. | 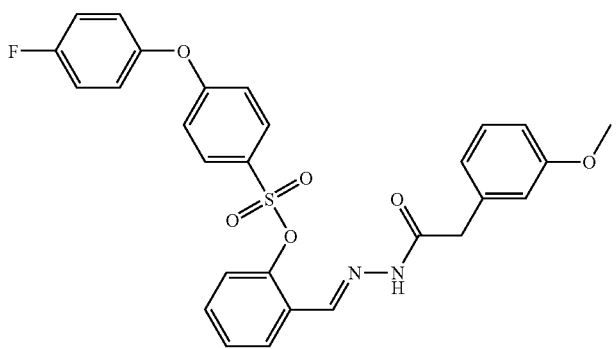 | 2-((E)-{2-[2-(3-methoxyphenyl)acetyl]hydrazono}methyl)-phenyl 4-(4-fluorophenoxy)benzenesulfonate; |
| 203. | 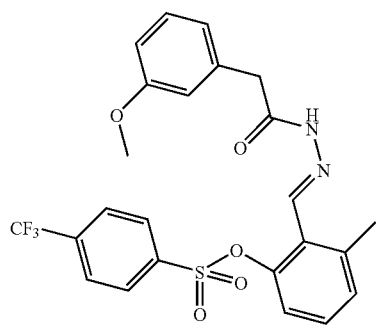 | 2-((E)-{[(3-methoxyphenyl)acetyl]hydrazono}methyl)-3-methylphenyl 4-(trifluoromethyl)benzenesulfonate; |
| 204. | 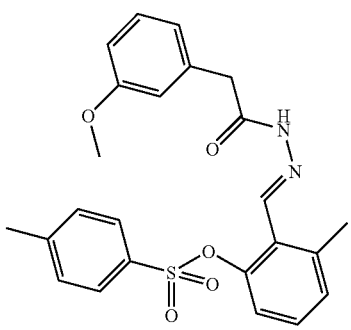 | 2-((E)-{[(3-methoxyphenyl)acetyl]hydrazono}methyl)-3-methylphenyl 4-methylbenzenesulfonate; |

TABLE I-continued

| | | |
|---|---|---|
| 205. | 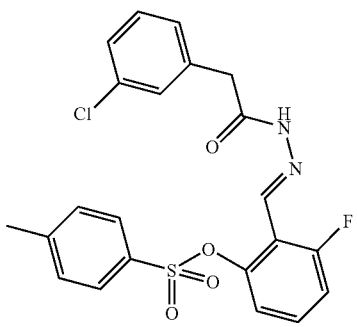 | 2-((E)-{[(3-chlorophenyl)acetyl]hydrazono}methyl)-3-fluorophenyl 4-methylbenzenesulfonate; |
| 206. | 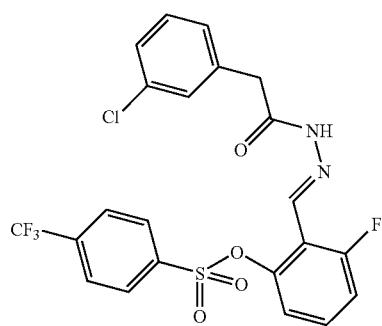 | 2-((E)-{[(3-chlorophenyl)acetyl]hydrazono}methyl)-3-fluorophenyl 4-(trifluoromethyl)benzenesulfonate; |
| 207. | 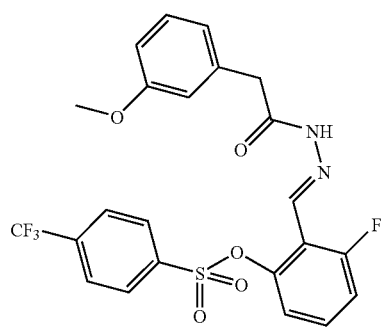 | 3-fluoro-2-((E)-{[(3-methoxyphenyl)acetyl]hydrazono}methyl)-phenyl 4-(trifluoromethyl)benzenesulfonate; |
| 208. | 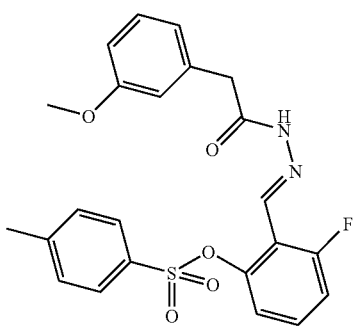 | 3-fluoro-2-((E)-{[(3-methoxyphenyl)acetyl]hydrazono}methyl)-phenyl 4-methylbenzenesulfonate; |

TABLE I-continued

| 209. | 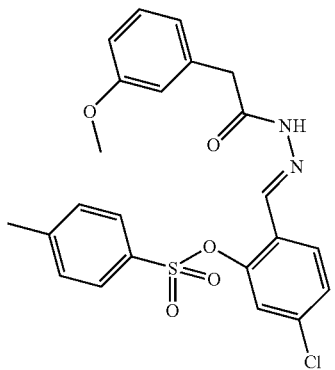 | 5-chloro-2-((E)-{[(3-methoxyphenyl)acetyl]hydrazono}methyl)-phenyl 4-methylbenzenesulfonate; |
| --- | --- | --- |
| 210. | 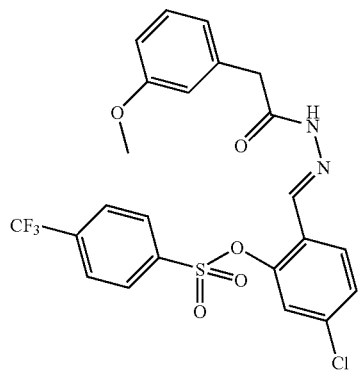 | 5-chloro-2-((E)-{[(3-methoxyphenyl)acetyl]hydrazono}methyl)-phenyl 4-(trifluoromethyl)benzenesulfonate; |
| 211. | 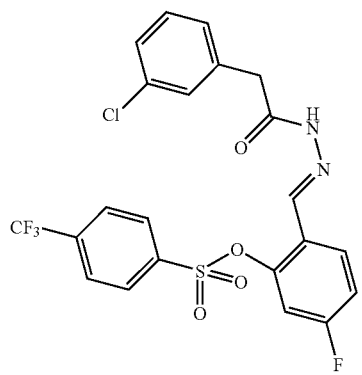 | 2-((E)-{[(3-chlorophenyl)acetyl]hydrazono}methyl)-5-fluorophenyl 4-(trifluoromethyl)benzenesulfonate; |
| 212. | 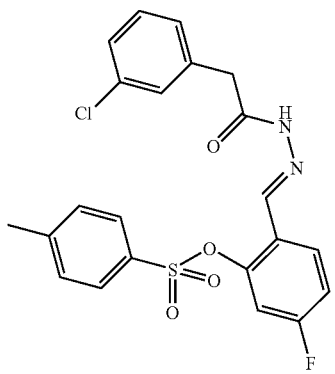 | 2-((E)-{[(3-chlorophenyl)acetyl]hydrazono}methyl)-5-fluorophenyl 4-methylbenzenesulfonate; |

TABLE I-continued

| | | |
|---|---|---|
| 213. | 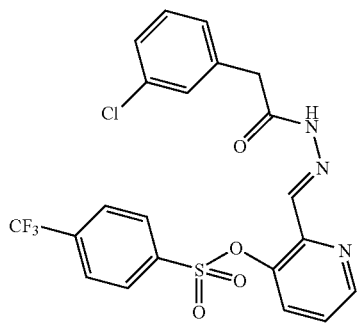 | 2-((E)-{2-[2-(3-chlorophenyl)acetyl]hydrazono}methyl)-pyridin-3-yl 4-(trifluoromethyl)benzenesulfonate; |
| 214. | 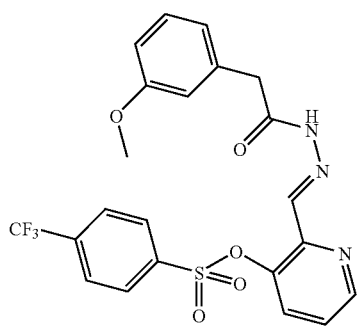 | 2-((E)-{2-[2-(3-methoxyphenyl)acetyl]hydrazono}methyl)-pyridin-3-yl 4-(trifluoromethyl)benzenesulfonate; |
| 215. | 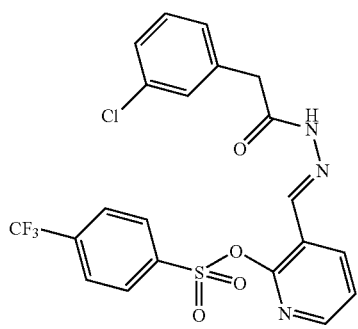 | 3-((E)-{2-[2-(3-chlorophenyl)acetyl]hydrazono}methyl)-pyridin-2-yl 4-(trifluoromethyl)benzenesulfonate; |
| 216. | 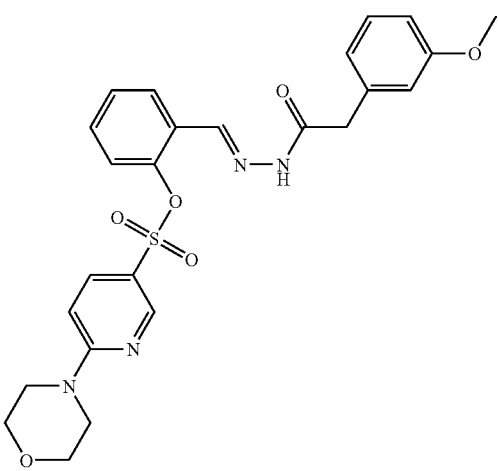 | 2-((E)-{2-[2-(3-methoxyphenyl)acetyl]hydrazono}methyl)-phenyl 6-morpholin-4-ylpyridine-3-sulfonate; |

TABLE I-continued
217. 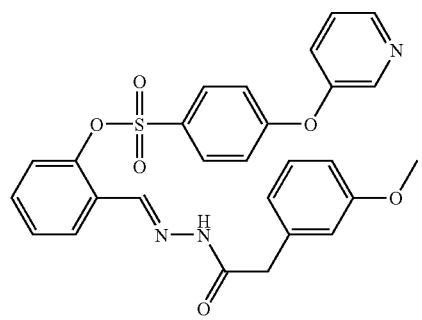 2-((E)-{2-[2-(3-methoxyphenyl)acetyl]hydrazono}methyl)-phenyl 4-(pyridin-3-yloxy)benzenesulfonate;
218. 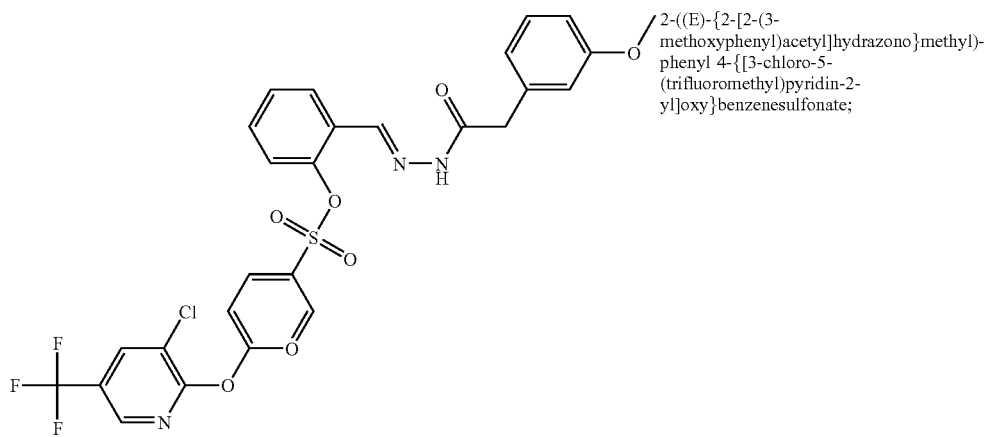 2-((E)-{2-[2-(3-methoxyphenyl)acetyl]hydrazono}methyl)-phenyl 4-{[3-chloro-5-(trifluoromethyl)pyridin-2-yl]oxy}benzenesulfonate;
219. 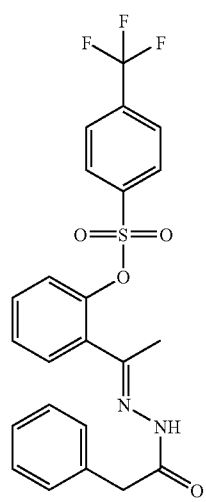 2-[(1E)-N-(phenylacetyl)ethanehydrazonoyl]phenyl 4-(trifluoromethyl)benzenesulfonate;

TABLE I-continued

| | | |
|---|---|---|
| 220. | 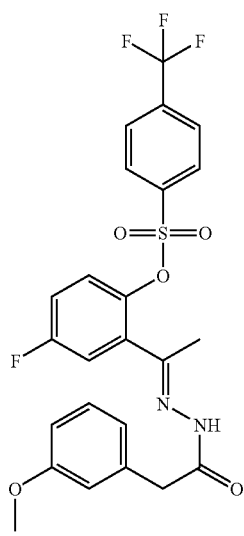 | 4-fluoro-2-{(1E)-N-[(3-methoxyphenyl)acetyl]ethanehydrazonoyl}-phenyl 4-(trifluoromethyl)-benzenesulfonate |
| 221. | 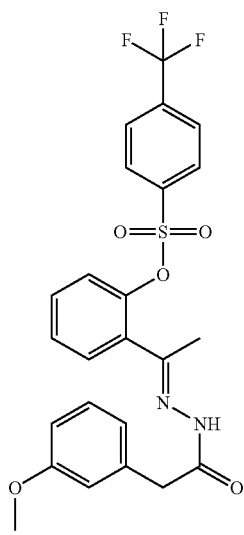 | 2-{(1E)-N-[(3-methoxyphenyl)acetyl]ethanehydrazonoyl}-phenyl 4-(trifluoromethyl)benzenesulfonate |
| 222. | 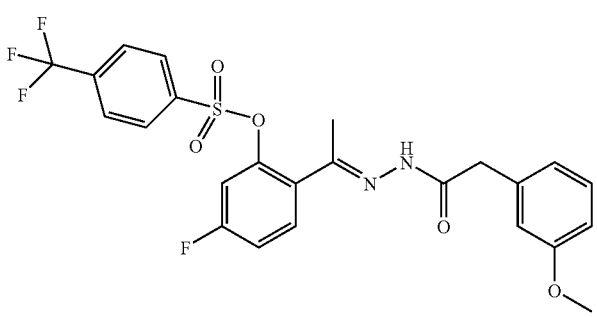 | 5-fluoro-2-{(1E)-N-[(3-methoxyphenyl)acetyl]ethanehydrazonoyl}-phenyl 4-(trifluoromethyl)benzenesulfonate |
| 223. | 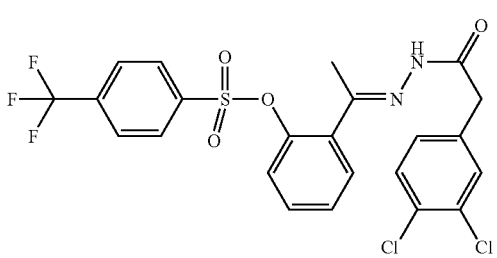 | 2-{(1E)-N-[(3,4-dichlorophenyl)acetyl]ethanehydrazonoyl}-phenyl 4-(trifluoromethyl)benzenesulfonate |

TABLE I-continued
224. 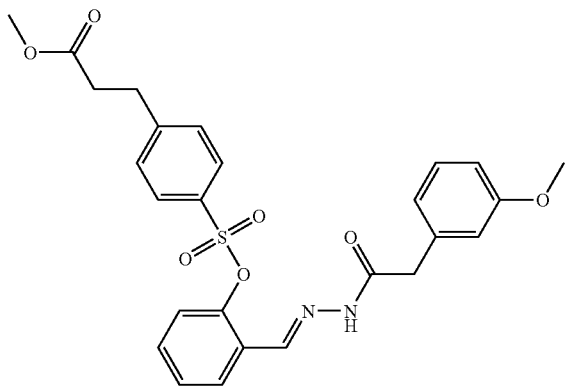
methyl 3-(4-{[2-((E)-{[(3-methoxyphenyl)acetyl]hydrazono}methyl)-phenoxy]sulfonyl}phenyl)propanoate;
225. 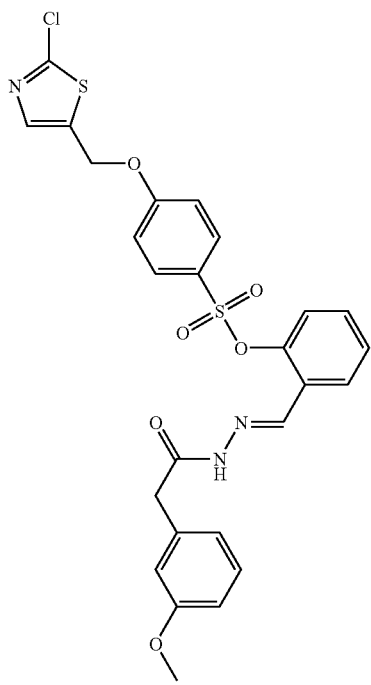
2-((E)-{2-[2-(3-methoxyphenyl)acetyl]hydrazono}methyl)-phenyl 4-[(2-chloro-1,3-thiazol-5-yl)methoxy]benzenesulfonate;
226. 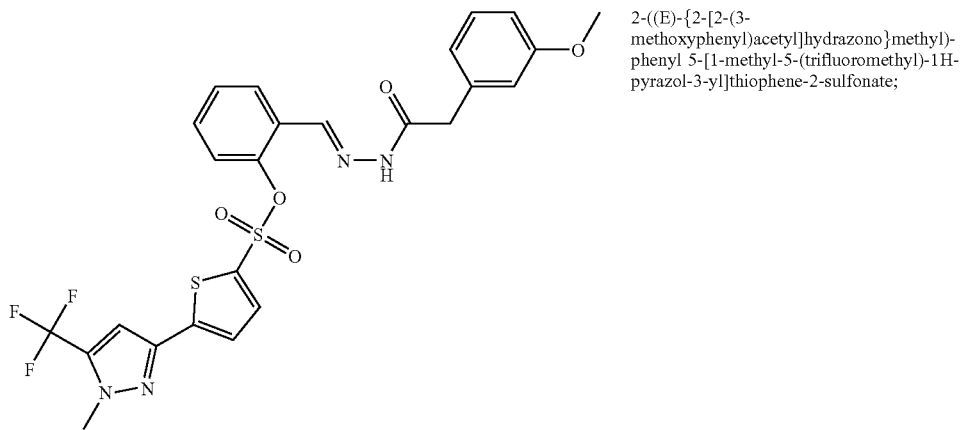
2-((E)-{2-[2-(3-methoxyphenyl)acetyl]hydrazono}methyl)-phenyl 5-[1-methyl-5-(trifluoromethyl)-1H-pyrazol-3-yl]thiophene-2-sulfonate;

TABLE I-continued

| | | |
|---|---|---|
| 227. | 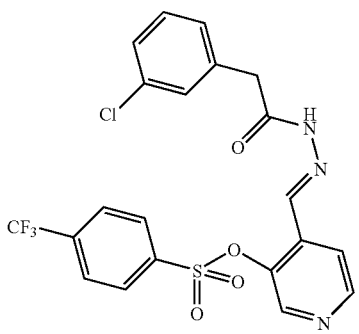 | 4-((E)-{2-[2-(3-chlorophenyl)acetyl]hydrazono}methyl)-pyridin-3-yl 4-(trifluoromethyl)benzenesulfonate; |
| 228. | 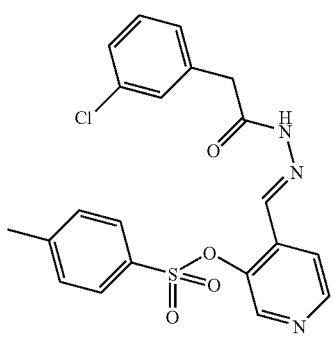 | 4-((E)-{2-[2-(3-chlorophenyl)acetyl]hydrazono}methyl)-pyridin-3-yl 4-methylbenzenesulfonate; |
| 229. | 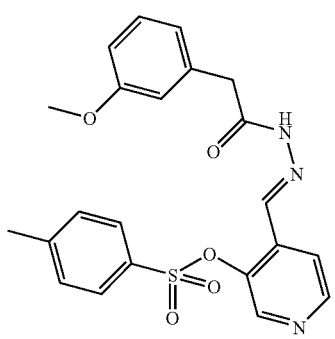 | 4-((E)-{2-[2-(3-methoxyphenyl)acetyl]hydrazono}methyl)-pyridin-3-yl 4-methylbenzenesulfonate; |
| 230. | 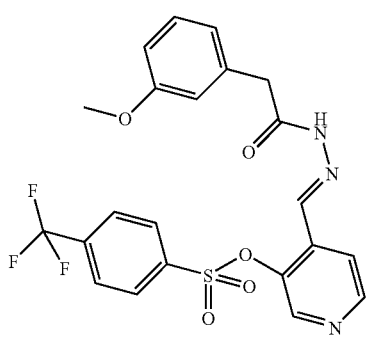 | 4-((E)-{2-[2-(3-methoxyphenyl)acetyl]hydrazono}methyl)-pyridin-3-yl 4-(trifluoromethyl)benzenesulfonate; |
| 231. | 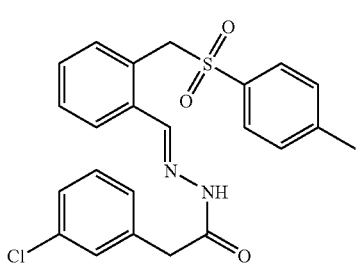 | 2-(3-chlorophenyl)-N'-[(1E)-(2-{[(4-methylphenyl)sulfonyl]methyl}phenyl)-methylene]acetohydrazide; |

TABLE I-continued

| | | |
|---|---|---|
| 232. | 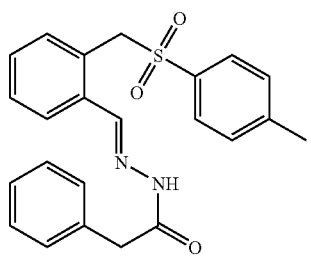 | N'-[(1E)-(2-{[(4-methylphenyl)sulfonyl]methyl}phenyl)-methylene]-2-phenylacetohydrazide; |
| 233. | 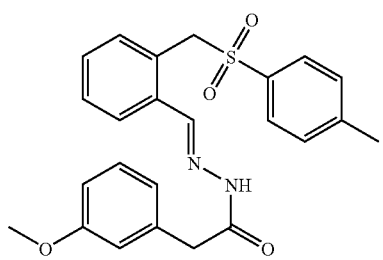 | 2-(3-methoxyphenyl)-N'-[(1 E)-(2-{[(4-methylphenyl)sulfonyl]methyl}phenyl)-methylene]acetohydrazide; |
| 234. | 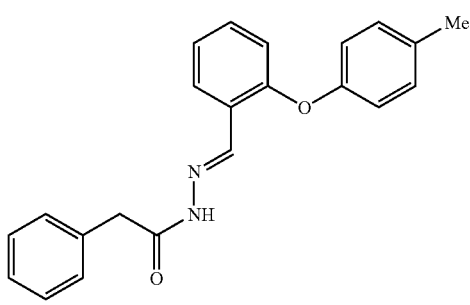 | N'-{(1E)-[2-(4-methylphenoxy)phenyl]methylene}-2-phenylacetohydrazide; |
| 235. | 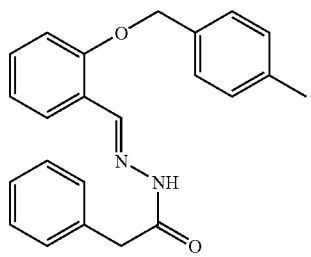 | N'-((1E)-{2-[(4-methylbenzyl)oxy]phenyl}methylene)-2-phenylacetohydrazide; |
| 236. | 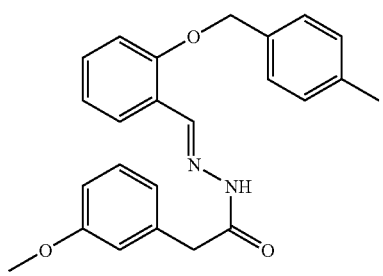 | 2-(3-methoxyphenyl)-N'-((1E)-{2-[(4-methylbenzyl)oxy]phenyl}methylene)-acetohydrazide; |

TABLE I-continued

| 237. | 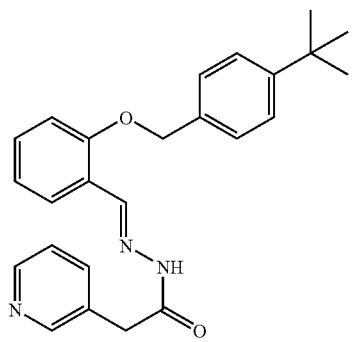 | N'-((1E)-{2-[(4-tert-butylbenzyl)oxy]phenyl}methylene)-2-pyridin-3-ylacetohydrazide; |
| --- | --- | --- |
| 238. | 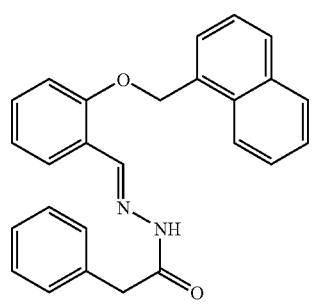 | N'-{(1E)-[2-(1-naphthylmethoxy)phenyl]methylene}-2-phenylacetohydrazide; |
| 239. | 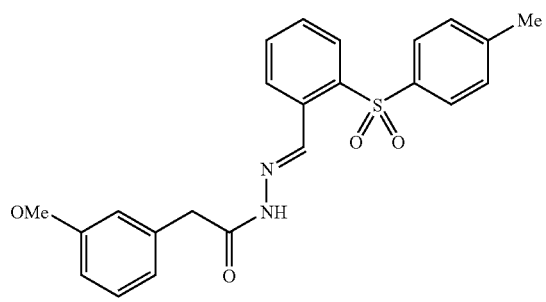 | 2-(3-methoxyphenyl)-N'-((1E)-{2-[(4-methylphenyl)sulfonyl]phenyl}methylene)-acetohydrazide; |
| 240. | 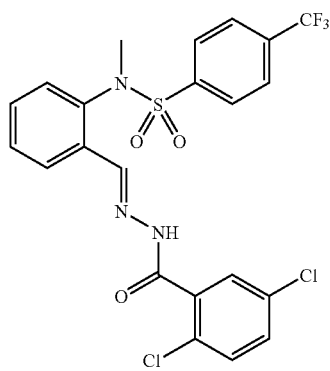 | N-(2-{(E)-[(2,5-dichlorobenzoyl)hydrazono]methyl}phenyl)-N-methyl-4-(trifluoromethyl)benzenesulfonamide; |
| 241. | 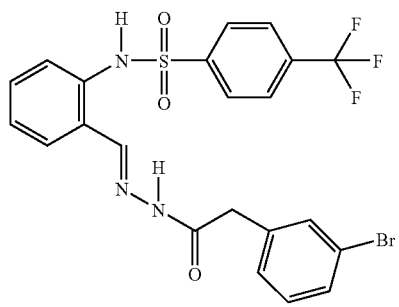 | N-[2-((E)-{[(3-bromophenyl)acetyl]hydrazono}methyl)phenyl]-4-(trifluoromethyl)benzenesulfonamide; |

TABLE I-continued

242. 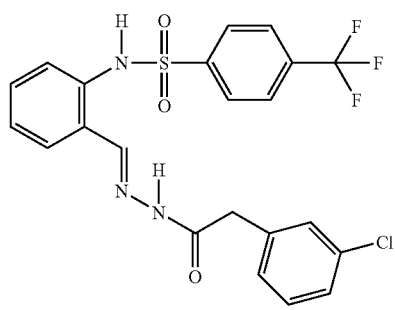 N-[2-((E)-{[(3-chlorophenyl)acetyl]hydrazono}methyl)-phenyl]-4-(trifluoromethyl)benzenesulfonamide;

243. 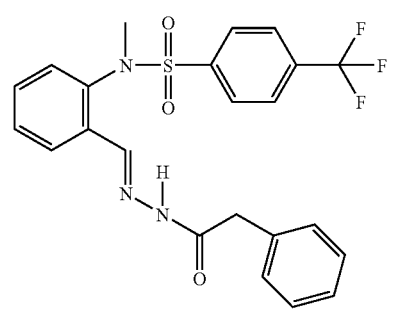 N-methyl-N-(2-{(E)-[(phenylacetyl)hydrazono]methyl}phenyl)-4-(trifluoromethyl)benzenesulfonamide;

244. 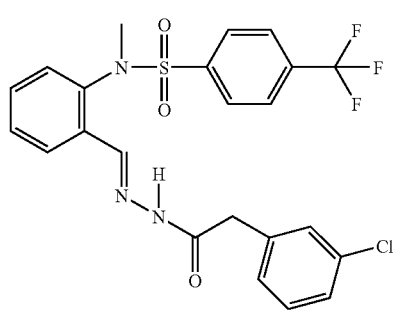 N-[2-((E)-{[(3-chlorophenyl)acetyl]hydrazono}methyl)-phenyl]-N-methyl-4-(trifluoromethyl)benzenesulfonamide;

245. 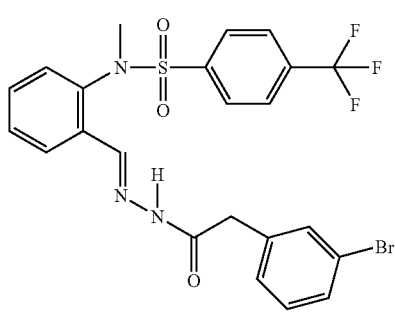 N-[2-((E)-{[(3-bromophenyl)acetyl]hydrazono}methyl)-phenyl]-N-methyl-4-(trifluoromethyl)benzenesulfonamide;

246. 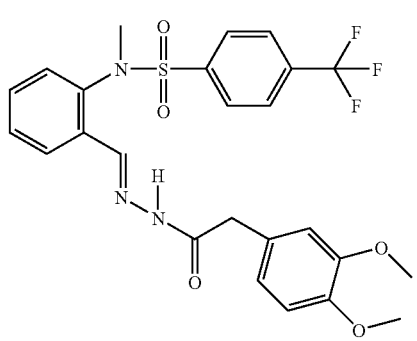 N-[2-((E)-{[(3,4-dimethoxyphenyl)acetyl]hydrazono}methyl)-phenyl]-N-methyl-4-(trifluoromethyl)benzenesulfonamide;

TABLE I-continued

247. 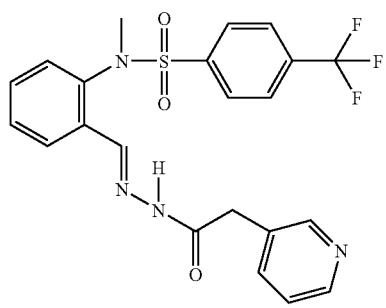 N-methyl-N-(2-{(E)-[(pyridin-3-ylacetyl)hydrazono]methyl}phenyl)-4-(trifluoromethyl)benzenesulfonamide;

248. 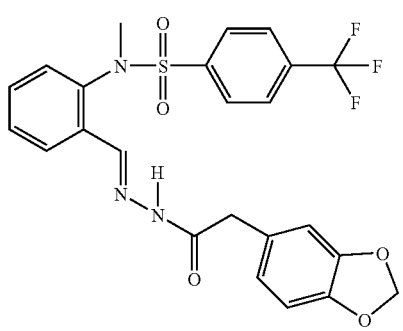 N-(2-{(E)-[(1,3-benzodioxol-5-ylacetyl)hydrazono]methyl}phenyl)-N-methyl-4-(trifluoromethyl)benzenesulfonamide;

249. 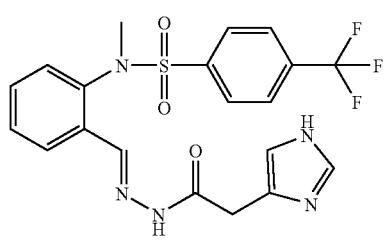 N-(2-{(E)-[(1H-imidazol-4-ylacetyl)hydrazono]methyl}phenyl)-N-methyl-4-(trifluoromethyl)benzenesulfonamide;

250. 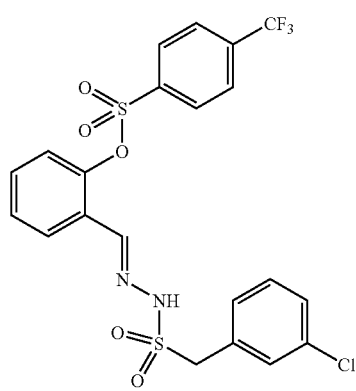 2-((E)-[2-[(3-chlorobenzyl)sulfonyl]hydrazono]methyl)-phenyl 4-(trifluoromethyl)benzenesulfonate;

251. 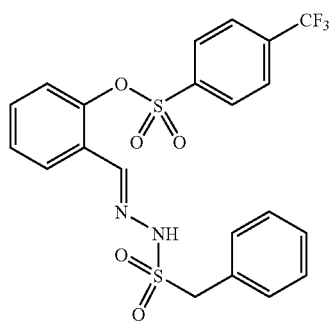 2-{(E)-[2-(benzylsulfonyl)hydrazono]methyl}phenyl 4-(trifluoromethyl)benzenesulfonate;

TABLE I-continued

| | | |
|---|---|---|
| 252. | 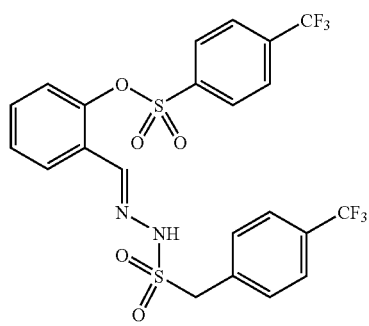 | 2-[(E)-(2-{[4-(trifluoromethyl)benzyl]sulfonyl}hydrazono)-methyl]phenyl 4-(trifluoromethyl)benzenesulfonate; |
| 253. | 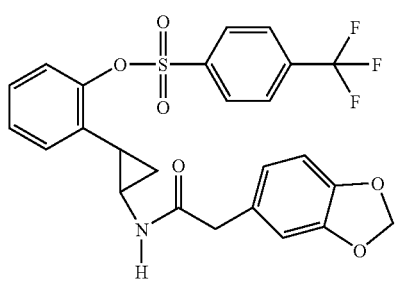  Racemic, suspected trans stereochemistry | 2-(2-{[2-(1,3-benzodioxol-5-yl)acetyl]amino}cyclopropyl)phenyl 4-(trifluoromethyl)benzenesulfonate; |
| 254. | 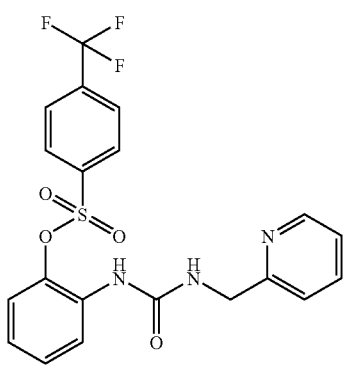 | 2-({[(pyridin-2-ylmethyl)amino]carbonyl}amino)phenyl 4-(trifluoromethyl)benzenesulfonate; |
| 255. | 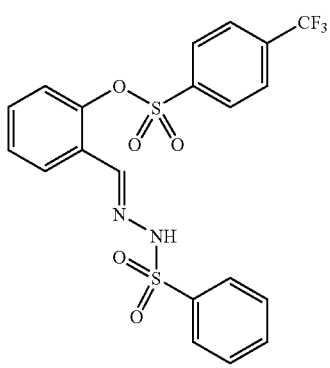 | 2-{(E)-[2-(phenylsulfonyl)hydrazono]methyl}phenyl 4-(trifluoromethyl)benzenesulfonate; |

TABLE I-continued

| | | |
|---|---|---|
| 256. | 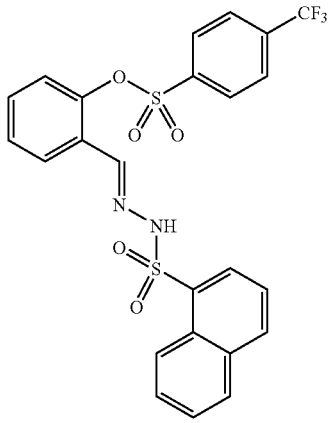 | 2-{(E)-[2-(1-naphthylsulfonyl)hydrazono]methyl}phenyl 4-(trifluoromethyl)benzenesulfonate; |

Analysis of the Compounds

The subject compounds and compositions may be demonstrated to have pharmacological activity, e.g, antiviral activity, in in vitro and in vivo assays, as known in the art. See for example Behrens, S. E., et. al EMBO J. 15:12–22; Lohmann, V., et. al., 1997, J. Virol. 71:8416–8428; Ferrari, E., et al., 1999. J. Virol. 73:1649–1654; Bealieu, P. L. et. al., WO0204425 A2; Perni, R. B. et. al., WO9833501; which references are incorporated by reference herein.

The subject compounds and compositions are capable of specifically inhibiting or suppressing a viral infection, e.g., an HCV infection. An in vivo assessment of the antiviral activity of the compounds of the invention may be made using an animal model of viral infection, e.g., a primate model. Cell-based assays may be performed using, e.g, a cell line directly infected with a virus. Cell-based assays for activity against a specific viral component, e.g., a polymerase, may also be performed. Additionally, biochemical or mechanism-based assays, e.g., transcription assays using a purified protein, Northern blot, RT-PCR, etc., may be performed.

The above-described assays are exemplary and not intended to limit the scope of the invention. The skilled practitioner can appreciate that modifications can be made to conventional assays to develop equivalent assays that obtain the same result.

High throughput assays for the presence, absence, quantification, or other properties of particular compounds are well known to those of skill in the art. Such assays may be adapted to identify compounds capable of modifying a viral RNA dependent RNA polymerase protein, e.g., NS5B using functional protein. Preferred assays thus detect enhancement or inhibition of HCV RNA-dependent RNA activity.

Compositions

In view of the antiviral activity associated with the compounds described above, the present invention further provides pharmaceutical compositions comprising one or more of the above compounds in combination with a pharmaceutically acceptable excipient.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a prodrug, which can be metabolically or chemically converted to the subject compound by the recipient host. A wide variety of prodrug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Methods of Use

In yet another aspect, the present invention provides novel methods for the use of the foregoing compounds and compositions. In particular, the invention provides novel methods for treating or preventing viral infections, e.g., HCV infection. The invention also provides novel methods for treating or preventing diseases resulting from, in whole or in part, viral infections, preferably diseases resulting from, in whole or in part, infection, such as hepatitis C, cirrhosis, chronic liver disease and hepatocellular carcinoma. The methods typically involve administering to a patient an effective amount of one or more of the subject compounds or compositions.

The compositions may be advantageously combined and/or used in combination with other antiviral agents which are either therapeutic or prophylactic agents, and different from the subject compounds. The compositions may also be advantageously combined and/or used in combination with agents that treat conditions often associated with the viral infections that are sensitive to the present compounds, such as anti-HIV agents or immunosuppressive agents. In many instances, administration in conjunction with the subject compositions enhances the efficacy of such agents. Accordingly, the present compounds, when combined or administered in combination with other antiviral agents, can be used in dosages which are less than the expected amounts when used alone, or less than the calculated amounts for combination therapy.

Exemplary treatment options for hepatitis C(HCV) include interferons, e.g., interferon alfa-2b, interferon alfa-2a, and interferon alfacon-1. Less frequent interferon dosing can be achieved using pegylated interferon (interferon attached to a polyethylene glycol moiety which significantly improves its pharmacokinetic profile). Combination therapy with interferon alfa-2b (pegylated and unpegylated) and ribavarin has also been shown to be efficacious for some patient populations. Other agents currently being developed include RNA replication inhibitors, antisense agents, therapeutic vaccines, protease ihibitors, helicase inhibitors and antibody therapy (monoclonal and polyclonal).

The compounds and compositions of the present invention may also be used with agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric 5 presentation of antigen and an adjuvant.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

Preparation of the Compounds

The compounds of this invention can be prepared by one or more of the following schemes described below.

Scheme 1:

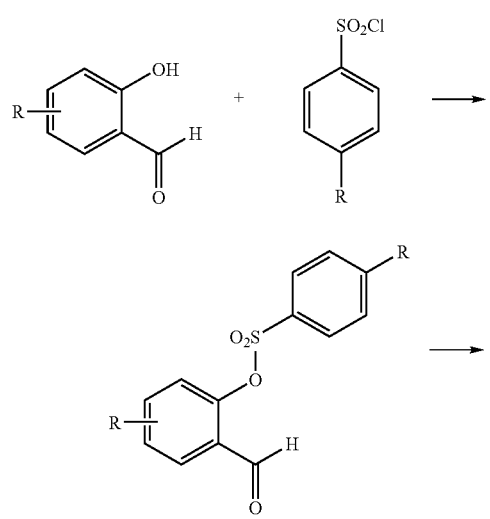

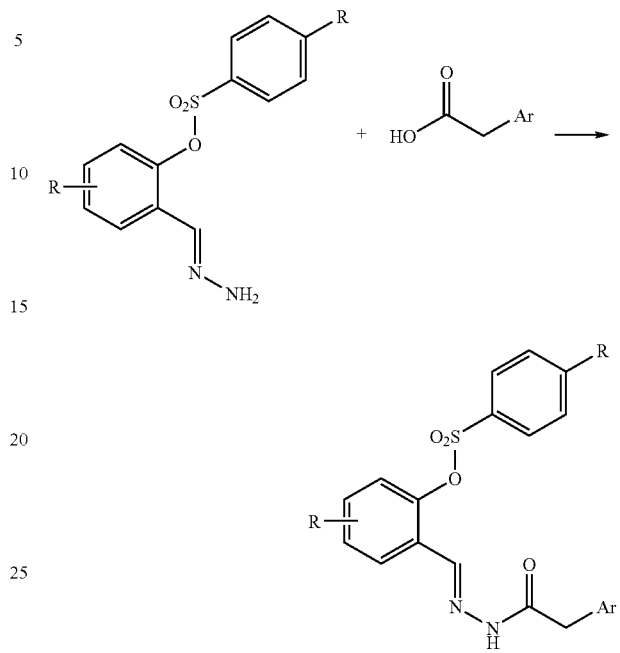

Scheme 2:

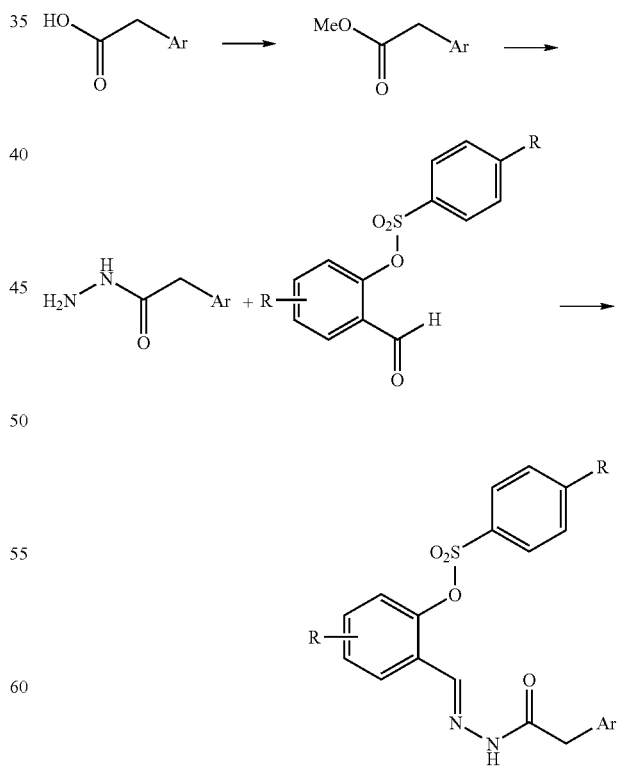

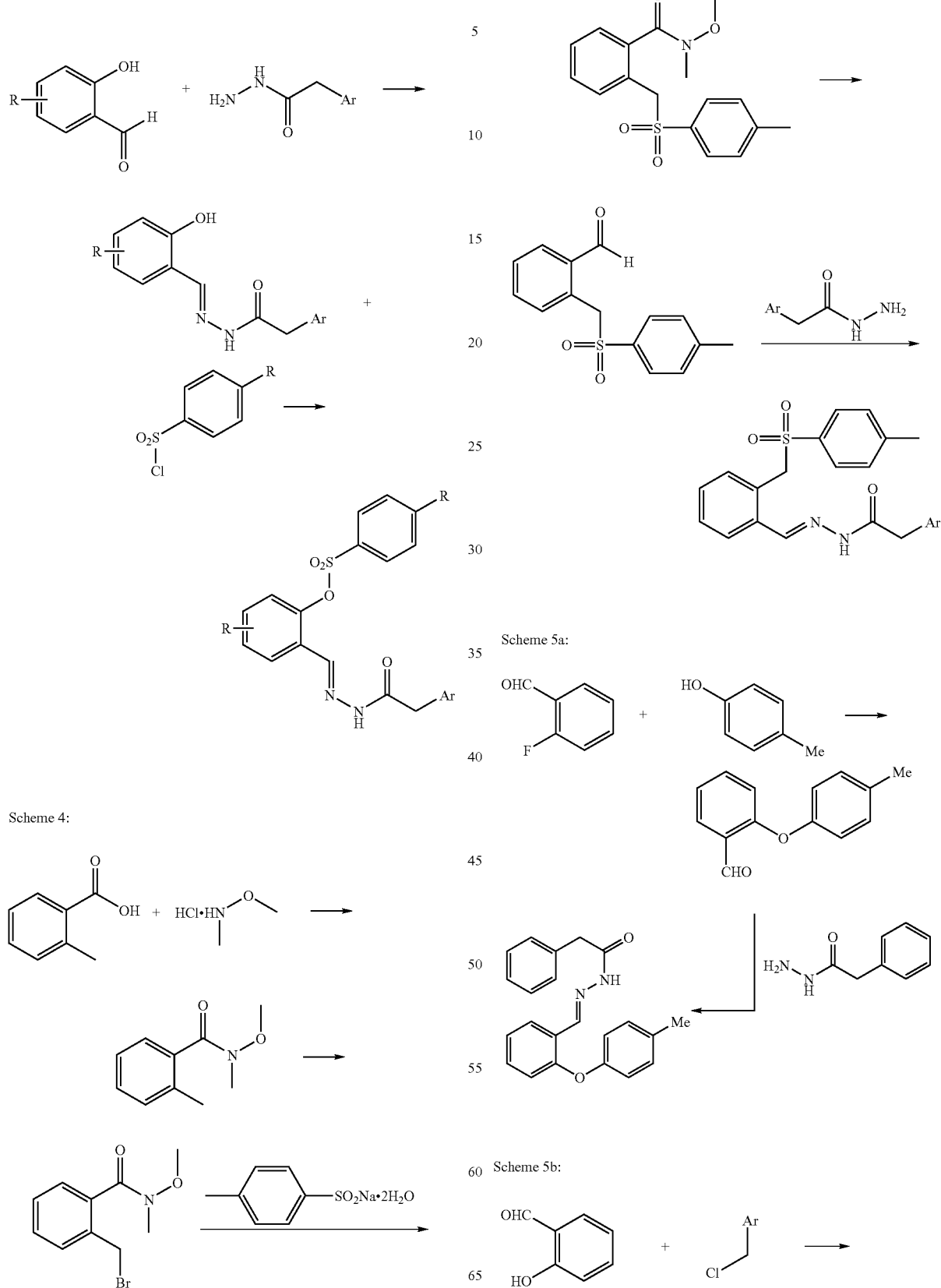

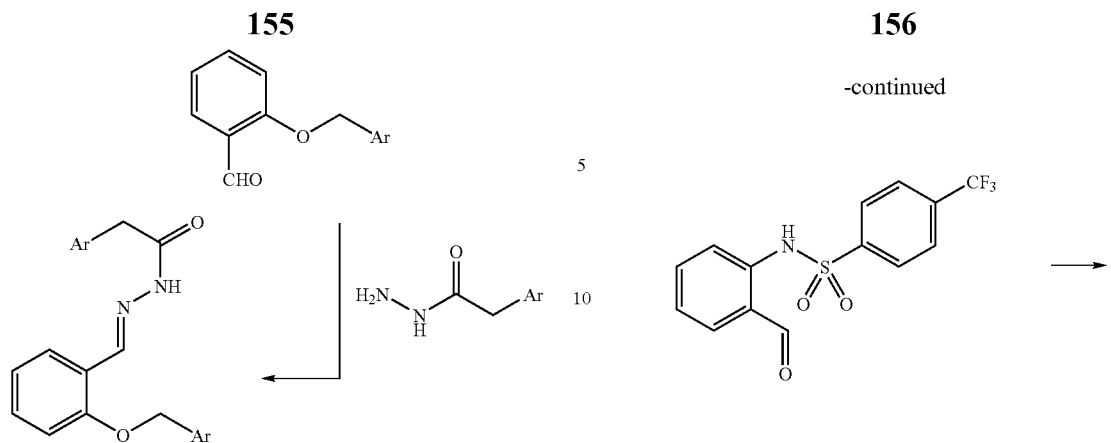
Scheme 5c:
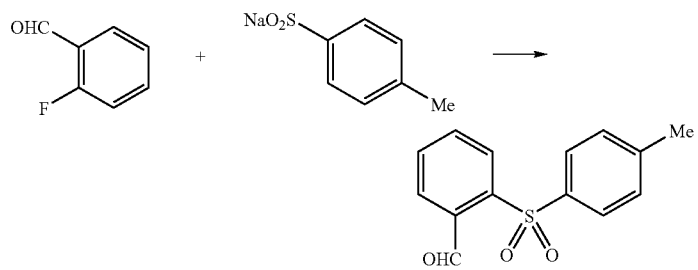
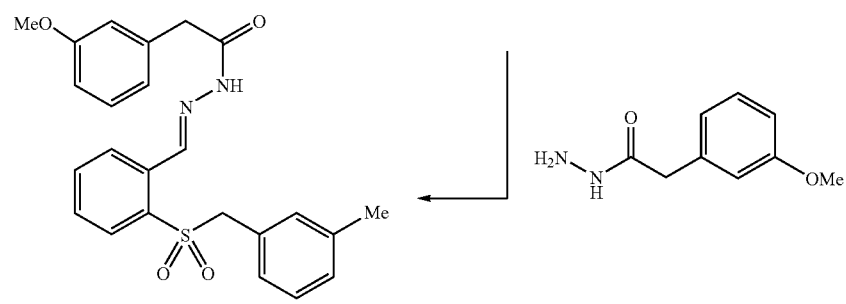
Scheme 6a:
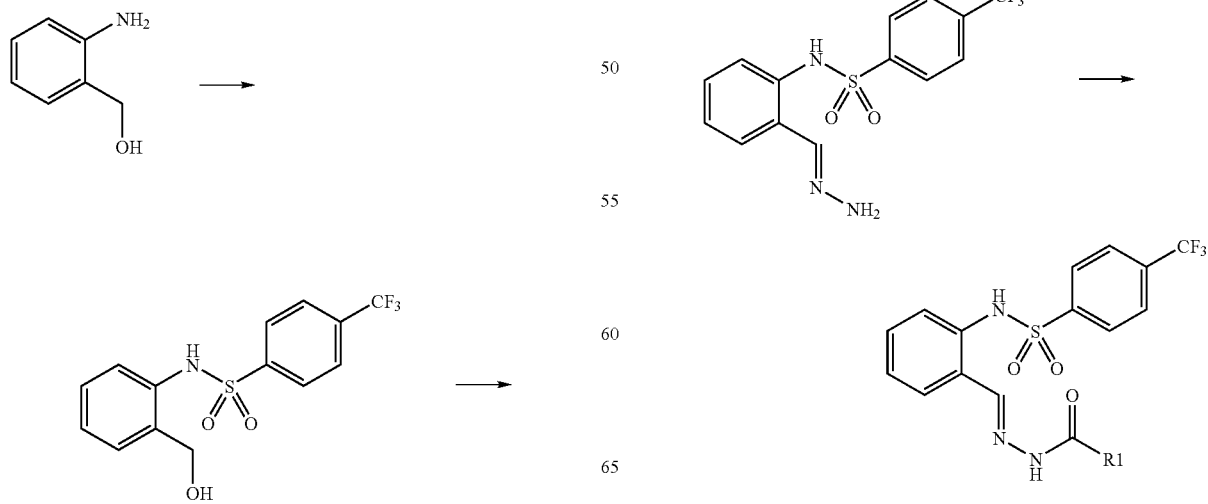

Scheme 6b:
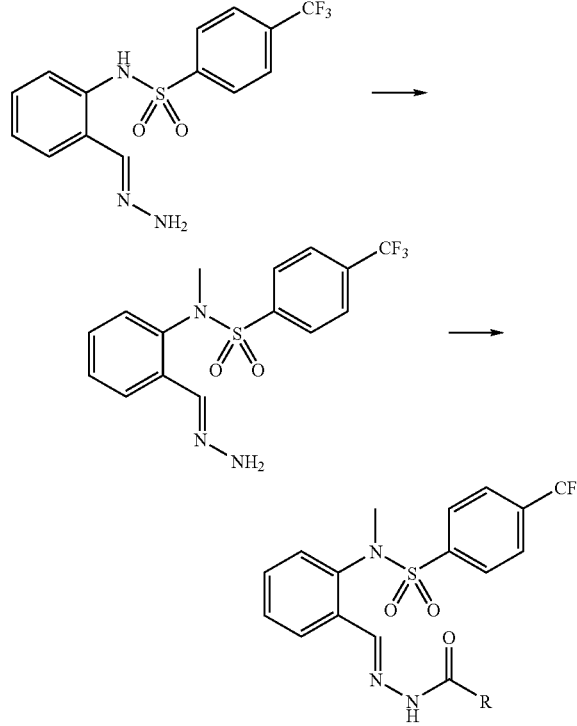
Scheme 7:
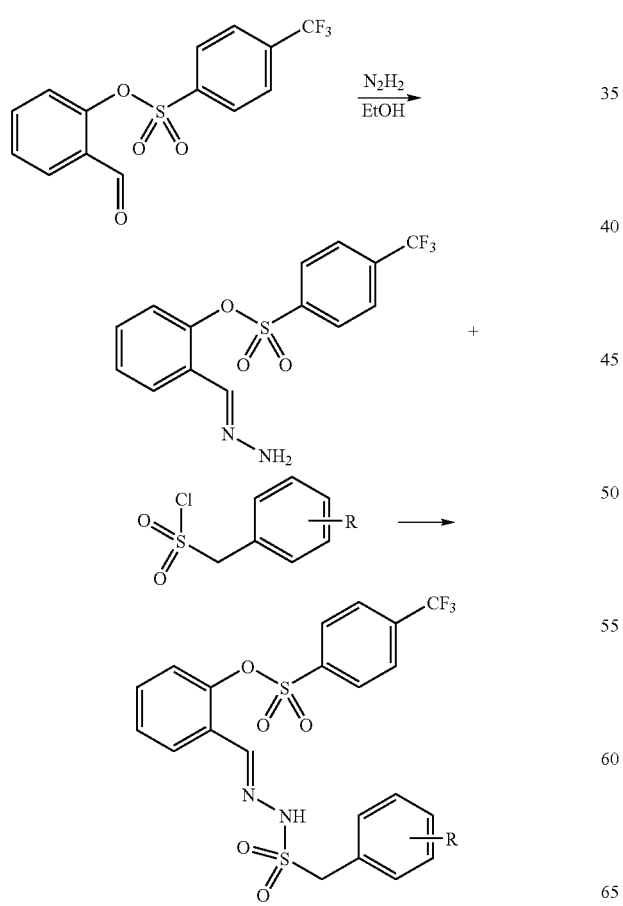
Scheme 8:
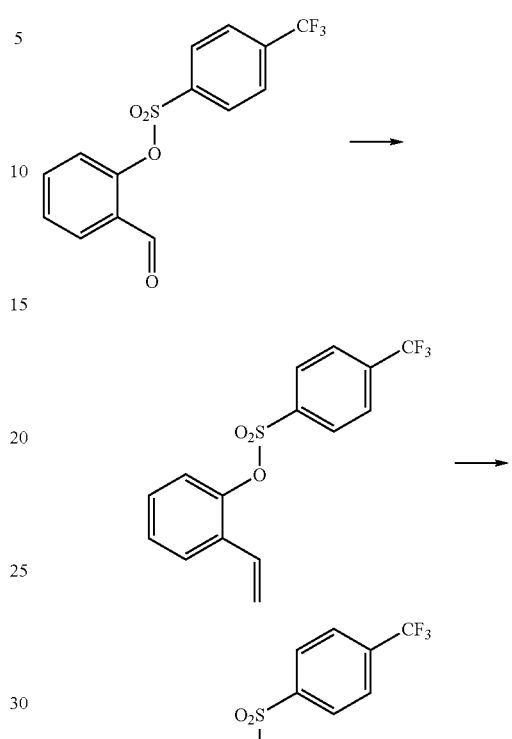
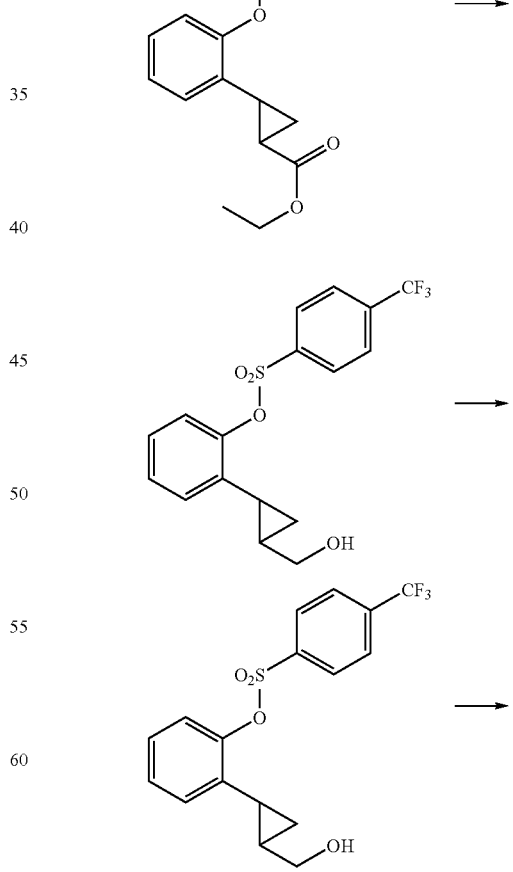

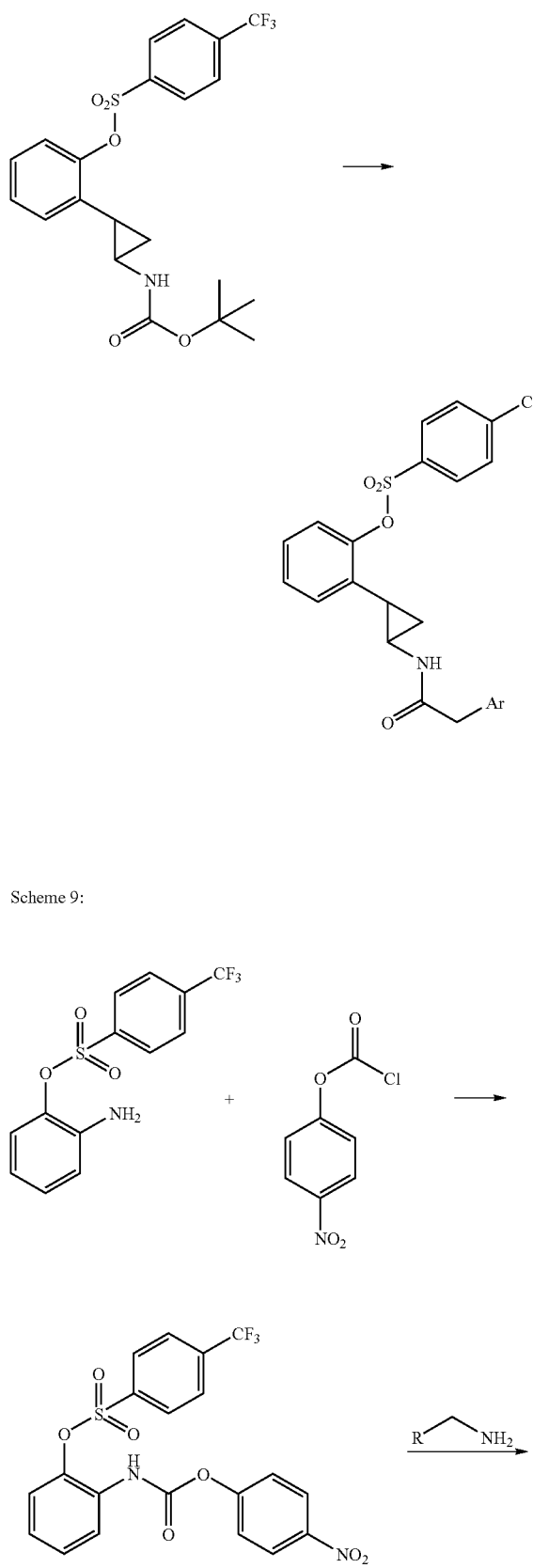

Scheme 9:

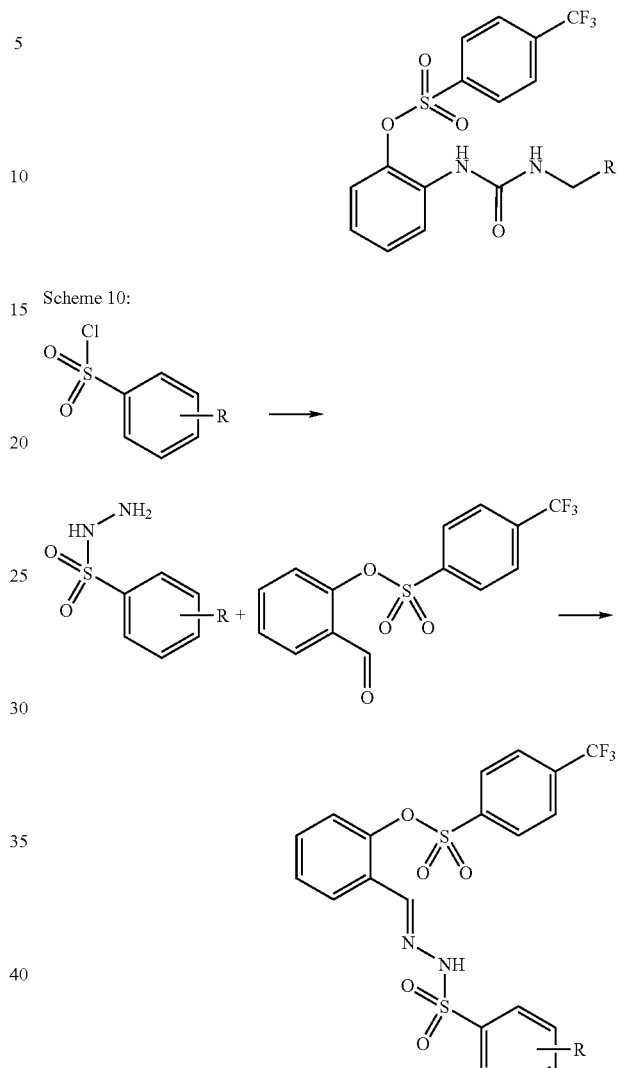

Scheme 10:

EXAMPLES

The following examples further illustrate the preparation and analysis of compounds of the invention. The examples are illustrative only and not intended to limit the scope of the invention in any way. Reagents and solvents can be obtained from commercial sources such as Aldrich Chemical Co. (Milwaukee, Wis., USA). All commercially obtained reagents are used as received without further purification. Solvents are used as received or dried over appropriate drying agents and distilled. Proton NMR experiments are carried out on a Bruker 400 MHz spectrometer, and chemical shifts are reported in ppm downfield from internal TMS. Carbon NMR experiments are carried out on a Bruker 500 MHz spectrometer, and chemical shifts are reported in ppm relative to the central line of deuteriochloroform at 77.0 ppm. Low resolution mass spectra (ESI) are obtained on a Micromass Platform C spectrograph. Low resolution mass spectra (EI) and high resolution mass spectra (FAB), as well as IR spectra and elemental analyses are conducted by the Pharmacia analytical laboratory. Flash column chromatography is carried out on Biotage 40 prepacked columns, while preparative TLC is carried out on Merck silica gel $F_{254}$-coated plates with 0.25 mm or 0.5 mm silica layers. Unless otherwise noted, reactions are carried out in dry glassware under a nitrogen atmosphere.

The aromatic aldehydes used in the examples were prepared according to procedures described in the literature as listed below.

- 3-chloro-2-hydroxybenzaldehyde; Casiraghi, Giovanni; Casnati, Giuseppe; Puglia, Giuseppe; Sartori, Giovanni; Terenghi, Giuliana; *J. Chem. Soc. Perkin Trans.* 1, 1980; 1862–1865.

- 5-chloro-2-hydroxybenzaldehyde; Hepworth, John D.; Jones, Terry K.; Livingstone, Robert; *Tetrahedron;* 37; 15; 1981; 2613–2616.

- 4-fluoro-2-hydroxybenzaldehyde; Aldred, Robert; Johnston, Robert; Levin, Daniel; Neilan, James; *J. Chem. Soc. Perkin Trans.* 1; 13; 1994; 1823–1832.

- 5-fluoro-2-hydroxybenzaldehyde; Aldred, Robert; Johnston, Robert; Levin, Daniel; Neilan, James; *J. Chem. Soc. Perkin Trans.* 1; 13; 1994; 1823–1832.

- 5-methyl-2-hydroxybenzaldehyde; Komiyama, Makoto; Hirai, Hidefumi; *J. Amer. Chem. Soc.;* 105; 7; 1983; 2018–2021.

- 2-hydroxynicotinaldehyde; Guilbert; Johnson; *Biochemistry;* 10; 1971; 2313.

- 3-hydroxypyridine-2-carboxaldehyde; Wang, Pou-Hsiung; Keck, James, G.; Lien, Eric J.; Lai, Michael M. C.; *J. Med. Chem.*; EN; 33; 2; 1990; 608–614.

Example 1 According to Scheme 1

2-((E)-{2-[2-(1,3-benzodioxol-5-yl)acetyl]hydrazono}methyl)phenyl 4-(trifluoromethyl)benzenesulfonate [PHA-818736]

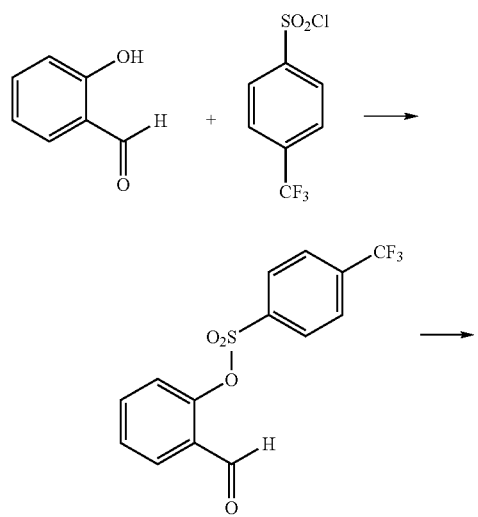

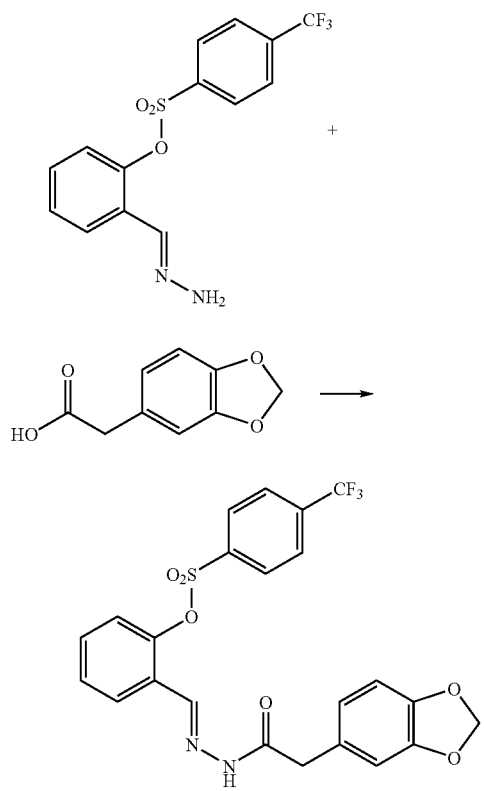

A solution of 4-(trifluoromethyl)benzenesulphonyl chloride (2.4 g, 9.84 mmol) in pyridine (40 mL) is cooled to 0° C. Salicylaldehyde (1.44 g, 11.8 mmol) is added and stirred overnight. Water and ethyl acetate are added to the reaction and shaken. The organic layer is washed with dilute HCl (0.1 N×2), $H_2O$, bicarbonate solution, $H_2O$ and dried with sodium sulfate. The organic layer is evaporated to dryness to give a yellow solid, which is recrystallized from ether/hexane to give 2-formylphenyl 4-(trifluoromethyl)benzenesulfonate as a yellow powder (1.70 g, 52%).

A solution of 2-formylphenyl 4-(trifluoromethyl)benzenesulfonate (1.7 g, 5.1 mmol) in warm ethanol (100 mL) is added dropwise over 1 hour into a solution of hydrazine (6 equiv) in ethanol (5 mL). The reaction is stirred at room temperature overnight at which time the solvent is evaporated to dryness. The crude product is recrystallized from $CH_2Cl_2$/hexane to remove a dimer by-product. An 89% yield of 2-[hydrazonomethyl]phenyl 4-(trifluoromethyl)benzenesulfonate (4.65 g) is obtained.

A solution of 2-[hydrazonomethyl]phenyl 4-(trifluoromethyl)benzenesulfonate (150 mg, 0.44 mmol) and 1,3-benzodioxol-5-ylacetic acid (1.2 equiv) in DMF (1 mL) is treated with a solution of 1-ethyl-3-(3-dimethylaminopropyl)carbodiimide hydrochloride (EDC) (167 mg, 0.87 mmol) and 4-dimethylaminopyridine (DMAP) (106 mg, 0.87 mmol) in $CH_2Cl_2$ (10 mL). The solution is shaken overnight on an orbital shaker. The solution is evaporated to dryness using a speed. Water is added to the mixture, which is then sonicated to give a solid. The solid is filtered and washed with a large amount of water. A small amount of methanol is added and the mixture sonicated. The resulting solid is filtered and washed with more methanol to yield pure 2-((E)-{2-[2-(1,3-benzodioxol-5-yl)acetyl]

hydrazono}methyl)phenyl 4-(trifluoromethyl)benzenesulfonate. The yield is 169 mg, 77%. $^1$H NMR (400 MHz, DMSO) □ 11.48 (2s, 1H), 8.01 (m, 6H), 7.12 (m, 6H), 5.99 (2s, 2H), 3.62 (2s, 2H). ESI– for $C_{23}H_{17}F_3N_2O_6S$, m/z 505, (M–H)–.

Example 2 According to Scheme 2

2-{[2-(2-arylacetyl)hydrazono]methyl}phenyl 4-trifluoromethyl)benzenesulfonate [PHA-813673]

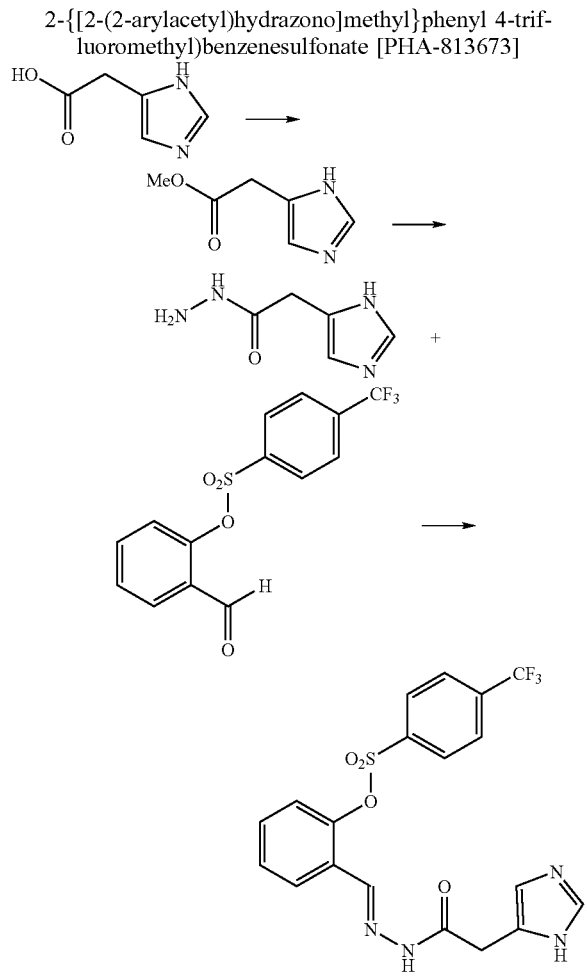

A solution of 4-imidazoleacetic acid (4.2 g, 26 mmol) in methanol (150 mL) is treated with HCl in dioxane (5 mL). The mixture is heated at 60° C. overnight. The solution is evaporated to give a white solid, which is then recrystallized from ether/hexane to yield 4-imidazoleacetic acid methyl ester hydrochloride. The yield is 4.5 g, 98%.

To a solution of 4-imidazoleacetic acid methyl ester hydrochloride (3.95 g, 22.4 mmol) in ethanol (150 ml) is added N,N-diisopropylethylamine (2.90 g, 16.6 mmol) and hydrazine (1.79 g, 36 mmol). The solution is refluxed at 70° C. overnight. The solution is concentrated and recrystallized from methanol to give 4-imidazoleacetic acid hydrazide as a white solid. The yield is 2.46 g, 78%.

A solution of 2-formylphenyl 4-(trifluoromethyl)benzenesulfonate (6.5 g, 19.7 mmol) in ethanol (100 ml) is added to a solution of 4-imidazoleacetic acid hydrazide (18 mmol) in ethanol (200 mL). A catalytic amount of HCl in dioxane (3 mL) is added and the mixture is stirred at room temperature overnight. The precipitate that forms is removed by filtration. The filtrate is concentrated and chromatographed on silica eluting with 5% (2M ammonia in methanol)/ $CH_2Cl_2$ to give 2-((E)-{2-[2-(1H-imidazol-4-yl)acetyl]hydrazono}methyl)phenyl 4-(trifluoromethyl)benzenesulfonate as a white solid. The yield is 3.1 g, 38%. $^1$H NMR (400 MHz, DMSO) d 11.94 (s, 1H), 11.48 (2s, 1H), 8.02 (m, 6H), 7.21 (m, 5H), 3.64 (2 s, 2H). ESI+ for $C_{19}H_{15}F_3N_4O_4S$, m/z 453, (M+H)+.

Example 3 According to Scheme 3

2-((E)-{2-[2-(3-chlorophenyl)acetyl]hydrazono}methyl)phenyl 4-methylbenzenesulfonate [PHA-804389]

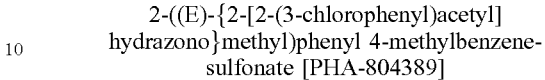

To a solution of 2-(3-chlorophenyl)acetohydrazide (1 g, 5.42 mmol) in absolute EtOH 80 mL and acetic acid 2 mL was added salicylaldehyde (1.323 g, 10.83 mmol). The reaction was stirred at room temperate over night. The reaction mixture was then filtered. The solid was washed with hexane and EtOH. The yield is 1.4 g of 2-(3-chlorophenyl)-N'-[(1E)-(2-hydroxyphenyl)methylidene]acetohydrazide (90%).

To 1 mL pyridine solution of 2-(3-chlorophenyl)-N'-[(1E)-(2-hydroxyphenyl)methylidene]acetohydrazide (86.6 mg, 0.3 mmol) was added 1 mL DCM solution of 4-methylbenzenesulfonyl chloride (114 mg, 0.6 mmol). The reaction was shaken over night and the solvent was removed by evaporation. Water was added to the mixture, sonicated to a fine powder and filtered. The powder was washed with more water. The dried powder is triturated with MeOH to give 1. 2-((E)-{2-[2-(3-chlorophenyl)acetyl]hydrazono}methyl)phenyl 4-methylbenzenesulfonate in 88% yield. $^1$H NMR (400 MHz, DMSO) □ 11.64–11.46 (2s, 1H), 7.98 (m, 2H), 7.71 (m, 2H), 7.28 (m, 8H), 7.12 (m, 1H), 3.95–3.58 (2s, 2H), 2.35–2.30 (2s, 3H). ESI– for $C_{22}H_{19}ClN_2O_4S$: m/z=441 (M–H)–.

Example 4 According to Scheme 4

N'-[(1E)-(2-{[(4-methylphenyl)sulfonyl]methyl}phenyl)methylene]-2-phenylacetohydrazide [PHA-817139]

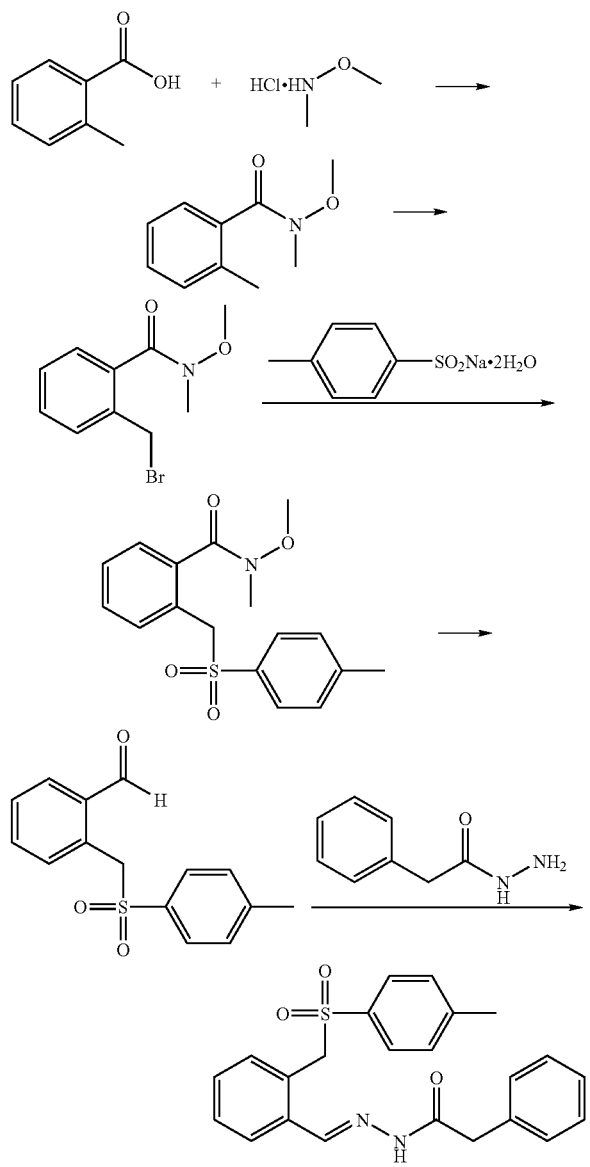

To a premixed solution of 2-methylbenzoic acid (7.5 mmol), EDCl (1.5 mmol) and DMAP (3.0 mmol) in DMA 40 mL and DCM 13 mL is added dimethylhydroxylamine hydrochloride (1.5 mmol). The reaction is stirred at room temperate over night. The reaction mixture is then filtered. The filtrate is diluted with EtOAc and washed with water, 10% $NaHSO_4$ and brine. The solution is dried over $Na_2SO_4$ and the solvent is evaporated. A light yellow oil N-methoxy-N,2-dimethylbenzamide is obtained in 80% yield.

To a solution of N-methoxy-N,2-dimethylbenzamide (1.67 mmol) in $CCl_4$ is added NBS (1.67 mmol) and AIBN (cat. amount). The refluxed mixture is irradiated for 45 min. 1.11 mmol of NBS and a cat. amount of AIBN are added to the mixture and the mixture is then refluxed and irradiated for another 45 min. The reaction mixture is cooled down and filtered. The solution is dried over $Na_2SO_4$ and the solvent is evaporated. The crude oil, 2-(bromomethyl)-N-methoxy-N-methylbenzamide, is used as obtained. A solution of 2-(bromomethyl)-N-methoxy-N-methylbenzamide (1.67 mmol) and p-toluenesulfinic acid sodium salt dihydrate in 10 mL DMA is heated to 100° C. for 5 hr. The reaction mixture is diluted with EtOAc and washed with brine, 10% $NaHSO_4$ and brine again. The solution is dried over $Na_2SO_4$ and the solvent is evaporated. The crude material is purified by flash column chromatography to give a 48% yield of a colorless oil, N-methoxy-N-methyl-2-{[(4-methylphenyl)sulfonyl]methyl}benzamide.

To a solution of N-methoxy-N-methyl-2-{[(4-methylphenyl)sulfonyl]methyl}benzamide (0.645 mmol) in 5 mL THF at –78° C. is added 1.0 M solution of $LiAlH_4$ in THF (0.709 mmol) slowly with stirring. The reaction is stirred at –78° C. for 1 hr and gradually warmed up to RT. The reaction mixture is diluted with EtOAc and washed with $H_2O$. The solution is dried over $Na_2SO_4$ and the solvent is evaporated to give a quantitative yield of 2-{[(4-methylphenyl)sulfonyl]methyl}benzaldehyde.

To a solution of-phenylacetic acid hydrazide (0.24 mmol) in absolute EtOH 10 mL and acetic acid 0.4 mL is added 2-{[(4-methylphenyl)sulfonyl]methyl}benzaldehyde (0.22 mmol). The reaction is stirred at room temperate for 2.5 hr with white ppt formation. The reaction mixture is then filtered. The solid is triturated with MeOH to give N'-[(1E)-(2-{[(4-methylphenyl)sulfonyl]methyl}phenyl)methylene]-2-phenylacetohydrazide in 78% yield. $^1$H NMR (400 MHz, DMSO-$d_6$) □ 11.50–11.25 (2s, 1H), 8.22–8.13 (2s, 1H), 7.79 (m, 1H), 7.56 (m, 2H), 7.31 (m, 10H), 4.93–4.80 (2s, 2H), 3.95–3.57 (2s, 2H), 2.36–2.31 (2s, 3H). ESI– for $C_{23}H_{22}N_2O_3S$, m/z 405 (M–H)–.

Example 5a According to Scheme 5a

N'-{(1E)-[2-(4-methylphenoxy)phenyl]methylene}-2-phenylacetohydrazide [PHA815012]

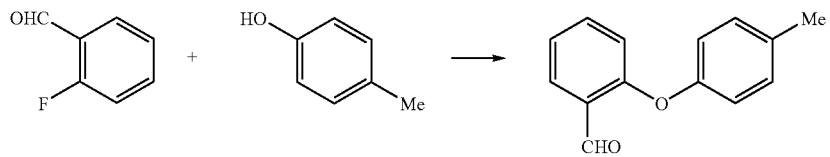

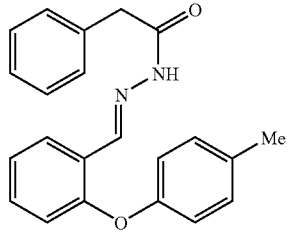
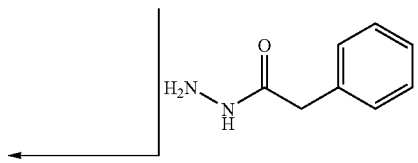

To a solution of 2-fluorobenzaldehyde (3.54 g, 28.5 mmol) in DMA (20 mL) is added p-cresol (3.08 g, 28.5 mmol) and K$_2$CO$_3$ (4.72 g, 34.2 mmol), and the reaction mixture is heated to 150° C. for 12 h. Once complete, the reaction mixture is cooled to room temperature and diluted with water (100 mL) prior to being poured into a separatory funnel containing ethyl acetate (250 mL). The organic layer is separated, washed with brine (2×) and dried over sodium sulfate prior to concentration. The crude product is purified by column chromatography (5% ethyl acetate in hexanes) to afford 2-(4-methylphenoxy)-benzaldehyde (3.05 g, 50%) as a light yellow oil.

To a solution of 2-(4-methylphenoxy)-benzaldehyde (500 mg, 2.36 mmol) in EtOH (10 mL) is added phenyl acetic hydrazide (336 mg, 2.36 mmol) and the reaction is heated to 80° C. for 1 h. While cooling a white precipitate forms, and this solid is isolated by filtration and washed with portions of EtOH and Et$_2$O. This solid is dried under vacuum to provide N'-{(1E)-[2-(4-methylphenoxy)phenyl]methylene}2-phenylacetohydrazide (432 mg, 22%). $^1$H-NMR (400 MHz, DMSO-d$_6$) 11.70–11.55 (m, 1H), 8.51–8.33 (m, 1H), 8.00–7.92 (m, 1H), 7.42–7.19 (m, 9H), 6.91–6.85 (m, 3H), 3.98–3.43 (m, 2H), 2.29 (s, 3H). ESI+ for C$_{22}$H$_{20}$N$_2$O$_2$: m/z=345 (M+H)+.

Example 5b According to Scheme 5b

N'-{(1E)-[2-(1-naphthylmethoxy)phenyl]methylene}-2-phenylacetohydrazide [PHA-846631]

To a solution of 2-hydroxybenzaldehyde (2.30 g, 18.8 mmol) in DMF (20 mL) is added 1-(chloromethyl)-naphthalene (3.36 mL, 22.6 mmol) and K$_2$CO$_3$ (3.11 g, 22.6 mmol), and the reaction mixture is heated to 100° C. for 12 h. Once complete, the reaction mixture is cooled to room temperature and diluted with water (100 mL) prior to being poured into a separatory funnel containing ethyl acetate (250 mL). The organic layer is separated, washed with brine (2×) and dried over sodium sulfate prior to concentration. The crude product is purified by column chromatography (5% ethyl acetate in hexanes) to afford 2-(1-naphthylmethoxy) benzaldehyde (2.13 g, 43%) as a light yellow oil.

To a solution of 2-(1-naphthylmethoxy)benzaldehyde (300 mg, 1.14 mmol) in EtOH (10 mL) is added phenyl acetic hydrazide (172 mg, 1.14 mmol) and the reaction is heated to 80° C. for 1 h. While cooling a white precipitate forms, and this solid is isolated by filtration and washed with portions of EtOH and Et$_2$O. This solid is dried under vacuum to provide N'-{(1E)-[2-(1-naphthylmethoxy)phenyl]methylene-2-phenylacetohydrazide (254 mg, 57%). $^1$H-NMR (400 MHz, DMSO-d$_6$) 11.60–11.55 (m, 1H), 8.43–8.38 (m, 1H), 8.11–7.74 (m, 4H), 7.60–7.56 (m, 2H), 7.44–7.42 (m, 2H), 7.31–7.21 (m, 4H), 7.05–7.04 (m, 1H), 5.65–5.63 (m, 2H), 3.96 (s, 1H), 3.54 (s, 1H), 3.34 (s, 3H). ESI+ for C$_{26}$H$_{22}$N$_2$O$_2$ m/z 395 (M+H)+.

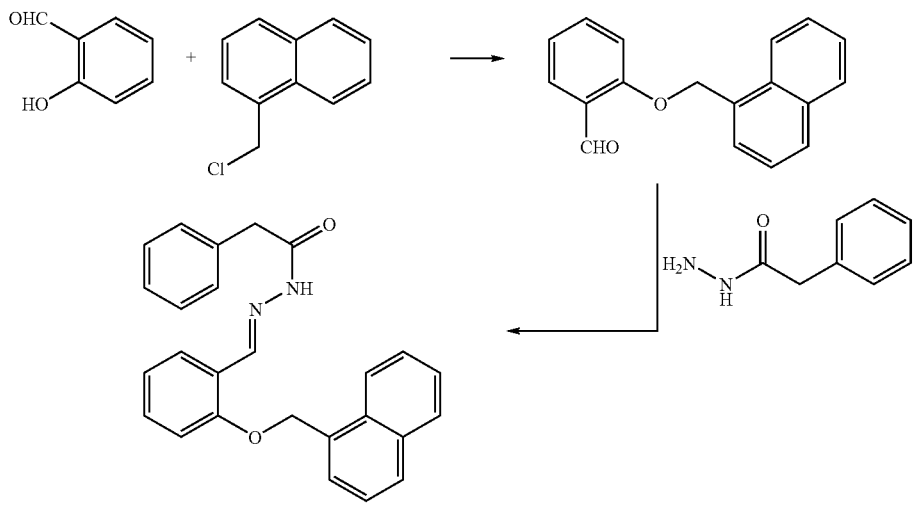

Example 5c According to Scheme 5c 2-(3-methoxyphenyl)-N'-((1E)-{2-[(4-methylphenyl)sulfonyl]phenyl}methylene)acetohydrazide [PHAB15159]

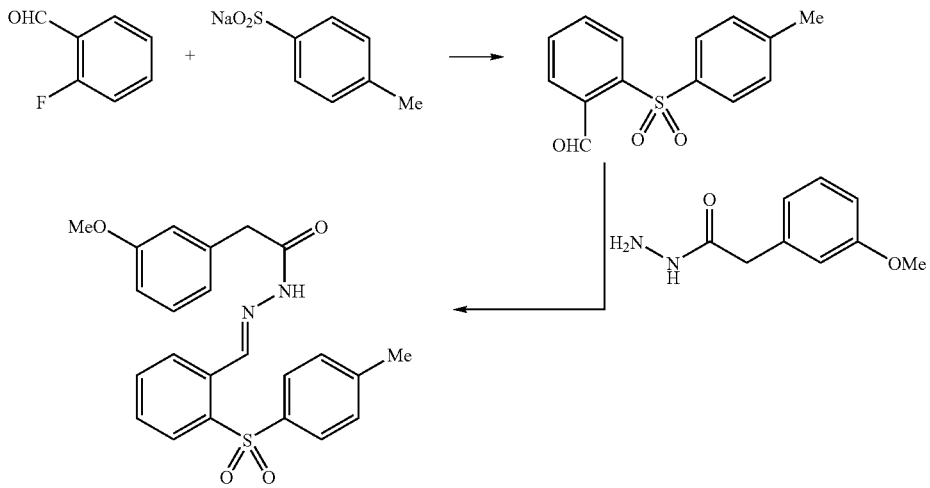

To a solution of 2-fluorobenzaldehyde (12.4 g, 100 mmol) in DMSO (75 mL) is added p-toluenesulfinic acid sodium salt (19.6 g, 110 mmol), and the reaction mixture is heated to 100° C. for 16 h. Once complete, the reaction mixture is cooled to room temperature and poured onto ice. The product is then isolated as a white solid by filtration to afford 2-[(4-methylphenyl)sulfonyl]benzaldehyde (10.1 g, 39%).

To a solution of 2-[(4-methylphenyl)sulfonyl]benzaldehyde (500 mg, 1.92 mmol) in EtOH (10 mL) is added 2-(3-methoxyphenyl)acetohydrazide (329 mg, 1.92 mmol) and the reaction is heated to 80° C. for 1 h. While cooling a white precipitate forms, and this solid is isolated by filtration and washed with portions of EtOH and Et$_2$O. This solid was dried under vacuum to provide 2-(3-methoxyphenyl)-N'-((1E)-{2-[(4-methylphenyl)sulfonyl]phenyl}methylene)acetohydrazide (313 mg, 39%). $^1$H-NMR (400 MHz, DMSO-d$_6$) 12.00–11.85 (m, 1H), 8.95–8.80 (m, 1H), 8.16–8.10 (m, 1H), 7.99–7.81 (2H), 7.72–7.65 (m, 2H), 7.42–7.37 (m, 2H), 7.27–7.16 (m, 1H), 6.93–6.76 (m, 4H), 3.92–3.36 (m, 5H), 2.35 (s, 3H). ESI+ for C$_{23}$H$_{22}$N$_2$O$_4$S, m/z: 423, (M+H)+.

Example 6a According to Scheme 6a

N-[2-((E)-{[(3-chlorophenyl)acetyl]hydrazono}methyl)phenyl]-4-(trifluoromethyl)benzenesulfonamide [PHA-813900]

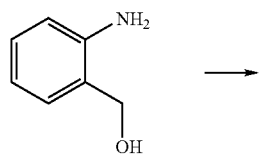

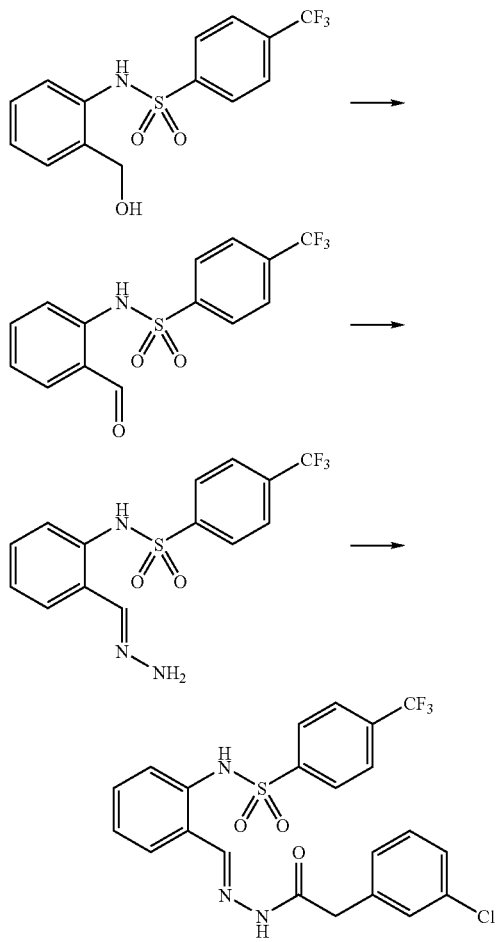

A mixture of THF (20 mL), water (8 mL), sodium bicarbonate (1.0 g), and 4-dimethylaminopyridine (0.5 g) is treated with 2-aminobenzyl alcohol (2.0 g, 16 mmol) and a solution of 4-(trifluoromethylbenzene)sulfonyl chloride (3.0 g, 12 mmol) in THF (4 mL). The reaction is stirred 1 h at room temperature, concentrated, and partitioned between ethyl acetate and 3 N HCl. The organic layer is dried, concentrated, and purified on silica gel in ethyl acetate-methylene chloride mixtures. A yield of 47% (2.5 g) is obtained. The product N-[2-(hydroxymethyl)phenyl]-4-(trifluoromethyl)benzenesulfonamide is crystallized from methylene chloride-hexane.

A solution of N-[2-(hydroxymethyl)phenyl]-4-(trifluoromethyl)benzenesulfonamide (3 g, 9 mmol) in methylene chloride is treated with manganese (IV) oxide (6.6 g, 76 mmol) at room temperature overnight. The reaction is filtered and the product, N-(2-formylphenyl)-4-(trifluoromethyl)benzenesulfonamide, is purified on silica gel eluting with ethyl acetate-methylene chloride and used as obtained.

To a solution of N-(2-formylphenyl)-4-(trifluoromethyl)benzenesulfonamide (0.67 mmol) in ethanol (5 mL) is added to hydrazine hydrate (47 mg, 1.5 mmol) in ethanol (3 mL). The reaction is stirred at room temperature 50 minutes. The reaction is decanted and evaporated, and the product, N-{2-[(E)-hydrazonomethyl]phenyl}-4-(trifluoromethyl)benzenesulfonamide, is used without further purification.

A flask is charged with (3-chlorophenyl)acetic acid (0.34 mmol), 4-dimethylaminopyridine (0.66 mmol), a solution of N-{2-[(E)-hydrazonomethyl]phenyl}-4-(trifluoromethyl)benzenesulfonamide (0.33 mmol) in N,N-dimethylacetamide (1 mL), and 1-ethyl- 3-(3-dimethylaminopropyl)carbodiimide hydrochloride (0.33 mmol). The reaction is stirred at room temperature for 18 hours. The reaction is worked up either by adding water and obtaining a solid precipitate, or by evaporating the reaction mixture. The product is purified on silica gel with ethyl acetate-methylene chloride mixtures. Obtained a 60% yield of N-[2-((E)-{[(3-chlorophenyl)acetyl]hydrazono}methyl)phenyl]-4-(trifluoromethyl)benzenesulfonamide. $^1$H NMR (400 MHz, CDCl$_3$) (mixture of geometric isomers) d 3.73&4.17(2s, 2H); 7.16 (m); 7.36 (m); 7.47 (s); 7.60m; 7.66 (m); 7.75 (m); 7.89 (s); 7.96 (m); 8.06 (m); 9.62 (bs); 10.80 (bs). ESI– for C$_{22}$H$_{17}$ClF$_3$N$_3$O$_3$S: m/z =494 (M–H)–.

Example 6b According to Scheme 6b

N-[2-((E)-[(3,4-dimethoxyphenyl)acetyl]hydrazono}methyl)phenyl]-N-methyl-4-(trifluoromethyl)benzenesulfonamide [PHA-820387]

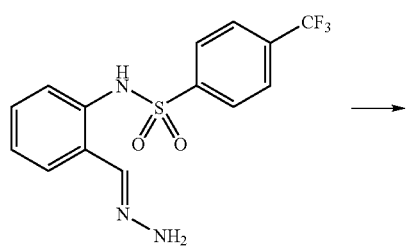

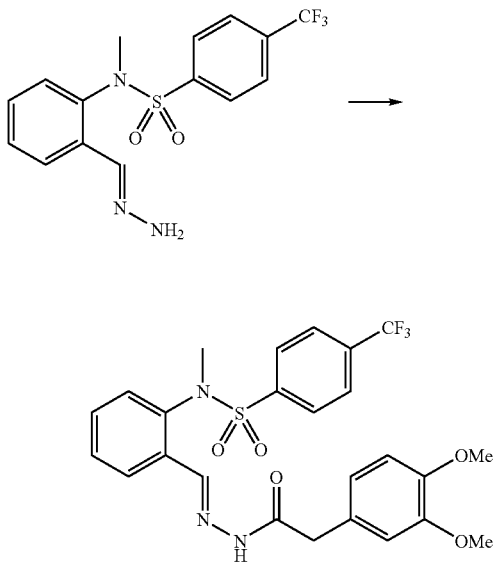

A solution of N-(2-formylphenyl)-4-(trifluoromethyl)benzenesulfonamide (2.2 g, 6.6 mmol) in methanol (11 mL) is treated with a solution of sodium hydroxide (275 mg, 6.9 mmol) in water (2.4 mL). To this is added dimethylsulfate (0.64 mL, 6.8 mmol). The reaction is stirred at rt overnight, evaporated, and chromatographed on silica gel in 5% and 10% ethyl acetate-methylene chloride. The product fractions are further purified by crystallization from toluene-hexane to afford N-(2-formylphenyl)-N-methyl-4-(trifluoromethyl)benzenesulfonamide in 68% yield.

A solution of N-(2-formylphenyl)-N-methyl-4-(trifluoromethyl)benzenesulfonamide (0.40 g, 1.2 mmol) in ethanol (13 mL) is treated with hydrazine monohydrate (69 □L, 1.6 mmol). The reaction is stirred at rt overnight. The reaction is concentrated, taken up in ether-hexane, filtered and evaporated. An 87% yield (0.37 g) of N{2-[hydrazonomethyl]phenyl}-N-methyl-4-(trifluoromethyl)benzenesulfonamide is obtained.

A flask is charged with (3,4-dimethoxyphenyl)acetic acid (0.34 mmol), 4-dimethylaminopyridine (0.66 mmol), a solution of N-{2-[hydrazonomethyl]phenyl}-N-methyl-4-(trifluoromethyl)benzenesulfonamide (0.33 mmol) in N,N-dimethylacetamide (1 mL), and 1-ethyl-3-(3-dimethylaminopropyl)carbodiimide hydrochloride (0.33 mmol). The reaction is stirred at room temperature for 18 hours. The reaction is worked up by evaporating the reaction mixture. The product is purified on silica gel with ethyl acetate-methylene chloride mixtures or methanol-methylene chloride mixtures. A 58% yield of N-[2-((E)-{[(3,4 dimethoxyphenyl)acetyl]hydrazono}methyl)phenyl]-N-methyl-4-(trifluoromethyl)benzenesulfonamide is obtained. $^1$H NMR (400 MHz, CDCl3) (mixture of geometric isomers) d 3.25 (s); 3.90 (2s); 4.10 (m); 6.58 (m); 6.87 (m); 6.96 (m); 7.45 (m); 7.82 (m); 8.20 (m); 8.29 (m); 8.90&8.96 (2bs). ESI– for C$_{25}$H$_{24}$F$_3$N$_3$O$_5$S: m/z=534 (M–H)–.

173

Example 7 According to Scheme 7

2-{(E)-[2-(benzylsulfonyl)hydrazono]methyl}phenyl 4-(trifluoromethyl)benzenesulfonate. [PHA-820539]

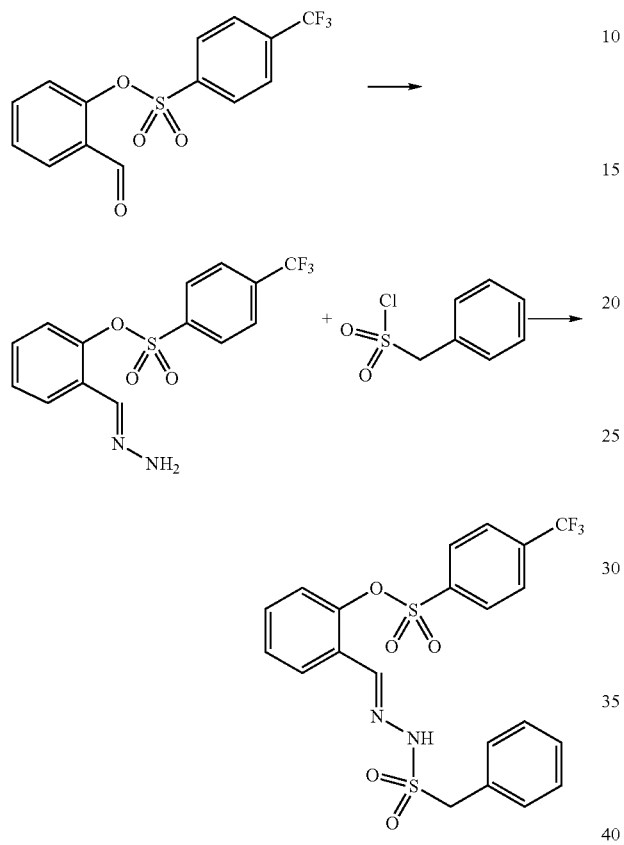

Into a round-bottomed flask are placed hydrazine monohydrate (0.29 mL, 6.06 mmol) and ethanol (5 mL). To this flask a solution of 2-formylphenyl 4-(trifluoromethyl)benzenesulfonate (200 mg, 0.606 mmol) in ethanol (5 mL) is added dropwise over 1 h. The resulting mixture is stirred at rt for 16 h. The solution is concentrated and the product recrystallized form Et$_2$O/Hexane to afford product that is used directly in the next step. The yield is 200 mg of 2-[(E)-hydrazonomethyl]phenyl 4-(trifluoromethyl)benzenesulfonate, 96%.

Into a glass vial are placed 2-[(E)-hydrazonomethyl]phenyl 4-(trifluoromethyl)benzenesulfonate (187 mg, 0.543 mmol) α-toluenesulfonyl chloride (114 mg, 0.597 mmol), and pyridine (5 mL). The resulting mixture is shaken at rt for 16 h. The solution is concentrated and EtOAc is added and the solution washed with water. The organic layer is dried (Na$_2$SO$_4$), concentrated, and isolated by preparative thin layer chromatography (gradient: 20% EtOAc/Hexane 40% EtOAc/Hexane). The yield is 63 mg of 2-{(E)-[2-(benzylsulfonyl)hydrazono]methyl}phenyl 4-(trifluoromethyl)benzenesulfonate, 23%. $^1$H NMR (400 MHz, DMSO-d$_6$): □ 11.51(s, 1H), 8.14–8.12 (m, 2H), 8.09–8.07 (m, 2H), 7.97 (s, 1H), 7.93–7.90 (m, 1H), 7.52–7.43 (m, 2H), 7.38–7.30 (m, 5H), 7.13–7.10 (m, 1H), 4.55 (s, 2H). HRMS for C$_{21}$H$_{17}$F$_3$N$_2$O$_5$S$_2$ m/z 499.0609 (M+H)+.

174

Example 8 According to Scheme 8

2-((1R,2S)-2-{[2-(1,3-benzodioxol-5-yl)acetyl]amino}cyclopropyl)phenyl 4-(trifluoromethyl)benzenesulfonate [PHA-828238]

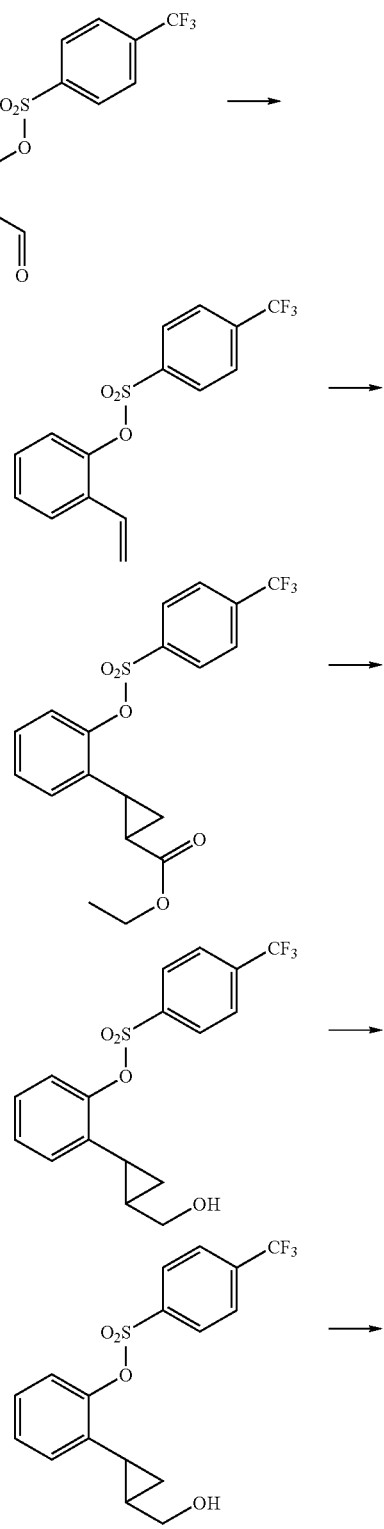

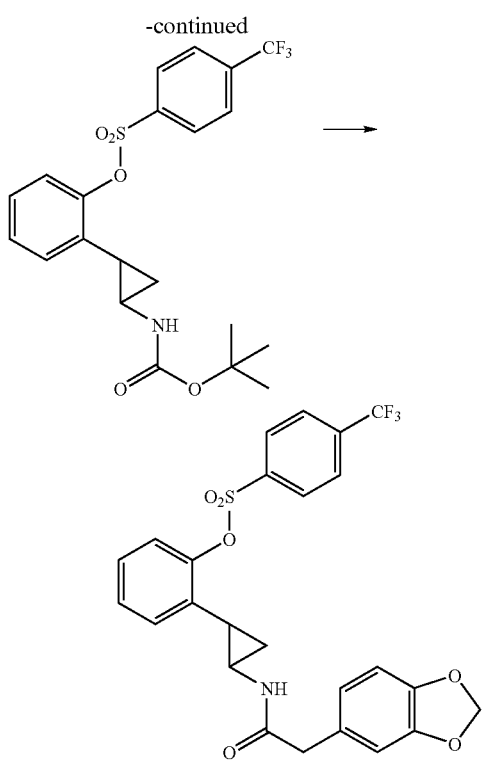

A dry, air-free, ice-cold solution of 2-formylphenyl 4-(trifluoromethyl)-benzenesulfonate (2.0 g, 6.1 mmol) in THF (7 mL) is treated with 6.8 mL of 1 M (trimethylsilylmethyl) magnesium chloride in diethyl ether. The reaction is stirred 30 minutes. Thionyl chloride (0.5 mL, 6.9 mmol) is added and the reaction is stirred at 0° C. for 1 h. The reaction is quenched with ice and extracted with ethyl acetate. The product is purified on silica gel in methylene chloride. A yield of 1.8 g of 2-vinylphenyl 4-(trifluoromethyl)benzenesulfonate is obtained.

A mixture of 2-vinylphenyl 4-(trifluoromethyl)benzenesulfonate (1.8 g, 5.5 mmol) and ethyl diazoacetate (0.70 mL, 6.7 mmol) under argon is heated at 135° C. for 90 min. The product is purified on silica gel in methylene chloride and ethyl acetate-methylene chloride mixtures. The product, ethyl 2-[2-({[4-(trifluoromethyl)phenyl]sulfonyl}oxy)phenyl]cyclopropanecarboxylate, is obtained as a mixture of isomers. A yield of 50% is obtained.

A solution of ethyl 2-[2-({[4-(trifluoromethyl)phenyl]sulfonyl}oxy)phenyl]-cyclopropanecarboxylate (0.84 g, 2.0 mmol) in THF (2 mL) is treated under an inert atmosphere with a 2 M solution of borane-methyl sulfide complex in THF (1 mL). The reaction is heated to 70° C. for 1 h, and stirred at room temperature overnight. The reaction is worked up by partitioning between ethyl acetate and 1 N HCl. The organic layer is dried and evaporated. The product, 2-[2-(hydroxymethyl)cyclopropyl]phenyl 4-(trifluoromethyl)benzenesulfonate, is obtained as a mixture of isomers. A yield of 93% is obtained.

A mixture of 2-[2-(hydroxymethyl)cyclopropyl]phenyl 4-(trifluoromethyl)-benzenesulfonate (0.70 g, 1.9 mmol), carbon tetrachloride (2.5 mL), acetonitrile (2.5 mL), water (3.8 mL), sodium periodate (1.8 g, 8.4 mmol) and ruthenium choride hydrate (75 mg, 0.4 mmol) is stirred at room temperature overnight. The reaction is partitioned between ethyl acetate and dilute HCl. The organic layer is filtered through anhydrous sodium sulfate, evaporated and purified on silica gel in ethyl acetate-methylene chloride-acetic acid mixtures. The product, 2-[2-({[4-(trifluoromethyl)phenyl]sulfonyl}oxy)phenyl]cyclopropanecarboxylic acid, is obtained as a mixture of isomers. A yield of 95% is obtained.

A mixture of 2-[2-({[4-(trifluoromethyl)phenyl]sulfonyl}oxy)phenyl]-cyclopropanecarboxylic acid (0.25 g, 0.64 mmol), t-butyl alcohol (0.76 g, 10.3 mmol), diphenylphosphoryl azide (0.32 g, 1.2 mmol), and triethylamine (0.22 g, 2.2 mmol) is heated under an inert atmosphere to 90° C. for 3 hours, then the reaction is allowed to stir at room temperature overnight. The reaction is diluted with ethyl acetate and washed with 1 N HCl, 5% sodium bicarbonate solution, and brine. The dried, concentrated material is purified by chromatography on silica gel in ethyl acetate-hexane mixtures. The product having trans stereochemistry, 2-{2-[(tert-butoxycarbonyl)amino]cyclopropyl}phenyl 4-(trifluoromethyl)benzenesulfonate, is obtained as the less polar component in 50% yield. It is further purified by crystallization from methylene chloride-hexane.

A solution of 2-{2-[(tert-butoxycarbonyl)amino] cyclopropyl}phenyl 4-(trifluoromethyl)benzenesulfonate (0.09 g, 0.2 mmol) in methylene chloride (1 mL) is treated with trifluoroacetic acid (0.1 mL) at room temperature for 2 hours. The reaction is evaporated in vacuo to a white solid. The solid is treated with N,N-dimethylacetamide (0.3 mL), and triethylamine (27 □L, 0.2 mmol). A mixture of 3,4-(methylenedioxy)phenylacetic acid (39 mg, 0.22 mmol), 4-dimethylaminopyridine (27 mg, 0.22 mmol), and N,N-dimethylacetamide (0.1 mL) is added to the reaction, followed by the addition of 1-ethyl-3-(3-dimethylaminopropyl) carbodiimide (42 mg, 0.22 mmol). The reaction is stirred at room temperature overnight. After work-up with ethyl acetate-hexane-water, the dried, evaporated residue is purified on silica gel in ethyl acetate-methylene chloride mixtures. The product, 2-((1R,2S)-2-{[2-(1,3-benzodioxol-5-yl) acetyl]amino}cyclopropyl)phenyl 4-(trifluoromethyl)-benzenesulfonate, is recrystallized from methanol-water. A yield of 80% is obtained. $^1$H NMR (400 MHz, CDCl3) d 1.15 (m, 1H); 1.25 (m, 1H); 2.07 (m, 1H); 2.80 (m, 1H); 3.50 (s, 2H); 5.97 (m, 3H); 6.78 (m, 4H); 7.05 (m, 1H); 7.13 (m, 1H); 7.21 (m, 1H); 7.85 (m, 2H); 8.02 (m, 2H). ESI+ for $C_{25}H_{20}F_3NO_6S$ m/z=520 (M+H)+.

Example 9 According to Scheme 9

2-({[(pyridin-2-ylmethyl)amino]carbonyl}amino) phenyl 4-(trifluoromethyl)benzenesulfonate [PHA-832262]

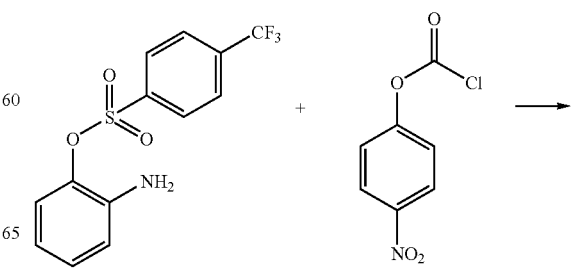

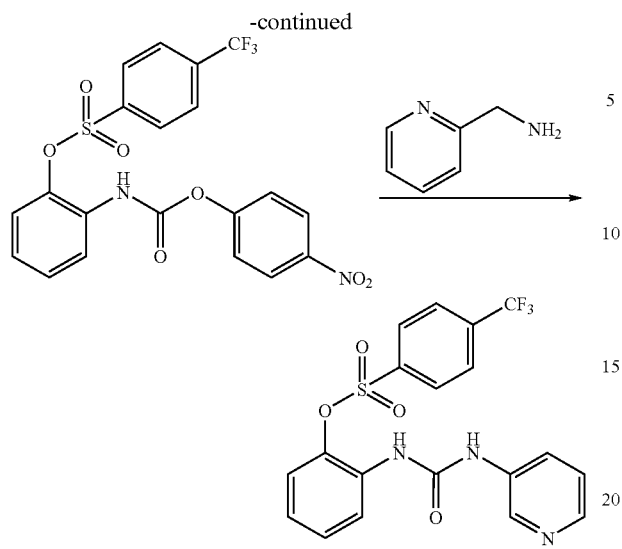

2-Aminophenyl 4-(trifluoromethyl)benzenesulfonate (1.00 mmol, 317 mg) is dissolved in 8 ml CHCl$_3$. 4-Nitrophenyl chloroformate (1.00 mmol, 200 mg) and pyridine (1.00 mmol, 81 μl) are added to the solution. The reaction mixture is heated to 45° C. for an hour. After removing the solvent, 2-{[(4-nitrophenoxy)carbonyl]amino}phenyl 4-(trifluoromethyl)benzenesulfonate is used directly without further purification.

2-{[(4-nitrophenoxy)carbonyl]amino}phenyl 4-(trifluoromethyl)-benzenesulfonate (0.25 mmol, 120 mg) is dissolved in THF, and 2-(aminomethyl)pyridine (0.25 mmol, 26 μl) and Et$_3$N (0.3 mmol, 42 μl) are added to the solution. The reaction mixture is heated at 60° C. for overnight. After purification by preparative HPLC, 2-({[(pyridin-2-ylmethyl)amino]carbonyl}amino)phenyl 4-(trifluoromethyl)benzenesulfonate is obtained in 45% yield. $^1$H NMR (400 MHz, MeOD-d6) 8.54 (d, 1H), 8.01(d, 2H), 7.82(m, 4H), 7.42(d, 1H), 7.34(t, 1H), 7.26(m, 4H), 7.05(t, 1H), 4.41(s, 2H). ESI+ for C$_{20}$H$_{16}$F$_3$N$_3$O$_4$S m/z=452, (M+H)+.

Example 10 According to Scheme 10

2-{(E)-[2-phenylsulfonyl)hydrazono]methyl}phenyl 4-(trifluoromethyl)benzenesulfonate [PHA-643115]

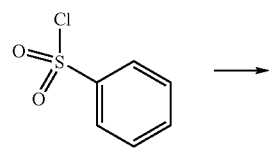

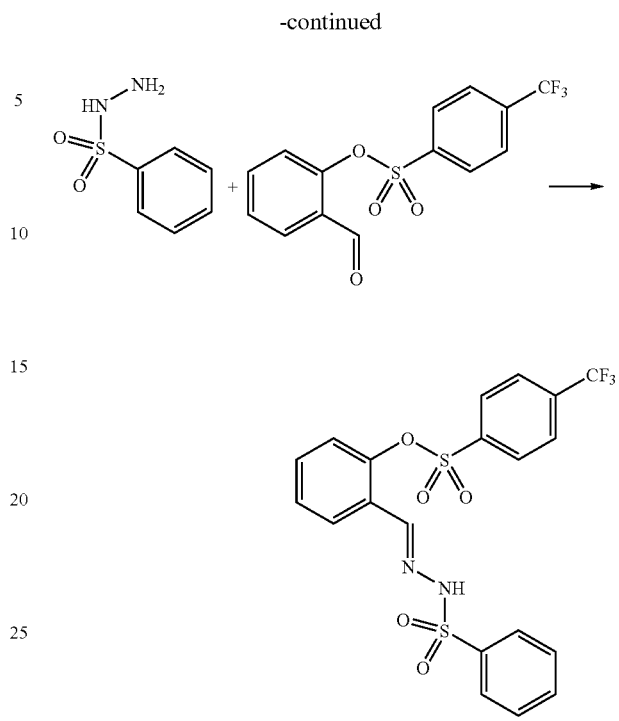

Benzenesulfonohydrazide is prepared from benzenesulfonyl chloride (500 mg, 2.83 mmol) and hydrazine monohydrate (0.42 mL, 8.49 mmol) according to the experimental provided in *Tetrahedron* 2002, 58, 5513. The product is recrystallized from EtOAc/Hexane. The yield is 136 mg of benzenesulfonohydrazide, 28%.

Into a glass vial are placed benzenesulfonohydrazide (78 mg, 0.455 mmol), 2-formylphenyl 4-(trifluoromethyl)benzenesulfonate (100 mg, 0.303 mmol), and ethanol (5 mL). The resulting mixture is shaken at rt for 16 h. The solution is concentrated and the crude product is dissolved in CH$_2$Cl$_2$ (20 mL). To the solution is added polystyrene-benzaldehyde (3.92 g, 4.55 meq.) and the solution is shaken at 40° C. for 3 h. The solution is filtered and concentrated. The yield is 60 mg of 2-{(E)-[2-(phenylsulfonyl)hydrazono]methyl}phenyl 4-(trifluoromethyl)benzenesulfonate, 41%. $^1$H NMR (400 MHz, DMSO-d$_6$): □ 11.76 (s, 1H), 8.10–8.08 (m, 2H), 8.05–8.03 (m, 2H), 7.90 (S, 1H), 7.87–7.85 (m, 2H), 7.72–7.59 (m, 4H), 7.47–7.43 (m, 1H), 7.40–7.36 (m, 1H), 7.10–7.07 (m, 1H). HRMS for C$_{20}$H$_{15}$F$_3$N$_2$O$_5$S$_2$ m/z 485.0467, (M+H)+.

Table II lists the method of preparation based on the above examples and the corresponding proton NMR and mass spectra of the compounds of the invention.

TABLE II

| Compound | Method | $^1$H NMR | LRMS | HRMS | Ion |
|---|---|---|---|---|---|
| 1. | 1 | (DMSO) d 11.64(2s, 1H), 8.50(d, 2H), 8.01(m, 6H), 7.32(m, 5H), 3.78(2s, 2H) | 464 | | (M + H)+ |

TABLE II-continued

| Compound | Method | ¹H NMR | LRMS | HRMS | Ion |
|---|---|---|---|---|---|
| 2. | 1 | (DMSO) d 11.40(2s, 1H), 7.45(m, 6H), 6.84(m, 8H), 2.40(m, 4H) | 477 | | (M + H)⁺ |
| 3. | 1 | (DMSO) d 11.46(2s, 1H), 10.92(2s, 1H), 8.03(m, 6H), 7.27(m, 8H), 3.80(2s, 2H) | 502 | | (M + H)⁺ |
| 4. | 1 | (DMSO) d 11.58(2s, 1H), 8.01(m, 6H), 7.24(m, 6H), 3.93(2s, 2H) | 469 | | (M + H)⁺ |
| 5. | 1 | (DMSO) d 11.94(s, 1H), 11.48(2s, 1H), 8.02(m, 6H), 7.21(m, 5H), 3.64(2s, 2H) | 453 | | (M + H)⁺ |
| 6. | 1 | (DMSO) d 11.64(2s, 1H), 8.50(d, 2H), 8.01(m, 6H), 7.32(m, 5H), 3.78(2s, 2H) | 464 | | (M + H)+ |
| 7. | 1 | (DMSO) d 11.55(2s, 1H), 7.99(m, 6H), 7.32(m, 7H), 3.71(2s, 2H) | 498 | | (M + H)+ |
| 8. | 1 | (DMSO) d 11.53(2s, 1H), 7.99(m, 6H), 7.31(m, 7H), 3.72(2s, 2H) | 481 | | (M + H)+ |
| 9. | 1 | (DMSO) d 11.57(2s, 1H), 7.99(m, 6H), 7.33(m, 6H), 3.74(2s, 2H) | 515 | | (M + H)+ |
| 10. | 1 | (DMSO) d 11.63(2s, 1H), 8.02(m, 6H), 7.32(m, 6H), 3.87(2s, 2H) | 515 | | (M + H)+ |
| 11. | 1 | (DMSO) d 11.43(2s, 1H), 8.00(m, 6H), 7.45(m, 2H), 7.12(m, 3H), 6.68(m, 2H), 3.65(2s, 2H), 2.85(s, 3H), 2.83(s, 3H) | 506 | | (M + H)+ |
| 12. | 1 | (DMSO) d 11.77(2s, 1H), 7.99(m, 6H), 7.49(m, 2H), 7.21(m, 1H), 3.91(2s, 2H) | 551 | | (M − H)− |
| 13. | 1 | (DMSO) d 11.59(2s, 1H), 7.99(m, 6H), 7.68(m, 2H), 7.47(m, 3H), 7.19(m, 1H), 3.84(2s, 2H) | 547 | | (M − H)− |
| 14. | 1 | (DMSO) d 11.64(2s, 1H), 7.95(m, 7H), 7.42(m, 4H), 7.18(m, 1H), 3.88(2s, 2H) | 547 | | (M − H)− |
| 15. | 1 | (DMSO) d 11.50(2s, 1H), 8.04(m, 6H), 7.46(m, 2H), 7.16(m, 1H), 6.85(m, 2H), 3.63(m, 11H) | 551 | | (M − H)− |
| 16. | 1 | (DMSO) d 11.65(2s, 1H), 8.00(m, 6H), 7.47(m, 2H), 7.24(m, 3H), 3.84(2s, 2H) | 515 | | (M − H)− |
| 17. | 1 | (DMSO) d 11.63(2s, 1H), 8.01(m, 6H), 7.51(m, 4H), 7.17(m, 1H), 3.78(2s, 2H) | 515 | | (M − H)− |
| 18. | 1 | (DMSO) d 11.60(2s, 1H), 8.00(m, 6H), 7.47(m, 4H), 7.21(m, 1H), 3.77(2s, 2H) | 515 | | (M − H)− |
| 19. | 1 | (DMSO) d 11.61(2s, 1H), 8.09(m, 6H), 7.57(m, 6H), 7.17(m, 1H), 3.81(2s, 2H) | 561 | | (M − H)− |
| 20. | 1 | (DMSO) d 11.67(2s, 1H), 8.01(m, 6H), 7.47(m, 3H), 7.16(m, 2H), 3.87(2s, 2H) | 515 | | (M − H)− |
| 21. | 1 | (DMSO) d 11.58(2s, 1H), 8.00(m, 6H), 7.33(m, 7H), 3.80(2s, 2H) | 545 | | (M − H)− |
| 22. | 1 | (DMSO) d 11.28(2s, 1H), 8.65(m, 6H), 7.97(m, 4H), 7.64(m, 1H), 4.78(2s, 2H) | 567 | | (M + H)+ |
| 23. | 1 | (DMSO) d 11.19(2s, 1H), 8.64(m, 6H), 7.81(m, 6H), 4.47(2s, 2H) | 547 | | (M − H)− |
| 24. | 1 | (DMSO) d 11.03(2s, 1H), 8.65(m, 6H), 7.61(m, 6H), 4.28(m, 8H) | 521 | | (M − H)− |
| 25. | 1 | (DMSO) d 11.20(2s, 1H), 8.65(m, 6H), 7.93(m, 7H), 4.67(2s, 2H) | 561 | | (M − H)− |
| 26. | 1 | (DMSO) d 11.52(2s, 1H), 8.01(m, 6H), 7.46(m, 2H), 7.19(m, 5H), 3.67(2s, 2H), 2.46(2s, 3H) | 507 | | (M − H)− |
| 27. | 1 | (DMSO) d 11.70(2s, 1H), 7.99(m, 6H), 7.47(m, 3H), 7.19(m, 2H), 3.85(2s, 2H) | 515 | | (M − H)− |
| 28. | 1 | (DMSO) d 11.66(2s, 1H), 7.99(m, 6H), 7.30(m, 6H), 3.79(2s, 2H) | 497 | | (M − H)− |
| 29. | 1 | (DMSO) d 11.62(2s, 1H), 8.13(m, 8H), 7.30(m, 5H), 3.90(2s, 2H) | 462 | | (M − H)− |
| 30. | 1 | (DMSO) d 11.38(2s, 1H), 8.08(m, 9H), 7.30(m, 4H), 2.91(2s, 2H) | 476 | | (M − H)− |
| 31. | 1 | (DMSO) d 11.63(2s, 1H), 8.01(m, 6H), 7.33(m, 6H), 3.76(2s, 2H) | 497 | | (M − H)− |
| 32. | 1 | (DMSO) d 11.70(2s, 1H), 8.02(m, 9H), 7.34(m, 3H), 4.12(2s, 2H) | 597 | | (M − H)− |
| 33. | 1 | (DMSO) d 11.68(2s, 1H), 7.99(m, 6H), 7.39(m, 6H), 4.00(2s, 2H) | 547 | | (M − H)− |
| 34. | 1 | (DMSO) d 11.61(2s, 1H), 7.66(m, 13H), 3.84(2s, 2H) | 529 | | (M − H)− |
| 35. | 1 | (DMSO) d 11.59(2s, 1H), 8.00(m, 6H), 7.42(m, 7H), 3.86(2s, 2H) | 529 | | (M − H)− |
| 36. | 1 | (DMSO) d 11.48(2s, 1H), 8.03(m, 6H), 7.18(m, 7H), 3.80(m, 5H) | 491 | | (M − H)− |

TABLE II-continued

| Compound | Method | ¹H NMR | LRMS | HRMS | Ion |
|---|---|---|---|---|---|
| 37. | 1 | (DMSO) d 11.48(2s, 1H), 7.48(m, 12H), 3.76(m, 8H) | 521 | | (M − H)− |
| 38. | 1 | (DMSO) d 11.58(2s, 1H), 8.00(m, 6H), 7.37(m, 6H), 3.76(2s, 2H) | 530 | | (M − H)− |
| 39. | 1 | (DMSO) d 11.65(2s, 1H), 7.99(m, 9H), 7.54(m, 3H), 4.02(2s, 2H) | 597 | | (M − H)− |
| 40. | 1 | (DMSO) d 11.65(2s, 1H), 8.05(m, 6H), 7.38(m, 7H), 3.91(2s, 2H) | 540 | | (M − H)− |
| 41. | 1 | (DMSO) d 11.60(2s, 1H), 8.02(m, 6H), 7.32(m, 7H), 3.78(2s, 2H) | 479 | | (M − H)− |
| 42. | 1 | (DMSO) d 11.54(2s, 1H), 8.03(m, 6H), 7.31(m, 7H), 3.74(2s, 2H), 2.26(2s, 3H) | 475 | | (M − H)− |
| 43. | 1 | (DMSO) d 11.48(2s, 1H), 8.01(m, 6H), 7.12(m, 6H), 5.99(2s, 2H), 3.62(2s, 2H) | 505 | | (M − H)− |
| 44. | 1 | (DMSO) d 11.48(2s, 1H), 8.01(m, 6H), 7.19(m, 7H), 3.78(2s, 2H) | 491 | | (M − H)− |
| 45. | 1 | (DMSO) d 11.28(2s, 1H), 7.95(m, 6H), 7.32(m, 3H), 2.23(m, 2H), 1.32(m, 10H) | 467 | | (M − H)− |
| 46. | 1 | (DMSO) d 11.30(2s, 1H), 7.88(m, 6H), 7.32(m, 8H), 2.62(m, 2H), 2.54(m, 2H), 1.85(m, 2H) | 489 | | (M − H)− |
| 47. | 1 | (DMSO) d 11.28(2s, 1H), 7.93(m, 6H), 7.31(m, 8H), 2.62(m, 2H), 2.52(m, 2H), 1.60(m, 4H) | 503 | | (M − H)− |
| 48. | 1 | (DMSO) d 11.56(2s, 1H), 8.09(m, 4H), 7.49(m, 9H), 3.75(2s, 2H) | 481 | | (M + H)+ |
| 49. | 1 | (DMSO) d 11.48(2s, 1H), 10.77(2s, 1H), 8.05(m, 6H), 7.26(m, 6H), 6.73(m, 1H), 3.77(2s, 2H), 3.70(2s, 3H) | 530 | | (M − H)− |
| 50. | 1 | (DMSO) d 11.50(2s, 1H), 8.02(m, 6H), 7.31(m, 3H), 6.46(m, 3H), 3.72(s, 6H) | 521 | | (M − H)− |
| 51. | 1 | (DMSO) d 11.42(2s, 1H), 8.03(m, 6H), 7.26(m, 3H), 6.51(m, 2H), 3.60(m, 8H) | 521 | | (M − H)− |
| 52. | 1 | (DMSO) d 11.56(2s, 1H), 8.01(m, 6H), 7.48(m, 4H), 7.20(m, 3H), 3.71(2s, 2H) | 540 | | (M − H)− |
| 53. | 1 | (DMSO) d 11.63(d, 1H), 8.10(m, 6H), 7.33(m, 4H), 6.56(m, 3H), 3.71(2s, 2H) | 507 | | (M − H)− |
| 54. | 1 | (DMSO) d 11.41(2s, 1H), 7.62(m, 10H), 6.23(m, 2H), 2.88(m, 4H) | 465 | | (M − H)− |
| 55. | 1 | (DMSO) d 11.51(2s, 1H), 8.02(m, 6H), 6.99(m, 5H), 3.65(m, 11H) | 551 | | (M − H)− |
| 56. | 1 | (DMSO) d 11.53(2s, 1H), 7.54(m, 18H), 5.11(d, 2H), 3.76(2s, 2H) | 567 | | (M − H)− |
| 57. | 1 | (DMSO) d 11.51(2s, 1H), 7.51(m, 18H), 3.77(2s, 2H) | 553 | | (M − H)− |
| 58. | 1 | (DMSO) d 11.36(2s, 1H), 7.94(m, 6H), 7.12(m, 7H), 3.73(2s, 3H), 2.81(m, 4H) | 505 | | (M − H)− |
| 59. | 1 | (DMSO) d 11.66(2s, 1H), 8.02(m, 6H), 7.30(m, 8H), 3.77(2s, 2H) | 493 | | (M − H)− |
| 60. | 1 | (DMSO) d 11.55(2s, 1H), 8.01(m, 6H), 7.39(m, 7H), 3.68(m, 2H) | 587 | | (M − H)− |
| 61. | 1 | (DMSO) d 11.64(2s, 1H), 8.24(m, 9H), 7.33(m, 3H), 3.83(2s, 2H) | 542 | | (M − H)− |
| 62. | 1 | (DMSO) d 11.57(2s, 1H), 8.01(m, 6H), 7.33(m, 7H), 3.74(2s, 2H) | 541 | | (M − H)− |
| 63. | 1 | (DMSO) d 11.62(2s, 1H), 8.05(m, 8H), 7.32(m, 4H), 3.81(2s, 2H) | 498 | | (M − H)− |
| 64. | 1 | (DMSO) d 11.63(2s, 1H), 8.10(m, 6H), 7.21(m, 8H), 4.85(2s, 2H) | 477 | | (M − H)− |
| 65. | 1 | (DMSO) d 11.61(2s, 1H), 8.04(m, 7H), 7.26(m, 7H), 4.00(m, 2H), 3.98(2s, 2H) | 501 | | (M − H)− |
| 66. | 1 | (DMSO) d 11.63(2s, 1H), 8.02(m, 6H), 7.30(m, 3H), 6.24(d, 2H), 3.61(2s, 2H) | 551 | | (M − H)− |
| 67. | 1 | (DMSO) d 11.47(2s, 1H), 8.01(m, 6H), 7.18(m, 7H), 4.00(m, 2H), 3.62(2s, 2H), 1.31(m, 3H) | 505 | | (M − H)− |
| 68. | 1 | (DMSO) d 11.60(2s, 1H), 8.01(m, 10H), 7.47(m, 5H), 7.17(m, 1H), 3.90(2s, 2H) | 511 | | (M − H)− |
| 69. | 1 | (DMSO) d 11.64(2s, 1H), 8.02(m, 8H), 7.35(m, 5H), 3.87(2s, 2H), 3.21(2s, 3H) | 539 | | (M − H)− |
| 70. | 1 | (DMSO) d 11.52(2s, 1H), 8.04(m, 6H), 7.23(m, 6H), 3.71(2s, 2H), 3.77(2s, 3H) | 569 | | (M − H)− |
| 71. | 2 | DMSO: 12.07(s, 1H), 8.34(s, 1H), 8.22–8.20(m, 1H), 8.14–8.12(m, 1H), 8.09–7.99(m, 6H), 7.75–7.74(m, 1H), 7.67–7.47(m, 5H), 7.21–7.19(m, 1H) | | 499.0942 | (M + H)+ |

TABLE II-continued

| Compound | Method | ¹H NMR | LRMS | HRMS | Ion |
|---|---|---|---|---|---|
| 72. | 2 | DMSO: 12.15–12.07(m, 1H), 8.29(s, 0.6H), 8.10(m, 0.4H), 8.08–8.03(m, 4H), 7.97–7.95(m, 0.5H), 7.70(m, 0.5H), 7.64(m, 1H), 7.57–7.42(m, 3H), 7.34–7.28(m, 1H), 7.17–7.14(m, 1H) | | 517.0003 | M+ |
| 73. | 2 | DMSO: 12.02–12.00(m, 1H), 8.29(s, 0.6H), 8.09–8.03(m, 4H), 8.00(s, 0.4H), 7.97–7.94(m, 0.6H), 7.62–7.36(m, 5.7H), 7.29–7.28(m, 0.7H), 7.18–7.15(m, 1H) | | 483.0382 | (M + H)+ |
| 74. | 2 | DMSO: 12.10–12.03(m, 1H), 8.29(s, 0.5H), 8.09–8.04(m, 4H), 8.02(s, 0.5H), 7.97–7.94(m, 0.5H), 7.82–7.81(m, 0.5H), 7.73–7.72(m, 0.5H), 7.61(m, 1H), 7.54–7.50(m, 1H), 7.49–7.41(m, 1.5H), 7.33–7.32(m, 1H), 7.17–7.14(m, 1H) | | 516.9994 | (M − H)− |
| 75. | 2 | DMSO: 11.31–11.24(m, 1H), 8.06–8.00(m, 4H), 7.91(s, 1H), 7.80–7.78(m, 1H), 7.50–7.45(m, 1H), 7.43–7.35(m, 6H), 7.21–7.19(m, 1H), 5.17(s, 2H) | | 479.0879 | (M + H)+ |
| 76. | 2 | DMSO: 12.01(s, 1H), 9.06–9.05(m, 1H), 8.80–8.79(m, 1H), 8.38(s, 1H), 8.26–8.23(m, 1H), 8.08–8.03(m, 4H), 7.94–7.91(m, 1H), 7.62–7.59(m, 1H), 7.55–7.51(m, 1H), 7.49–7.45(m, 1H), 7.20–7.18(m, 1H) | | 450.0728 | |
| 77. | 2 | DMSO: 12.17–12.12(m, 1H), 8.31 - (m, 0.3H), 8.19–8.15(m, 1H), 8.11–8.03(m, 4H), 7.98–7.86(m, 2H), 7.84–7.73(m, 1.5H), 7.61–7.59(m, 0.7H), 7.54–7.41(m, 1.5H), 7.32–7.29(0.5H), 7.23–7.21(m, 0.5H), 715–7.11(m, 1H) | | 494.0635 | (M + H)+ |
| 78. | 2 | DMSO: 11.68(m, 1H), 8.10–8.08(m, 2H), 8.05–8.03(m, 2H), 7.89(s, 1H), 7.75–7.70(m, 2H), 7.47–7.36(m, 4H), 7.10–7.08(m, 1H), 2.36(s, 3H) | | 499.06 | (M + H)+ |
| 79. | 2 | DMSO: 11.56(s, 1H), 8.38(m, 1H), 8.10–8.08(m, 2H), 8.03–8.01(m, 2H), 7.90–7.89(m, 1H), 7.81–7.79(m, 2H), 7.50–7.42(m, 2H), 7.17–7.15(m, 1H), 6.78–6.76(m, 2H), 3.02(m, 6H) | | 492.1187 | (M + H)+ |
| 80. | 2 | (DMSO) 11.27(d, 1H), 8.04(m, 4.5), 7.82(m, 1.5), 7.45(m, 2H), 7.17(s, 1H), 2.40–1.78(m, 5H), 1.54–1.00(m, 8H) | 481.0 | | (M + H)+ |
| 81. | 2 | DMSO: 10.46(d, 1H), 7.97(m, 4H), 7.53–7.13(m, 8H), 3.77(m, 2H), 2.02(m, 3H) | | 511.0696 | (M + H)+ |
| 82. | 2 | DMSO: 11.98–11.89(m, 1H), 9.29–9.26(m, 1H), 8.89–8.88(m, 2H), 8.21(s, 0.2H), 8.08–8.07(m, 4H), 7.95(s, 0.8H), 7.89–7.82(m, 1H), 7.53–7.35(m, 2H), 7.18–7.11(m, 1H), 4.54–4.25(m, 2H) | | 533.0848 | (M + H)+ |
| 83. | 2 | DMSO: 12.03–12.00(m, 1H), 8.63–8.53(m, 1H), 8.35(s, 0.7H), 8.10–8.05(m, 4H), 8.03(s, 0.3H), 7.96–7.94(m, 0.7H), 7.90–7.89(m, 0.7H), 7.64–7.20(m, 3.6H), 7.15–7.13(m, 1H), 2.49(s, 3H) | | 496.0587 | (M + H)+ |
| 84. | 2 | (DMSO) 11.27(d, 1H), 8.04(m, 4.5H), 7.87–7.72(m, 1.5H), 7.54–7.38(m, 2H), 7.29–7.07(m, 1H), 2.18(m, 2H), 1.74(m, 2H), 1.55(m, 4H), 1.15(m, 2H) | | 455.1239 | (M + H)+ |
| 85. | 2 | DMSO: 11.69–11.58(m, 1H), 8.32(s, 0.8H), 8.13–8.03(m, 4H), 8.00(s, 0.2H), 7.96–7.94(m, 0.8H), 7.58–7.55(m, 0.8H), 7.52–7.43(m, 2.4H), 7.42–7.38(m, 0.5H), 7.33–7.26(m, 0.5H), 7.22–7.12(m, 2H), 7.08–6.95(m, 1H), 4.18–3.96(m, 2H), 1.39–1.05(m, 3H) | | 493.1048 | (M + H)+ |
| 86. | 2 | DMSO: 11.60–11.59(m, 1H), 8.36(s, 0.4H), 8.09–7.85(m, 5.6H), 7.51–7.47(m, 1H), 7.44–7.41(m, 1H), 7.20–7.03(m, 2H), 6.39–6.30(m, 2H), 6.23–6.17(m, 1H), 4.97–4.60(m, 2H), 2.90(s, 3H), 2.86(s, 3H) | 522.0 | | (M + H)+ |

TABLE II-continued

| Compound | Method | ¹H NMR | LRMS | HRMS | Ion |
|---|---|---|---|---|---|
| 87. | 2 | DMSO: 11.70–11.51(m, 1H), 8.27(s, 0.8H), 8.10–8.01(m, 4H), 7.96(s, 0.2H), 7.92–7.90(m, 0.8H), 7.57–7.28(m, 4H), 7.21–7.18(m, 1.8H), 7.14–7.12(m, 0.2H), 7.09–7.06(m, 1H), 7.01–6.97(m, 0.2H), 3.91–3.70(m, 3H) | 478.9 | | (M + H)+ |
| 88. | 2 | DMSO: 12.02–11.99(m, 1H), 8.30(m, 0.6H), 8.10–8.04(m, 4H), 8.02(m, 0.4H), 7.97–7.95(m, 0.6H), 7.76–7.66(m, 1H), 7.54–7.29(m, 5.4H), 7.17–7.13(m, 1H) | 526.8/ 528.8 | | (M + H)+ |
| 89. | 2 | DMSO: 12.34–12.23(m, 1H), 9.03–8.93(m, 1.5H), 8.76(s, 0.5H), 8.28(s, 0.5H), 8.08–8.03(m, 4.5H), 7.98–7.94(m, 1H), 7.89–7.87(m, 0.5H), 7.56–7.52(m, 0.5H), 7.49–7.42(m, 1H), 7.29–7.25(m, 0.5H), 7.19–7.17(m, 1.5H) | 517.9 | | (M + H)+ |
| 90. | 2 | DMSO: 11.96–11.88(m, 1H), 8.28(s, 0.7H), 8.07–8.02(m, 4H), 7.96(s, 0.3H), 7.93–7.91(m, 0.6H), 7.67–7.60(m, 1.4H), 7.56–7.26(m, 5H), 7.20–7.18(m, 1H) | 466.9 | | (M + H)+ |
| 91. | 2 | DMSO: 11.55–11.49(m, 1H), 8.10(m, 0.3H), 8.06–8.00(m, 4H), 7.87(s, 0.7H), 7.85–7.79(m, 1H), 7.51–7.46(m, 1H), 7.44–7.33(m, 3H), 7.30–7.10(m, 4H), 4.44–4.35(m, 2H), 3.88–3.80(m, 0.7H), 3.54–3.46(m, 1H), 3.32–3.28(m, 1H), 3.32–3.15(m, 0.3H), 2.65–2.54(m, 2H) | | 546.1325 | (M + H)+ |
| 92. | 2 | DMSO: 11.98–11.93(m, 1H), 8.60–8.48(m, 1H), 8.28(s, 0.7H), 8.08–8.04(m, 4.3H), 8.00(s, 0.3H), 7.96–7.94(m, 0.7H), 7.86–7.83(m, 0.6H), 7.67–7.63(m, 0.4H), 7.55–7.50(m, 0.5H), 7.48–7.45(m, 1H), 7.40–7.37(m, 0.5H), 7.33–7.24(m, 1H), 7.20–7.17(m, 1H), 2.56–2.35(m, 3H) | | 464.0882 | (M + H)+ |
| 93. | 2 | DMSO: 12.07(s, 1H), 8.57–8.56(m, 1H), 8.49(s, 1H), 8.11–8.09(m, 2H), 8.03–8.01(m, 2H), 7.93–7.91(m, 1H), 7.84–7.82(m, 1H), 7.56–7.43(m, 3H), 7.21–7.19(m, 1H), 2.55(s, 3H) | | 464.0882 | (M + H)+ |
| 94. | 2 | (DMSO) 11.25(m, 1H), 8.02(m, 4.5H), 7.82(m, 1.5H), 7.46(m, 2H), 7.19(m, 1H), 2.34–1.82(m, 6H), 1.73–1.49(m, 10H) | 521 | | (M + H)+ |
| 95. | 2 | (DMSO) 11.36(d, 1H), 8.14–8.00(m, 4.5H), 7.84(m, 1.5H), 7.42(m, 2H), 7.17(m, 1H), 4.16(m, 1H), 3.75(m, 1H), 3.59(m, 1H), 2.92–2.53(m, 1H), 2.36(m, 1H), 1.99(m, 1H), 1.83(m, 1H), 1.52(m, 1H) | 456.9 | | (M + H)+ |
| 96. | 2 | 1H NMR(DMSO) d 11.33(s, 1H) 8.36(m, 2H) 8.08(m, 1H) 7.95(m, 2H) 7.78(m, 1H) 7.52(m, 1H) 7.26(m, 1H) 7.19(m, 1H), 7.15(m, 2H), 7.10(m, 1H) 7.03(m, 1H) 6.82(m, 1H), 6.77(m, 1H) 6.70(m, 2H) 5.1(m, 1H) 4.15(d, 2H) 3.71(m, 5H) | 598 | | (M + H)+ |
| 97. | 2 | 1H NMR(DMSO) d 11.44(s, 1H) 8.07(m, 6H) 7.24(m, 9H) 6.26(m, 2H) 4.05(s, 2H) | 528 | | (M + H)+ |
| 98. | 2 | 1H NMR(DMSO) d 11.33(s, 1H) 8.02(m, 6H) 7.45(m, 2H) 7.14(m, 2H) 6.47(m, 3H) 3.79(s, 2H) 3.16(m, 4H) 1.92(m, 4H) | 532 | | (M + H)+ |
| 99. | 2 | 1H NMR(DMSO) d 11.33(s, 1H) 9.85(s, 1H) 8.36(m, 2H) 8.08(m, 1H) 7.95(m, 2H) 7.78(m, 1H) 7.51(m, 1H) 7.31(m, 2H) 7.29(m, 2H), 7.25(m, 1H) 7.15(m, 3H) 6.82(m, 1H) 6.7(m, 1H) 6.13(bs, 1H) 4.15(d, 2H), 3.75(s, 2H) 2.18(s, 3H) | 625 | | (M + H)+ |
| 100. | 2 | DMSO: 11.80(s, 1H), 8.27(s, 1H), 8.08–8.03(m, 4H), 7.97–7.93(m, 1H), 7.53–7.41(m, 3H), 7.34–7.19(m, 4H), 2.37(s, 3H) | | 463.0943 | (M + H)+ |

TABLE II-continued

| Compound | Method | ¹H NMR | LRMS | HRMS | Ion |
|---|---|---|---|---|---|
| 101. | 2 | DMSO: 11.29(s, 0.5H), 11.07(s, 0.5H), 8.09(s, 0.5H), 8.07–7.99(m, 4H), 7.84–7.82(m, 1H), 7.78–7.76(m, 0.5H), 7.51–7.40(m, 2H), 7.26–7.13(m, 1H), 3.00–2.91(m, 0.5H), 2.20–2.12(m, 0.5H), 1.79–1.61(m, 5H), 1.44–1.15(m, 5H) | | 455.123 | (M + H)+ |
| 102. | 2 | DMSO: 12.24–12.20(m, 1H), 8.23(s, 0.5H), 8.07–8.01(m, 4.5H), 7.95–7.92(m, 0.5H), 7.68–7.52(m, 1.5H), 7.49–7.43(m, 1H), 7.33–7.27(m, 2H), 7.22–7.17(m, 2H) | | 485.0577 | (M + H)+ |
| 103. | 2 | DMSO: 12.32–12.24(m, 1H), 8.23(s, 0.4H), 8.08–8.00(m, 4.6H), 7.97–7.95(m, 0.4H), 7.84–7.65(m, 3H), 7.56–7.52(m, 0.4H), 7.49–7.41(m, 1H), 7.29–7.25(m, 0.6H), 7.21–7.16(m, 1.6H) | 534.8 | | (M + H)+ |
| 104. | 2 | DMSO: 12.08–12.04(m, 1H), 8.28(m, 0.5H), 8.08–8.02(m, 4H), 7.99(s, 0.5H), 7.97–7.94(m, 0.5H), 7.90–7.88(m, 0.5H), 7.85–7.72(m, 2H), 7.69–7.65(m, 1H), 7.55–7.51(m, 0.5H), 7.49–7.39(m, 1.5H), 7.27–7.24(m, 0.5H), 7.20–7.16(m, 1.5H) | 516.9 | | (M + H)+ |
| 105. | 2 | DMSO: 11.70(s, 1H), 8.10–8.08(m, 2H), 8.06–8.04(m, 2H), 7.89(s, 1H), 7.77–7.75(m, 2H), 7.73–7.71(m, 1H), 7.47–7.43(m, 3H), 7.40–7.37(m, 1H), 7.10–7.07(m, 1H), 2.7–2.64(m, 2H), 1.19–1.15(m, 3H) | 512.9 | | (M + H)+ |
| 106. | 2 | (DMSO) d 11.45(2s, 1H), 8.01(m, 6H), 7.20(m, 5H), 3.56(2s, 2H), 3.61(m, 3H) | 465 | | (M − H)− |
| 107. | 2 | (DMSO) d 12.03(2s, 1H), 8.06(m, 6H), 7.32(m, 3H), 5.01(2s, 2H) | 599 | | (M − H)− |
| 108. | 3 | (DMSO) d 11.67–11.44(2s, 1H), 8.22–7.99(2s, 1H), 7.47(m, 13H), 3.91–3.54(2s, 2H). | 393 | | (M − H)− |
| 109. | 3 | (DMSO) d 11.71–11.45(2s, 1H), 8.13(m, 2H), 7.88(m, 2H), 7.35(m, 9H), 3.94–3.54(2s, 2H). | 399 | | (M − H)− |
| 110. | 3 | (DMSO) d 11.79–11.54(2s, 1H), 8.37–8.13(2s, 1H), 7.93(m, 1H), 7.73(m, 2H), 7.33(m, 9H), 6.78(m, 1H), 3.95–3.55(2s, 2H), 2.65(s, 3H). | 407 | | (M − H)− |
| 111. | 3 | (DMSO) d 11.69–11.40(2s, 1H), 8.25–7.99(2s, 1H), 7.84(m, 1H), 7.72(s, 1H), 7.32(m, 11H), 3.90–3.54(2s, 2H), 2.35(s, 3H). | 407 | | (M − H)− |
| 112. | 3 | (DMSO) d 11.80–11.54(2s, 1H), 8.34–8.11(2s, 1H), 7.88(m, 3H), 7.40(m, 9H), 7.03(m, 1H), 3.94–3.55(2s, 2H). | 411 | | (M − H)− |
| 113. | 3 | (DMSO) d 11.70–11.47(2s, 1H), 8.25–8.00(2s, 1H), 7.88(m, 1H), 7.40(m, 12H), 3.92–3.54(2s, 2H). | 411 | | (M − H)− |
| 114. | 3 | (DMSO) d 11.68–11.46(2s, 1H), 8.07(m, 6H), 7.31(m, 8H), 3.92–3.56(2s, 2H). | 418 | | (M − H)− |
| 115. | 3 | (DMSO) d 11.67–11.45(2s, 1H), 8.01(m, 6H), 7.29(m, 8H), 3.93–3.56(2s, 2H). | 418 | | (M − H)− |
| 116. | 3 | (DMSO) d 11.70–11.45(2s, 1H), 8.26–8.02(2s, 1H), 7.83(m, 4H), 7.38(m, 9H), 3.92–3.54(2s, 2H). | 427 | | (M − H)− |
| 117. | 3 | (DMSO) d 11.70–11.45(2s, 1H), 8.26–8.02(2s, 1H), 7.83(m, 4H), 7.38(m, 9H), 3.92–3.54(2s, 2H). | 427 | | (M − H)− |
| 118. | 3 | (DMSO) d 11.71–11.48(2s, 1H), 8.12(m, 2H), 7.88(m, 1H), 7.72(m, 2H), 7.32(m, 8H), 3.93–3.54(2s, 2H). | 429 | | (M − H)− |
| 119. | 3 | (DMSO) d 11.63–11.35(2s, 1H), 8.58(m, 1H), 7.68(m, 16H), 3.74–3.49(2s, 2H). | 443 | | (M − H)− |
| 120. | 3 | (DMSO) d 11.69–11.44(2s, 1H), 8.13(m, 2H), 7.84(m, 2H), 7.66(m, 1H), 7.34(m, 8H), 3.92–3.54(2s, 2H). | 445 | | (M − H)− |
| 121. | 3 | (DMSO) d 11.64–11.37(2s, 1H), 7.99(m, 2H), 7.69(m, 4H), 7.30(m, 8H), 3.86–3.53(2s, 2H), 1.26–1.23(2s, 9H). | 449 | | (M − H)− |

TABLE II-continued

| Compound | Method | ¹H NMR | LRMS | HRMS | Ion |
|---|---|---|---|---|---|
| 122. | 3 | (DMSO) d 11.67–11.37(2s, 1H), 8.11(m, 4H), 7.86(m, 2H), 7.33(m, 8H), 3.89–3.52(2s, 2H). | 461 | | (M − H)⁻ |
| 123. | 3 | (DMSO) d 11.65–11.40(2s, 1H), 8.01(m, 6H), 7.32(m, 8H), 3.88–3.53(2s, 2H). | 461 | | (M − H)⁻ |
| 124. | 3 | (DMSO) d 11.85–11.59(2s, 1H), 8.42–8.19(2s, 1H), 8.10(m, 1H), 7.97(m, 2H), 7.70(m, 1H), 7.34(m, 7H), 6.96(m, 1H), 3.97–3.56(2s, 2H). | 461 | | (M − H)⁻ |
| 125. | 3 | (DMSO) d 11.68–11.42(2s, 1H), 8.11(m, 2H), 7.88(m, 2H), 7.73(m, 1H), 7.36(m, 8H), 3.92–3.55(2s, 2H). | 461 | | (M − H)⁻ |
| 126. | 3 | (DMSO) d 11.73–11.45(2s, 1H), 8.17(m, 2H), 7.88(m, 3H), 7.38(m, 8H), 3.93–3.55(2s, 2H). | 461 | | (M − H)⁻ |
| 127. | 3 | (DMSO) d 11.70–11.43(2s, 1H), 8.01(m, 5H), 7.37(m, 9H), 3.92–3.55(2s, 2H). | 471 | | (M − H)⁻ |
| 128. | 3 | (DMSO) d 11.66–11.42(2s, 1H), 8.19–7.93(2s, 1H), 7.82(m, 5H), 7.29(m, 8H), 3.93–3.55(2s, 2H). | 471 | | (M − H)⁻ |
| 129. | 3 | (DMSO) d 11.67–11.44(2s, 1H), 8.01(m, 4H), 7.32(m, 10H), 3.92–3.55(2s, 2H). | 411 | | (M − H)⁻ |
| 130. | 3 | (DMSO) d 11.79–11.50(2s, 1H), 8.38–8.12(2s, 1H), 7.93(m, 1H), 7.63(m, 1H), 7.36(m, 9H), 6.82(m, 1H), 3.93–3.55(2s, 2H), 2.56–2.52(2s, 3H), 2.31(s, 3H). | 421 | | (M − H)⁻ |
| 131. | 3 | (DMSO) d 11.66–11.40(2s, 1H), 8.21–7.95(2s, 1H), 7.81(m, 3H), 7.26(m, 10H), 3.90–3.81(2s, 3H), 3.77–3.54(2s, 2H). | 423 | | (M − H)⁻ |
| 132. | 3 | (DMSO) d 11.85–11.59(2s, 1H), 8.45–8.24(2s, 1H), 7.79(m, 5H), 7.32(m, 7H), 6.89(m, 1H), 3.97–3.56(2s, 2H). | 427 | | (M − H)⁻ |
| 133. | 3 | (DMSO) d 11.80–11.54(2s, 1H), 8.33–8.08(2s, 1H), 7.92(m, 2H), 7.69(m, 1H), 7.34(m, 8H), 7.07(m, 1H), 3.95–3.55(2s, 2H). | 429 | | (M − H)⁻ |
| 134. | 3 | (DMSO) d 11.61–11.38(2s, 1H), 7.92(m, 4H), 7.28(m, 10H), 3.89–3.53(2s, 2H), 2.56(m, 2H), 1.53(m, 2H), 0.83(m, 3H). | 435 | | (M − H)⁻ |
| 135. | 3 | (DMSO) d 11.61–11.38(2s, 1H), 7.93(m, 4H), 7.31(m, 10H), 3.89–3.52(2s, 2H), 2.92(m, 1H), 1.18–1.12(2d, 6H). | 435 | | (M − H)⁻ |
| 136. | 3 | (DMSO) d 11.74–11.44(2s, 1H), 8.64(m, 1H), 8.30(m, 4H), 7.79(m, 4H), 7.30(m, 7H), 6.63(m, 1H), 3.91–3.55(2s, 2H). | 443 | | (M − H)⁻ |
| 137. | 3 | (DMSO) d 11.85–11.60(2s, 1H), 8.44–8.21(2s, 1H), 7.99(m, 3H), 7.37(m, 8H), 6.93(m, 1H), 3.97–3.56(2s, 2H). | 445 | | (M − H)⁻ |
| 138. | 3 | (DMSO) d 11.81–11.52(2s, 1H), 8.42–8.17(2s, 1H), 7.93(m, 1H), 7.31(m, 10H), 7.08(m, 1H), 3.76(m, 8H). | 453 | | (M − H)⁻ |
| 139. | 3 | (DMSO) d 11.84–11.60(2s, 1H), 8.44–8.22(2s, 1H), 7.95(m, 4H), 7.34(m, 7H), 7.00(m, 1H), 3.96–3.56(2s, 2H). | 461 | | (M − H)⁻ |
| 140. | 3 | (DMSO) d 11.86–11.60(2s, 1H), 8.44–8.28(2s, 1H), 8.00(m, 3H), 7.70(m, 2H), 7.33(m, 7H), 6.85(m, 1H), 3.98–3.56(2s, 2H). | 471 | | (M − H)⁻ |
| 141. | 3 | (DMSO) d 11.81–11.54(2s, 1H), 8.37–8.13(2s, 1H), 7.95(m, 3H), 7.68(m, 2H), 7.33(m, 7H), 6.85(m, 1H), 3.98–3.56(2s, 2H). | 477 | | (M − H)⁻ |
| 142. | 3 | (DMSO) d 11.65–11.42(2s, 1H), 8.02(m, 4H), 7.60(m, 2H), 7.30(m, 8H), 3.90–3.53(2s, 2H). | 477 | | (M − H)⁻ |
| 143. | 3 | (DMSO) d 11.68–11.41(2s, 1H), 8.26–8.01(2s, 1H), 7.87(m, 1H), 7.32(m, 12H), 3.73(m, 8H). | 423 | | (M − H)⁻ |
| 144. | 3 | (DMSO) d 11.67–11.43(2s, 1H), 8.25–7.98(2s, 1H), 7.81(m, 7H), 7.34(m, 11H), 3.81–3.49(2s, 2H). | 469 | | (M − H)⁻ |
| 145. | 3 | (DMSO) d 11.60–11.39(2s, 1H), 7.98(m, 2H), 7.70(m, 2H), 7.42(m, 4H), 7.22(m, 2H), 6.86(m, 3H), 3.70(m, 5H), 2.34–2.29(2s, 3H). | 437 | | (M − H)⁻ |

TABLE II-continued

| Compound | Method | ¹H NMR | LRMS | HRMS | Ion |
|---|---|---|---|---|---|
| 146. | 3 | (DMSO) d 11.62–11.40(2s, 1H), 8.01(m, 6H), 7.45(m, 2H), 7.19(m, 2H), 6.84(m, 3H), 3.68(m, 5H). | 491 | | (M − H)⁻ |
| 147. | 3 | (DMSO) d 11.64–11.46(2s, 1H), 7.98(m, 2H), 7.71(m, 2H), 7.28(m, 8H), 7.12(m, 1H), 3.95–3.58(2s, 2H), 2.35–2.30(2s, 3H). | 441 | | (M − H)⁻ |
| 148. | 3 | (DMSO) d 11.66–11.46(2s, 1H), 8.00(m, 6H), 7.32(m, 7H), 3.92–3.56(2s, 2H). | 495 | | (M − H)⁻ |
| 149. | 3 | (DMSO) d 11.56–11.34(2s, 1H), 7.98(m, 2H), 7.74(m, 2H), 7.42(m, 4H), 7.09(m, 1H), 6.83(m, 3H), 3.64(m, 8H), 3.32–3.29(2s, 3H). | 467 | | (M − H)⁻ |
| 150. | 3 | (DMSO) d 11.58–11.35(2s, 1H), 8.00(m, 6H), 7.45(m, 2H), 7.15(m, 1H), 6.84(m, 3H), 3.63(m, 8H). | 521 | | (M − H)⁻ |
| 151. | 3 | (DMSO) d 11.65–11.40(2s, 1H), 8.22–7.95(2s, 1H), 7.81(m, 3H), 7.23(m, 6H), 6.84(m, 3H), 3.69(m, 8H). | 453 | | (M − H)⁻ |
| 152. | 3 | (DMSO) d 11.62–11.35(2s, 1H), 8.25–7.97(2s, 1H), 7.84(m, 1H), 7.27(m, 7H), 6.85(m, 3H), 3.68(m, 11H). | 483 | | (M − H)⁻ |
| 153. | 3 | (DMSO) d 11.79–11.51(2s, 1H), 8.41–8.17(2s, 1H), 7.93(m, 1H), 7.31(m, 6H), 7.07(m, 1H), 6.85(m, 3H), 3.73(m, 11H) | 483 | | (M − H)⁻ |
| 154. | 3 | (DMSO) d 11.80–11.50(2s, 1H), 8.42–8.17(2s, 1H), 7.93(m, 1H), 7.64–7.61(2s, 1H), 7.02(m, 9H), 3.73(m, 11H). | 483 | | (M − H)⁻ |
| 155. | 3 | | 473 | | (M + H)+ |
| 156. | 3 | | 469 | | (M + H)+ |
| 157. | 3 | | 453 | | (M + H)+ |
| 158. | 3 | | 457 | | (M + H)+ |
| 159. | 3 | | 457 | | (M + H)+ |
| 160. | 3 | | 469 | | (M + H)+ |
| 161. | 3 | | 483 | | (M + H)+ |
| 162. | 3 | | 489 | | (M + H)+ |
| 163. | 3 | | 453 | | (M + H)+ |
| 164. | 3 | | 461 | | (M + H)+ |
| 165. | 3 | | 523 | | (M + H)+ |
| 166. | 3 | | 572 | | (M + H)+ |
| 167. | 3 | | 527 | | (M + H)+ |
| 168. | 3 | | 507 | | (M + H)+ |
| 169. | 3 | | 602 | | (M + H)+ |
| 170. | 3 | | 523 | | (M + H)+ |
| 171. | 3 | | 507 | | (M + H)+ |
| 172. | 3 | | 511 | | (M + H)+ |
| 173. | 3 | | 511 | | (M + H)+ |
| 174. | 3 | | 527 | | (M + H)+ |
| 175. | 3 | | 511 | | (M + H)+ |
| 176. | 3 | | 515 | | (M + H)+ |
| 177. | 3 | | 453 | | (M + H)+ |
| 178. | 3 | | 507 | | (M + H)+ |
| 179. | 3 | | 511 | | (M + H)+ |
| 180. | 3 | | 473 | | (M + H)+ |
| 181. | 3 | (MeOD-d6) 8.57(d, 1H), 8.42(d, 1H), 8.26(m, 2H), 7.85(d, 2H), 7.41(m, 3H), 7.26(m, 1H), 6.88(m, 3H), 4.03(s, 1H), 3.82(s, 2H), 3.76(s, 1H), 3.62(s, 1H), 2.42(d, 3H) | 440 | | (M + H)+ |
| 182. | 3 | (DMSO) d 11.48–11.25(2s, 1H), 8.52(m, 2H), 8.13(m, 2H), 7.84(m, 1H), 7.32(m, 4H), 6.84(m, 3H), 3.62(m, 5H). | 481 | | (M − H)⁻ |
| 183. | 3 | (DMSO) d 11.59–11.38(2s, 1H), 7.92(m, 4H), 7.29(m, 6H), 6.86(m, 3H), 3.68(m, 5H), 2.56(m, 2H), 1.52(m, 2H), 1.23(m, 4H), 0.84(m, 3H). | 493 | | (M − H)⁻ |
| 184. | 3 | (DMSO) d 11.59–11.37(2s, 1H), 7.91(m, 4H), 7.29(m, 6H), 6.86(m, 3H), 3.68(m, 5H), 2.57(m, 2H), 1.52(m, 2H), 0.82(m, 3H). | 465 | | (M − H)⁻ |
| 185. | 3 | (MeOD-d6) 8.60(m, 1H), 7.78(m, 1H), 7.63(m, 2H), 7.53(m, 1H), 7..32(d, 2H), 7.22(m, 2H), 6.93(m, 2H), 6.81(m, 2H), 4.04(S, 1H), 3.87(S, 1H), 3.73(s, 2H), 3.59(s, 1H), 2.27(S, 3H) | 440 | | (M + H)+ |

TABLE II-continued

| Compound | Method | ¹H NMR | LRMS | HRMS | Ion |
|---|---|---|---|---|---|
| 186. | 3 | (DMSO) d 11.63–11.40(2s, 1H), 8.20–7.94(2s, 1H), 7.86(m, 1H), 7.70(m, 2H), 7.42(m, 2H), 7.16(m, 4H), 6.85(m, 3H), 4.67(m, 1H), 3.69(m, 5H), 1.24(m, 6H). | 481 | | (M − H)⁻ |
| 187. | 3 | (DMSO) d 11.74–11.49(2s, 1H), 8.30–8.04(2s, 1H), 7.94(m, 1H), 7.48(m, 3H), 7.23(m, 2H), 6.85(m, 3H), 3.72(m, 5H). | 497 | | (M − H)⁻ |
| 188. | 3 | (DMSO) d 11.71–11.50(2s, 1H), 7.73(m, 12H), 6.82(m, 3H), 3.69(m, 5H), 2.14–2.08(2s, 3H). | 503 | | (M − H)⁻ |
| 189. | 3 | (DMSO) d 11.82–11.52(2s, 1H), 8.38–8.27(2s, 1H), 7.94(m, 4H), 7.70(m, 1H), 7.48(m, 2H), 7.26(m, 2H), 6.84(m, 3H), 5.34–5.32(2s, 2H), 3.75(m, 5H). | 507 | | (M + H)⁺ |
| 190. | 3 | (DMSO) d 11.70–11.48(2s, 1H), 8.23–7.99(2s, 1H), 7.91(m, 1H), 7.51(m, 4H), 7.21(m, 2H), 6.85(m, 3H), 3.72(m, 5H). | 507 | | (M − H)⁻ |
| 191. | 3 | (DMSO) d 11.65–11.44(2s, 1H), 8.00(m, 4H), 7.65(m, 4H), 7.45(m, 7H), 6.83(m, 3H), 3.71(m, 5H). | 515 | | (M − H)⁻ |
| 192. | 3 | (DMSO) d 11.69–11.44(2s, 1H), 8.13(m, 2H), 7.89(m, 3H), 7.47(m, 2H), 7.23(m, 2H), 6.81(m, 3H), 3.62(m, 5H). | 564 | | (M − H)⁻ |
| 193. | 3 | | 527 | | (M + H)⁺ |
| 194. | 3 | | 531 | | (M + H)⁺ |
| 195. | 3 | (DMSO) d 11.65–11.41(2s, 1H), 8.01(m, 6H), 7.44(m, 2H), 7.17(m, 2H), 6.84(m, 3H), 3.67(m, 5H), 2.60–2.59(2S, 3H). | 465 | | (M − H)⁻ |
| 196. | 3 | (DMSO) d 11.66–11.44(2s, 1H), 8.66(m, 1H), 8.05(m, 3H), 7.89(m, 6H), 7.17(m, 2H), 6.77(m, 4H), 3.63(m, 5H). | 489 | | (M − H)⁻ |
| 197. | 3 | (DMSO) d 11.63–11.39(2s, 1H), 8.21(m, 8H), 7.44(m, 2H), 7.18(m, 2H), 6.82(m, 3H), 3.62(m, 5H). | 490 | | (M − H)⁻ |
| 198. | 3 | (DMSO) d 11.62–11.38(2s, 1H), 7.99(m, 2H), 7.74(m, 2H), 7.47(m, 2H), 7.40(m, 2H), 7.18(m, 2H), 6.85(m, 3H), 3.67(m, 5H), 1.57(m, 2H), 1.22–1.18(2s, 6H), 0.53(m, 3H). | 493 | | (M − H)⁻ |
| 199. | 3 | (DMSO) d 11.64–11.40(2s, 1H), 8.22–7.94(2s, 1H), 7.84(m, 1H), 7.72(m, 2H), 7.42(m, 2H), 7.17(m, 4H), 6.86(m, 3H), 3.98(m, 2H), 3.69(m, 5H), 1.67(m, 2H), 1.40(m, 2H), 0.92(m, 3H). | 495 | | (M − H)⁻ |
| 200. | 3 | (DMSO) d 11.68–11.44(2s, 1H), 7.99(m, 8H), 7.22(m, 2H), 6.82(m, 3H), 3.62(m, 5H). | 496 | | (M − H)⁻ |
| 201. | 3 | (DMSO) d 11.68–11.50(2s, 1H), 8.57(m, 1H), 8.04(m, 3H), 7.46(m, 4H), 7.23(m, 6H), 6.84(m, 3H), 3.72(m, 5H). | 516 | | (M − H)⁻ |
| 202. | 3 | (DMSO) d 11.64–11.44(2s, 1H), 7.98(m, 4H), 7.44(m, 2H), 7.19(m, 8H), 6.83(m, 3H), 3.71(m, 5H). | 533 | | (M − H)⁻ |
| 203. | 3 | (MeOD-d6) 8.24(s, 1H), 8(m, 2H), 7.93(d, 1H), 7.81(s, 1H), 7.32(m, 3H), 7.12(m, 1H), 6.99(m, 1H), 6.86(m, 2H), 3.89(S, 1H), 3.83(S, 1H), 3.76(s, 2H), 3.59(s, 1H), 2.49(S, 1H), 2.46(S, 2H) | 507 | | (M + H)+ |
| 204. | 3 | (CDCl3) 8.56(s, 1H), 7.90(d, 1H), 7.72(d, 3H), 7.56(d, 1H), 7.38–6.80(m, 6H), 4.00(s, 1H), 3.56(s, 1H), 2.45(t, 3H) | 453 | | (M + H)+ |
| 205. | 3 | | 461 | | (M + H)+ |
| 206. | 3 | | 515 | | (M + H)+ |
| 207. | 3 | | 511 | | (M + H)+ |
| 208. | 3 | | 457 | | (M + H)+ |
| 209. | 3 | | 473 | | (M + H)+ |
| 210. | 3 | | 527 | | (M + H)+ |
| 211. | 3 | | 513 | | (M + H)+ |
| 212. | 3 | | 461 | | (M + H)+ |
| 213. | 3 | | 498 | | (M + H)+ |
| 214. | 3 | | 494 | | (M + H)+ |
| 215. | 3 | | 499 | | (M + H)+ |
| 216. | 3 | (DMSO) d 11.68–11.41(2s, 1H), 8.37(m, 1H), 8.28–8.00(2s, 1H), 8.88(m, 1H), 7.76(m, 1H), 7.44(m, 2H), 7.23(m, 2H), 6.86(m, 4H), 3.71(m, 13H). | 509 | | (M − H)⁻ |

TABLE II-continued

| Compound | Method | ¹H NMR | LRMS | HRMS | Ion |
|---|---|---|---|---|---|
| 217. | 3 | (DMSO) d 11.64–11.44(2s, 1H), 8.49(m, 2H), 7.99(m, 4H), 7.49(m, 4H), 7.18(m, 4H), 6.83(m, 3H), 3.72(m, 5H). | 516 | | (M − H)⁻ |
| 218. | 3 | (DMSO) d 11.67–11.49(2s, 1H), 8.64(m, 1H), 8.49(m, 1H), 8.29–8.04(2s, 1H), 7.92(m, 3H), 7.48(m, 4H), 7.16(m, 2H), 6.81(m, 3H), 3.70(m, 5H). | 620 | | (M + H)⁺ |
| 219. | 3 | 10.41(s, 1H), 8.00(m, 4H), 7.32(m, 9H), 3.81(s, 2H), 1.99(s, 3H). | 477 | | (M + H)⁺ |
| 220. | 3 | 10.39(s, 1H), 7.99(m, 4H), 7.51(m, 2H), 7.25(m, 2H), 6.83(m, 3H), 3.75(s, 2H), 3.70(s, 3H), 1.94(s, 3H). | 525 | | (M + H)⁺ |
| 221. | 3 | 1.40(s, 1H), 7.99(m, 4H), 7.47(m, 5H), 6.83(m, 3H), 3.72(s, 2H), 3.69(s, 3H), 1.98(s, 3H). | 507 | | (M + H)⁺ |
| 222. | 3 | 10.46(s, 1H), 8.00(m, 4H), 7.35(m, 5H), 6.87(m, 2H), 3.75(s, 2H), 3.70(s, 3H), 1.96(s, 3H). | 525 | | (M + H)⁺ |
| 223. | 3 | 10.53(s, 1H), 8.02(m, 4H), 7.46(m, 5H), 7.25(m, 2H), 3.86(s, 2H), 2.00(s, 3H). | 545 | | M+ |
| 224. | 3 | (DMSO) d 11.62–11.41(2s, 1H), 7.95(m, 4H), 7.43(m, 4H), 7.17(m, 2H), 6.85(m, 3H), 3.70(m, 8H), 2.75(m, 4H). | 509 | | (M − H)⁻ |
| 225. | 3 | (DMSO) d 11.65–11.41(2s, 1H), 8.22–7.97(2s, 1H), 7.82(m, 4H), 7.41(m, 2H), 7.16(m, 4H), 6.86(m, 3H), 5.40–5.29(2s, 2H), 3.70(m, 5H). | 570 | | (M − H)⁻ |
| 226. | 3 | (DMSO) d 11.66–11.46(2s, 1H), 8.03(m, 3H), 7.52(m, 3H), 7.22(m, 3H), 6.80(m, 3H), 3.97(s, 3H), 3.63(m, 5H). | 577 | | (M − H)⁻ |
| 227. | 3 | (MeOD-d6) 8.83(dd, 1H), 8.73(m, 1H), 8.48–8.20(m, 6H), 7.30(m, 4H), 4.05(S, 1H), 3.69(S, 1H) | 498 | | (M + H)+ |
| 228. | 3 | (MeOD-d6) 8.51(dd, 1H), 8.34(d, 1H), 7.80(dd, 1H), 7.69(m, 2H), 7.30(m, 5H), 4.03(S, 1H), 3.66(S, 1H), 2.33(S, 3H) | 444 | | (M + H)+ |
| 229. | 3 | | 440 | | (M + H)+ |
| 230. | 3 | | 494 | | (M + H)+ |
| 231. | 4 | (DMSO) d 11.53–11.32(2s, 1H), 8.22–8.14(2s, 1H), 7.80(m, 1H), 7.57(m, 2H), 7.30(m, 9H), 4.94–4.80(2s, 2H), 3.98–3.60(2s, 2H), 2.36–2.32(2s, 3H). | 439 | | (M − H)⁻ |
| 232. | 4 | (DMSO) d 11.50–11.25(2s, 1H), 8.22–8.13(2s, 1H), 7.79(m, 1H), 7.56(m, 2H), 7.31(m, 10H), 4.93–4.80(2s, 2H), 3.95–3.57(2s, 2H), 2.36–2.31(2s, 3H). | 405 | | (M − H)⁻ |
| 233. | 4 | (DMSO) d 11.48–11.25(2s, 1H), 8.21–8.12(2s, 1H), 7.70(m, 1H), 7.55(m, 2H), 7.31(m, 6H), 6.87(m, 3H), 4.94–4.79(2s, 2H), 3.72(m, 5H), 2.35–2.31(2s, 3H). | 435 | | (M − H)⁻ |
| 234. | 5a | (DMSO) 11.70–11.55(m, 1H), 8.51–8.33(m, 1H), 8.00–7.92(m, 1H), 7.42–7.19(m, 9H), 6.91–6.85(m, 3H), 3.98–3.43(m, 2H), 2.29(s, 3H) | 345.3 | | (M + H)+ |
| 235. | 5b | (DMSO-d₆) d 11.65, 11.39(s, 1H), 8.54, 8.43(s, 1H), 7.89–7.87(m, 1H), 7.40–7.17(m, 12H), 7.05–6.98(m, 1H), 5.15.14–5.11(m, 2H), 3.97, 3.51(s, 2H), 2.33–2.31(m, 3H). | | 359.1766 | (M + H)+ |
| 236. | 5b | (DMSO-d₆) d 11.62, 11.38(s, 1H), 8.53, 8.42(s, 1H), 7.90–7.80(m, 1H), 7.40–7.36(m, 3H), 7.22–7.17(m, 4H); 7.04–6.98(m, 1H), 6.88–6.78(m, 3H), 5.15–5.12(m, 2H), 3.94, 3.47(s, 2H), 3.74, 3.70(s, 3H), 2.33–2.31(m, 3H). | 389.2 | | (M + H)+ |
| 237. | 5b | (DMSO-d₆) 11.80–11.65(m, 1H), 8.54–8.43(m, 3H), 7.90–7.66(m, 2H), 7.44–7.23(m, 6H), 7.21–7.19(m, 1H), 7.05–6.89(m, 1H), 5.14–5.13(m, 2H), 4.02(s, 1H), 3.34(s, 1H), 1.30–1.28(m, 9H) | 402.2 | | (M + H)+ |
| 238. | 5b | (DMSO-d₆) 11.60–11.55(m, 1H), 8.43–8.38(m, 1H), 8.11–7.74(m, 4H), 7.60–7.56(m, 2H), 7.44–7.42(m, 2H), 7.31–7.21(m, 4H), 7.05–7.04(m, 1H), 5.65–5.63(m, 2H), 3.96(s, 1H), 3.54(s, 1H), 3.34(s, 3H) | 395.2 | | (M + H)+ |

TABLE II-continued

| Compound | Method | ¹H NMR | LRMS | HRMS | Ion |
|---|---|---|---|---|---|
| 239. | 5c | (DMSO-d$_6$) 12.00–11.85(m, 1H), 8.95–8.80(m, 1H), 8.16–8.10(m, 1H), 7.99–7.81(2H), 7.72–7.65(m, 2H), 7.42–7.37(m, 2H), 7.27–7.16(m, 1H), 6.93–6.76(m, 4H), 3.92–3.36(m, 5H), 2.35(s, 3H) | 423 | | (M + H)+ |
| 240. | 6a | (DMSO-d$_6$) 12.23(s, 1H), 8.11–8.08(m, 0.5H), 8.04–8.01(m, 2H), 7.85–7.80(m, 2H), 7.75(m, 0.5H), 7.62–7.56(m, 2H), 7.54–7.53(m, 1H), 7.51–7.46(m, 1H), 7.44–7.37(m, 1H), 7.34–7.27(m, 1H), 6.75–6.68(m, 1H), 3.20–3.18(m, 3H) | | 530.0335 | M+ |
| 241. | 6a | (CDCl$_3$)(mixture of geometric isomers) d 3.73&4.17(2s, 2H); 7.1–7.7(m); 7.67&7.75(2m, 2H); 7.88(s) 7.96&8.06(2m, 2H); 9.5(bs); 10.80(bs). | 538.0/ 540.0 | | (M − H)− |
| 242. | 6a | (CDCl$_3$)(mixture of geometric isomers) d 3.73&4.17(2s, 2H); 7.16(m); 7.36(m); 7.47(s); 7.60m; 7.66(m); 7.75(m); 7.89(s); 7.96(m); 8.06(m); 9.62(bs); 10.80(bs). | 494.02 | | (M − H)− |
| 243. | 6b | (CDCl$_3$)(mixture of geometric isomers) d 3.21&3.24(2s, 3H); 4.16(bd, 2H); 6.49&6.58(2d, 1H); 7.38(m, 6H); 7.82(m, 4H); 8.17&8.29(2d, 1H); 8.27&8.48(2s, 1H); 8.93&8.98(2bs, 1H). | 474.09 | | (M − H)− |
| 244. | 6b | (CD$_3$OD)(mixture of geometric isomers) d 3.27&3.28(2s, 3H); 3.66&4.11(s&b, 2H); 6.64&6.70(2d, 1H); 7.35(m, 6H); 7.84(m, 2H); 7.93(m, 2H); 8.12&8.27(2m, 1H); 8.39&8.66(2s, 1H). | 508.08 | | (M − H)− |
| 245. | 6b | (CD$_3$OD)(mixture of geometric isomers) d 3.15&3.16(2s, 3H); 3.54&3.98(s&b, 2H); 6.52&6.59(2d, 1H); 7.21(m, 5H); 7.47(m, 1H); 7.73(m, 2H); 7.81(m, 2H); 8.00&8.15(2m, 1H); 8.26&8.54(2s, 1H). | 552.05/ 554 | | (M − H)− |
| 246. | 6b | (CDCl$_3$)(mixture of geometric isomers) d 3.25(s); 3.90(2s); 4.10(m); 6.58(m); 6.87(m); 6.96(m); 7.45(m); 7.82(m); 8.20(m); 8.29(m); 8.90&8.96(2bs). | 534.2 | | (M − H)− |
| 247. | 6b | (CDCl$_3$) d 3.25(s, 3H); 4.17(m, 2H); 6.55(d, 1H); 7.33(m); 7.47(m, 1H); 7.83(m, 6H); 8.17(m, 1H); 8.34(s, 1H); 8.56(b); 8.67(b); 9.18(s, 1H). | 475.13 | | (M − H)− |
| 248. | 6b | (CDCl$_3$)(mixture of geometric isomers) d 3.20&3.23(2s, 3H); 3.63&4.05(s + m, 2H); 5.95&6.01(2s, 2H); 6.46&6.57(2d, 1H) 6.84(m, 3H); 7.30(m); 7.44(m); 7.80(m, 4H); 8.15&8.28(2m, 1H); 8.25&8.50(2s, 1H). | 517.98 | | (M − H)− |
| 249. | 6c | (CDCl$_3$)(mixture of geometric isomers) d 3.16&3.18(2s, 3H); 3.77(b, 1H); 4.18(b, 1H); 6.49(m, 1H); 7.18(m); 7.30(m); 7.77(m, 4H); 8.05(m, 2H); 8.50&8.63(2b, 1H). | 463.96 | | (M − H)− |
| 250. | 7 | (DMSO-d$_6$) 11.56(s, 1H), 8.14–8.12(m, 2H), 8.09–8.06(m, 2H), 7.96(s, 1H), 7.91–7.89(m, 1H), 7.52–7.48(m, 1H), 7.46–7.37(m, 4H), 7.28–7.25(m, 1H), 7.13–7.11(m 1H), 4.63(s, 2H) | | 533.0229 | (M + H)+ |
| 251. | 7 | (DMSO-d$_6$) 11.51(s, 1H), 8.14–8.12(m, 2H), 8.09–8.07(m, 2H), 7.97(s, 1H), 7.93–7.90(m, 1H), 7.52–7.43(m, 2H), 7.38–7.30(m, 5H), 7.13–7.10(m, 1H), 4.55(s, 2H) | | 499.0609 | (M + H)+ |
| 252. | 7 | (DMSO-d$_6$) 11.55(s, 1H), 8.12–8.10(m, 2H), 8.08–8.06(m, 2H), 7.95(s, 1H), 7.86–7.83(m, 1H), 7.74–7.72(m, 2H), 7.55–7.53(m, 2H), 7.52–7.47(m, 1H), 7.44–7.40(m, 1H), 7.13–7.10(m, 1H), 4.72(s, 2H) | | 567.0488 | (M + H)+ |
| 253. | 8 | (CDCl$_3$) d 1.15(m, 1H); 1.25(m, 1H); 2.07(m, 1H); 2.80(m, 1H); 3.50(s, 2H); 5.97(m, 3H); 6.78(m, 4H); 7.05(m, 1H); 7.13(m, 1H); 7.21(m, 1H); 7.85(m, 2H); 8.02(m, 2H). | 519.9 | | (M + H)+ |

TABLE II-continued

| Compound | Method | ¹H NMR | LRMS | HRMS | Ion |
|---|---|---|---|---|---|
| 254. | 9 | (MeOD-d6) 8.54(d, 1H), 8.01(d, 2H), 7.82(m, 4H), 7.42(d, 1H), 7.34(t, 1H), 7.26(m, 4H), 7.05(t, 1H), 4.41(s, 2H) | 452 | | (M + H)+ |
| 255. | 10 | (DMSO-$d_6$) 11.76(s, 1H), 8.10–8.08(m, 2H), 8.05–8.03(m, 2H), 7.90(S, 1H), 7.87–7.85(m, 2H), 7.72–7.59(m, 4H), 7.47–7.43(m, 1H), 7.40–7.36(m, 1H), 7.10–7.07(m, 1H) | | 485.0467 | (M + H)+ |
| 256. | 10 | (DMSO-$d_6$) 12.15(s, 1H), 8.78–8.76(m, 1H), 8.29–8.25(m, 2H), 8.11–8.09(m, 1H), 8.06–8.04(m, 2H), 7.99–7.97(m, 2H), 7.93(s, 1H), 7.81–7.77(m, 1H), 7.72–7.66(m, 2H), 7.59–7.57(m, 1H), 7.42–7.38(m, 1H), 7.35–7.31(m, 1H), 7.04–7.01(m, 1H) | 534.9 | | (M + H) |

Example 11

Evaluation of Polymerase Activity

Compounds of the present invention can be evaluated for inhibition of HCV NS5b RNA dependent RNA polymerase activity in assays comprised of a suitable buffer (e.g. 20 mM Tris-HCl pH 7.6), primed or unprimed RNA templates, GTP, ATP, CTP, and UTP, $MnCl_2$ or $MgCl_2$, and reducing agent such as 10 mM dithiothreitol or 2-mercaptoethanol. The assay buffer may contain salts such as ammonium acetate, KCl, or NaCl, and nonionic or zwitterionic detergents such as Tween or CHAPS. The incorporation of nucleotides into the complementary RNA strand may be monitored by the incorporation of radiolabeled NTP (e.g. $^3$H labeled GTP). Suitable RNA templates for de novo initiation in the presence of 20–50 μM GTP or ATP are the homopolymers poly rC and poly rU, respectively. Heteropolymer RNA templates with 1–3 cytidine (C) bases or 1–3 uridine (U) bases at the 3' terminus of the template may also be used for de novo initiation. Primed RNA templates such as poly rC primed with oligo rG or oligo dG, and poly rA primed with oligo rU may also be used to detect polymerase activity. The primers may be any length greater than 10 bases. A biotin residue may be added to the 5' end of the template or the 5' end of the primer to capture the template and the newly synthesized, complementary strand on avidin coated spheres. One embodiment of this technology consists of a mixture of NS5b polymerase, a poly rC RNA template primed with 5' biotinylated oligo rG, 20 mM Tris HCl pH 7.6, 100 mM ammonium acetate, 10 mM dithiothreitol, 2 mM CHAPS, 1 mM $MgCl_2$, and 150–200 nM $^3$H labeled GTP. Test compounds (inhibitors) may be incorporated in the reaction mixture with up to 10% DMSO. The reaction is run for various times (1–180 minutes) at 22–37° C., and stopped by the addition of 10–140 mM EDTA. Scintillation Proximity Assay avidin-coated beads (Amersham Pharmacia Biotech) are added to capture the ds RNA product; or the reaction mixtures may be transferred to avidin coated Flash Plates (Perkin Elmer Life Sciences). The incorporation of radiolabeled GTP into the complementary strand is measured in 96, 384, or 1536 well plates in scintillation counters such as the Wallac Microbeta and Packard TopCount.

Compounds were evaluated for inhibition of viral replication according to published procedures (Bartenschlager, R., et. al., Science, 1999, 285, 110) with modifications as follows.

HuH-7 replicon cells 5–15 and 9–13 were cultured in Dulbecco's minimal essential medium (DMEM) containing high glucose and supplemented with 10% fetal bovine serum (FBS), L-glutamine (2 mM), non-essential amino acids (1×), Penicillin (100 IU/mL)/Streptomycin (100 μg/mL) and G418 (Geneticin, 750 μg/mL). Unless otherwise specified, all media components were obtained from Invitrogen. Replicon cell line stocks were maintained as sub-confluent monolayers by passaging every Monday (1:6 split) and Thursday (1:10 split) and incubated at 37° C. with 5% $CO_2$. Tissue culture plates (96-well white clear bottom plates, Corning #3610) were seeded at 7×10$^3$ cells/well and incubated for 24 hours prior to addition of the compounds.

Compounds in dry powder form were diluted in DMSO (30 mM stock). Serial dilutions of each Compound in DMSO (10 mM–0.1 mM) were performed in a 96-well polypropylene plate using a microtiter format. Culture media (200 μl) was added to the corresponding wells of a sterile 96-well round bottom plate. Diluted compound (2 μl) was added to the corresponding wells of the medial plate (final compound concentrations: 100 μM–1 μM). Culture media was removed from the corresponding wells of the 96-well plate containing the replicon cells and 150 μl diluted compound added. Media containing 1% DMSO and a serially diluted IFN were included on each plate. The cultures were incubated at 37° C. with 5% $CO_2$ for 3 days. Cultures were observed visually for cytotoxicity or compound precipitation prior to RNA extraction described below.

Total cellular RNA was extracted by spin column technology (RNeasy 96, Qiagen) using the vacuum methodology according to the manufacturer's protocol. In brief, culture media was removed and 100 μl RLT lysis buffer containing 0.14M β-mercaptoethanol (β-ME) was added to each well. The plate was kept flat on the laboratory bench and shaken vigorously to lyse the cells. An equal volume of 70% ETOH was mixed with the lysate and added to the corresponding columns of the RNeasy 96-well plate. Vacuum was applied to draw the lysate through the filters. After ventilating the plate, buffer RW1 (1 mL) was drawn through each column. The waste tray was emptied and the filters washed twice with buffer RPE (1 mL/wash). After ventilating the tray, the RNeasy plate was removed and the bottom of the plate struck several times on a stack of paper towels to remove excess wash buffer. The waste tray was removed from the vacuum apparatus and the RNeasy 96-well plate dried by applying vacuum for 10 minutes. Total cellular RNA was eluted from the columns with two washes of 60 μl RNase-free water.

Relative quantitative multiplex RT-PCR was performed using TaqMan (TM) EZ RT Core Reagent kit (Perkin Elmer) according to the manufacturer's protocol (PE Applied Biosystems User Bulletin #2). Primer 061 (NT 61–82) and 139 (NT 139–158) amplifying a short region in the 5' untranslated region of the HCV genome were utilized at 300 nM final concentrations. Probe #3 (NT 97–119) labeled with FAM reporter dye was utilized at 200 nM final concentration. Pre-developed human GAPDH primers and probe labeled with VIC reporter dye were obtained from PE Applied Biosystems (# 4310884E) and used according to the manufacturer's protocol. TM RT-PCR master mix was prepared containing the above primers/probe for both target RNA. Total cellular RNA (2 μl) was added to the reaction tubes of a 96-well optical plate that corresponded to the wells of the replicon culture plate. The final volume of each reaction was 50 μl. A standard curve was prepared from ten-fold serial dilutions of total cellular RNA extracated from $10^6$ replicon cells and eluted in 30 μl RNase-free water. Thermocycler (7700, Perkin Elmer) conditions consisted of: 50° C. hold for 2 minutes, 70° C. hold for 10 minutes, 60° C. hold for 30 minutes, 95° C. hold for 5 minutes followed by 40 cycles at 95° C. for 20 seconds and 60° C. for 1 minute. The Thermocycler was programmed for multiplex RT-PCR and cycle threshold values for each sample converted to μg HCV and GAPDH RNA based on the standard curve using the Excel computer program. For all samples, the ratio of HCV RNA to GAPDH RNA was calculated. For samples treated with compounds, the ratio was compared to untreated cells and reported as percent control.

Table 3 lists inhibitory activity for compounds of the invention. In the Table, activity is indicated as +++ for compounds inhibiting 50% of replication at less than 5 uM; ++ for compounds showing inhibition between 5 uM and 50 uM; and + for compounds having inhibitory activity greater than 50 uM.

TABLE 3

| Compound No. | IC50 (uM) |
| --- | --- |
| 1 | ++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | + |
| 13 | +++ |
| 14 | +++ |
| 15 | +++ |
| 16 | +++ |
| 17 | +++ |
| 18 | +++ |
| 19 | ++ |
| 20 | +++ |
| 21 | +++ |
| 22 | + |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | ++ |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | ++ |
| 47 | ++ |
| 48 | +++ |
| 49 | ++ |
| 50 | +++ |
| 51 | +++ |
| 52 | +++ |
| 53 | +++ |
| 54 | +++ |
| 55 | + |
| 56 | +++ |
| 57 | +++ |
| 58 | + |
| 59 | +++ |
| 60 | +++ |
| 61 | +++ |
| 62 | +++ |
| 63 | +++ |
| 64 | +++ |
| 65 | ++ |
| 66 | ++ |
| 67 | ++ |
| 68 | +++ |
| 69 | + |
| 70 | +++ |
| 71 | +++ |
| 72 | +++ |
| 73 | +++ |
| 74 | +++ |
| 75 | +++ |
| 76 | ++ |
| 77 | +++ |
| 78 | ++ |
| 79 | ++ |
| 80 | +++ |
| 81 | + |
| 82 | ++ |
| 83 | +++ |
| 84 | +++ |
| 85 | + |
| 86 | + |
| 87 | + |
| 88 | +++ |
| 89 | ++ |
| 90 | ++ |
| 91 | + |
| 92 | ++ |
| 93 | + |
| 94 | + |
| 95 | +++ |
| 96 | + |
| 97 | + |
| 98 | ++ |
| 99 | +++ |
| 100 | +++ |
| 101 | ++ |
| 102 | +++ |
| 103 | +++ |
| 104 | +++ |
| 105 | ++ |
| 106 | +++ |
| 107 | + |
| 108 | + |
| 109 | + |

TABLE 3-continued

| Compound No. | IC50 (uM) |
|---|---|
| 110 | + |
| 111 | + |
| 112 | + |
| 113 | + |
| 114 | + |
| 115 | ++ |
| 116 | + |
| 117 | +++ |
| 118 | ++ |
| 119 | +++ |
| 120 | ++ |
| 121 | +++ |
| 122 | ++ |
| 123 | +++ |
| 124 | +++ |
| 125 | +++ |
| 126 | ++ |
| 127 | ++ |
| 128 | +++ |
| 129 | ++ |
| 130 | + |
| 131 | +++ |
| 132 | + |
| 133 | + |
| 134 | +++ |
| 135 | +++ |
| 136 | + |
| 137 | ++ |
| 138 | + |
| 139 | + |
| 140 | + |
| 141 | + |
| 142 | +++ |
| 143 | ++ |
| 144 | + |
| 145 | +++ |
| 146 | +++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |
| 156 | +++ |
| 157 | +++ |
| 158 | +++ |
| 159 | ++ |
| 160 | ++ |
| 161 | ++ |
| 162 | ++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |
| 173 | +++ |
| 174 | +++ |
| 175 | +++ |
| 176 | +++ |
| 177 | +++ |
| 178 | +++ |
| 179 | + |
| 180 | +++ |
| 181 | ++ |
| 182 | +++ |
| 183 | +++ |
| 184 | +++ |
| 185 | +++ |
| 186 | +++ |
| 187 | +++ |
| 188 | +++ |
| 189 | + |
| 190 | +++ |
| 191 | + |
| 192 | +++ |
| 193 | +++ |
| 194 | +++ |
| 195 | +++ |
| 196 | +++ |
| 197 | +++ |
| 198 | +++ |
| 199 | +++ |
| 200 | +++ |
| 201 | +++ |
| 202 | + |
| 203 | +++ |
| 204 | +++ |
| 205 | ++ |
| 206 | +++ |
| 207 | +++ |
| 208 | ++ |
| 209 | +++ |
| 210 | ++ |
| 211 | ++ |
| 212 | +++ |
| 213 | ++ |
| 214 | ++ |
| 215 | + |
| 216 | ++ |
| 217 | ++ |
| 218 | + |
| 219 | + |
| 220 | + |
| 221 | + |
| 222 | + |
| 223 | + |
| 224 | + |
| 225 | + |
| 226 | +++ |
| 227 | +++ |
| 228 | +++ |
| 229 | +++ |
| 230 | +++ |
| 231 | +++ |
| 232 | +++ |
| 233 | +++ |
| 234 | + |
| 235 | + |
| 236 | + |
| 237 | + |
| 238 | ++ |
| 239 | ++ |
| 240 | 1 |
| 241 | + |
| 242 | + |
| 243 | +++ |
| 244 | +++ |
| 245 | +++ |
| 246 | +++ |
| 247 | +++ |
| 248 | +++ |
| 249 | +++ |
| 250 | ++ |
| 251 | ++ |
| 252 | ++ |
| 253 | + |
| 254 | + |
| 255 | ++ |
| 256 | ++ |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula (Ib),

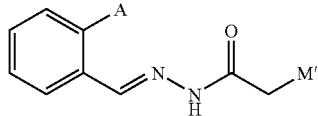

wherein:
A is selected from the group consisting of —OSO$_2$-M, —NR$_2$SO2-M, —OCR$_2$R'$_2$-M and —CR$_2$R'$_2$SO$_n$-M;
R$_1$ is selected from the group consisting of C$_{1-6}$ alkyl, halogen, —CN, C$_{1-6}$-alkoxy, C$_{1-6}$-fluoroalkyl, C$_{1-6}$-fluroalkoxy and C$_{1-6}$-alkylthio;
R$_2$ and R'$_2$ are independently selected from the group consisting of H and C$_{1-6}$ alkyl;
M and M' are independently selected from aryl optionally substituted with 1 to 3 R$_1$, heteroaryl optionally substituted with 1 to 3 R$_1$ and cycloalkyl of 3 to 8 carbons; and
n=0, 1, or 2;
or a pharmaceutically acceptable salt thereof.

2. A compound of formula (Ic),

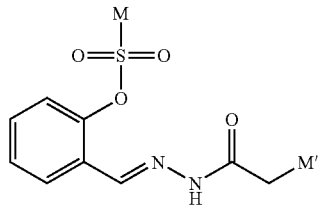

wherein:
R$_1$ is selected from the group consisting of C$_{1-6}$ alkyl, halogen, —CN, C$_{1-6}$-alkoxy, C$_{1-6}$-fluoroalkyl, C$_{1-6}$-fluroalkoxy and C$_{1-6}$-alkylthio; and
M and M' are independently selected from aryl optionally substituted with 1 to 3 R$_1$, heteroaryl optionally substituted with 1 to 3 R$_1$ and cycloalkyl of 3 to 8 carbons;
or a pharmaceutically acceptable salt or prodrug thereof.

3. A compound according to claim 2, wherein M and M' are aryl optionally substituted with 1 to 3 R, or a pharmaceutically acceptable salt thereof.

4. A compound according to claim 2, wherein M and M' are heteroaryl optionally substituted with 1 to 3 R$_1$, or a pharmaceutically acceptable salt thereof.

5. A compound selected from the group consisting of:
N-(2-{(E)-[(2,5-dichlorobenzoyl)hydrazono]methyl}phenyl)-N-methyl-4-(trifluoromethyl)benzenesulfonamide;
2-((E)-{2-[2-(1,3-benzodioxol-5-yl)acetyl]hydrazono}methyl)phenyl 4-(trifluoromethyl)benzenesulfonate;
2-((E)-{2-[(4-methylphenyl)sulfonyl]hydrazono}methyl)phenyl 4-(trifluoromethyl)benzenesulfonate;
3-chloro-2-((E)-{[(3-methoxyphenyl)acetyl]hydrazono}methyl)phenyl 4-(trifluoromethyl)benzenesulfonate;
N-[2-((E)-{[(3-bromophenyl)acetyl]hydrazono}methyl)phenyl]-N-methyl-4-(trifluoromethyl)benzenesulfonamide;
2-((E)-{2-[2-(3-methoxyphenyl)acetyl]hydrazono}methyl)phenyl 4-(trifluoromethyl)benzenesulfonate;
2-((E)-{2-[2-(3-methoxyphenyl)acetyl]hydrazono}methyl)phenyl 4-methylbenzenesulfonate;
2-((E)-{[(3-methoxyphenyl)acetyl]hydrazono}methyl)-3-methylphenyl 4-(trifluoromethyl)benzenesulfonate;
2-((E)-{2-[2-fluoro-6-(trifluoromethyl)benzoyl]hydrazono}methyl)phenyl 4-(trifluoromethyl)benzenesulfonate;
2-((E)-{2-[2-(trifluoromethyl)benzoyl]hydrazono}methyl)phenyl 4-(trifluoromethyl)benzenesulfonate;
N-(2-{(E)-[(1,3-benzodioxol-5-ylacetyl)hydrazono]methyl}phenyl)-N-methyl-4-(trifluoromethyl)benzenesulfonamide;
2-{(E)-[2-(2-bicyclo[2.2.1]hept-2-ylacetyl)hydrazono]methyl}phenyl 4-(trifluoromethyl)benzenesulfonate;
N-methyl-N-(2-{(E)-[(phenylacetyl)hydrazono]methyl}phenyl)-4-(trifluoromethyl)benzenesulfonamide;
N-[2-((E)-{[(3-chlorophenyl)acetyl]hydrazono}methyl)phenyl]-N-methyl-4-(trifluoromethyl)benzenesulfonamide;
2-{(E)-[2-(2,6-difluorobenzoyl)hydrazono]methyl}phenyl-4-(trifluoromethyl)benzenesulfonate;
2-((E)-{2-[2-(6-chloropyridin-3-yl)acetyl]hydrazono}methyl)phenyl 4-(trifluoromethyl)benzenesulfonate;
2-((E)-{2-[2-(3-chlorophenyl)acetyl]hydrazono}methyl)phenyl-4-(trifluoromethyl)benzenesulfonate;
2-{(E)-[2-(2-thien-2-ylacetyl)hydrazono]methyl}phenyl-4-(trifluoromethyl)benzenesulfonate;
4-fluoro-2-((E)-{[(3-methoxyphenyl)acetyl]hydrazono}methyl)phenyl-4-(trifluoromethyl)benzenesulfonate;
3-chloro-2-((E)-{[(3-chlorophenyl)acetyl]hydrazono}methyl)phenyl-4-(trifluoromethyl)benzenesulfonate;
4-fluoro-2-((E)-{[(3-methoxyphenyl)acetyl]hydrazono}methyl)phenyl-4-methylbenzenesulfonate and
2-(3-methoxyphenyl)-N'-[(1E)-(2-{[(4-methylphenyl)sulfonyl]methyl}phenyl)methylene]acetohydrazide;
or a pharmaceutically acceptable salt thereof.

6. A method for treating a hepatitis C viral infection comprising administering, to an animal in need thereof, an effective amount of a compound according to claim 1.

7. A method according to claim 6, wherein the compound is selected from the group consisting of:
N-(2-{(E)-[(2,5-dichlorobenzoyl)hydrazono]methyl}phenyl)-N-methyl-4-(trifluoromethyl)benzenesulfonamide;
2-((E)-{2-[2-(1,3-benzodioxol-5-yl)acetyl]hydrazono}methyl)phenyl 4-(trifluoromethyl)benzenesulfonate;
2-((E)-{2-[(4-methylphenyl)sulfonyl]hydrazono}methyl)phenyl 4-(trifluoromethyl)benzenesulfonate;
3-chloro-2-((E)-{[(3-methoxyphenyl)acetyl]hydrazono}methyl)phenyl 4-(trifluoromethyl)benzenesulfonate;

N-[2-((E)-{[(3-bromophenyl)acetyl]hydrazono}methyl)
phenyl]-N-methyl-4-(trifluoromethyl)benzenesulfona-
mide;

2-((E)-{2-[2-(3-methoxyphenyl)acetyl]
hydrazono}methyl)phenyl 4-(trifluoromethyl)benzene-
sulfonate;

2-((E)-{2-[2-(3-methoxyphenyl)acetyl]
hydrazono}methyl)phenyl 4-methylbenzenesulfonate;

2-((E)-{[(3-methoxyphenyl)acetyl]hydrazono}methyl)-
3-methylphenyl 4-(trifluoromethyl)benzenesulfonate;

2-((E)-{2-[2-fluoro-6-(trifluoromethyl)benzoyl]
hydrazono}methyl)phenyl 4-(trifluoromethyl)benzene-
sulfonate;

2-((E)-{2-[2-(trifluoromethyl)benzoyl]
hydrazono}methyl)phenyl 4-(trifluoromethyl)benzene-
sulfonate;

N-(2-{(E)-[(1,3-benzodioxol-5-ylacetyl)hydrazono]
methyl}phenyl)-N-methyl-4-(trifluoromethyl)benze-
nesulfonamide;

2-{(E)-[2-(2-bicyclo[2.2.1]hept-2-ylacetyl)hydrazono]
methyl}phenyl 4-(trifluoromethyl)benzenesulfonate;

N-methyl-N-(2-{(E)-[(phenylacetyl)hydrazono]
methyl}phenyl)-4-(trifluoromethyl)benzenesulfona-
mide;

N-[2-((E)-{[(3-chlorophenyl)acetyl]hydrazono}methyl)
phenyl]-N-methyl-4-(trifluoromethyl)benzenesulfona-
mide;

2-{(E)-[2-(2,6-difluorobenzoyl)hydrazono]
methyl}phenyl 4-(trifluoromethyl)benzenesulfonate;

2-((E)-{2-[2-(6-chloropyridin-3-yl)acetyl]
hydrazono}methyl)phenyl 4-(trifluoromethyl)benzene-
sulfonate;

2-((E)-{2-[2-(3-chlorophenyl)acetyl]hydrazono}methyl)
phenyl-4-(trifluoromethyl)benzenesulfonate;

2-{(E)-[2-(2-thien-2-ylacetyl)hydrazono]methyl}phenyl-
4-(trifluoromethyl)benzenesulfonate;

118 or 4-fluoro-2-((E)-{[(3-methoxyphenyl)acetyl]
hydrazono}methyl)phenyl-4-(trifluoromethyl)benze-
nesulfonate;

3-chloro-2-((E)-{[(3-chlorophenyl)acetyl]
hydrazono}methyl)phenyl-4-(trifluoromethyl)benze-
nesulfonate;

4-fluoro-2-((E)-{[(3-methoxyphenyl)acetyl]
hydrazono}methyl)phenyl-4-methylbenzenesulfonate;
and 2-(3-methoxyphenyl)-N'-[(1E)-(2-{[(4-methylphenyl)
sulfonyl]methyl}phenyl)methylene]acetohydrazide; or
a pharmaceutically acceptable salt thereof.

8. A pharmaceutical composition, comprising a pharmaceutically acceptable carrier and a therapeutically or prophylactically effective amount of a compound according to claim 1.

* * * * *